United States Patent
Roberts et al.

(10) Patent No.: US 9,149,592 B2
(45) Date of Patent: Oct. 6, 2015

(54) ASPIRATION CATHETERS, SYSTEMS, AND METHODS

(71) Applicant: Patient Centered Medical Incorporated, Brentwood, TN (US)

(72) Inventors: John R. Roberts, Brentwood, TN (US); Eran Levit, Amherst, NH (US); Janet Elaine Bloom, Hopkinton, NH (US); Timothy Roberts, Brentwood, TN (US); Maya Elaine Bloom, Hopkinton, NH (US)

(73) Assignee: PATIENT CENTERED MEDICAL INCORPORATED, Brentwood, TN (US)

( * ) Notice: Subject to any disclaimer, the term of this patent is extended or adjusted under 35 U.S.C. 154(b) by 0 days.

(21) Appl. No.: 14/452,310

(22) Filed: Aug. 5, 2014

(65) Prior Publication Data
US 2014/0350458 A1 Nov. 27, 2014

Related U.S. Application Data

(63) Continuation of application No. 14/213,795, filed on Mar. 14, 2014.

(60) Provisional application No. 61/787,286, filed on Mar. 15, 2013, provisional application No. 61/921,910, filed on Dec. 30, 2013.

(51) Int. Cl.
*A61M 16/04* (2006.01)
(Continued)

(52) U.S. Cl.
CPC ........... *A61M 16/04* (2013.01); *A61M 16/0418* (2014.02); *A61M 16/0431* (2014.02);
(Continued)

(58) Field of Classification Search
CPC . A61M 16/0431; A61M 16/00; A61M 16/04; A61M 16/0418; A61M 16/0486; A61M 25/0023; A61M 25/0021; A61M 25/0041; A61M 25/00; A61M 25/001; A61M 25/0015; A61M 25/0026; A61M 25/032; A61M 25/0043; A61M 25/0054; A61M 25/0067; A61M 25/0068; A61M 25/007; A61M 25/0071; A61M 25/0133; A61M 25/0141; A61M 25/0152; A61M 1/008; A61M 1/0082; A61M 1/0084; A61M 3/00; A61M 3/0279; A61M 3/0283; A61B 2017/003; A61B 2017/00305; A61B 2017/0034; A61B 1/267; A61B 1/2676; A61B 1/2673; A61B 17/24
See application file for complete search history.

(56) References Cited

U.S. PATENT DOCUMENTS 2,862,498 A 12/1958 Weekes
(Continued)

FOREIGN PATENT DOCUMENTS

EP 1767182 A1 3/2007
(Continued)

OTHER PUBLICATIONS

PCT/US2011/062438: International Search Report and Written Opinion, Jun. 11, 2012.
(Continued)

*Primary Examiner* — Justine Yu
*Assistant Examiner* — Colin W Stuart
(74) *Attorney, Agent, or Firm* — Venable LLP; Michele V. Frank

(57) ABSTRACT

The aspiration catheters, systems and methods include a catheter having an elongated body with a cross-section having a flat side and a curve near the distal end. The first side of the cross-section can contact a first side of a delivery lumen in a first orientation, and a second side of the cross-section contacts the first side of the delivery lumen in a second orientation rotated 180° from the first orientation. The curve can be directed 90° relative to a normal of the flat side. The systems and methods can utilize two catheters, and a key joint formed with the two catheters which can rotationally fix the catheters with respect to each other, and the first and second catheters each include at least one pre-formed curve near the distal end. The two catheters can be moved proximally and distally for positioning in the right and left bronchi.

29 Claims, 43 Drawing Sheets

(51) Int. Cl.
*A61M 39/10* (2006.01)
*A61M 25/00* (2006.01)
*A61M 25/01* (2006.01)
*A61M 25/06* (2006.01)

(52) U.S. Cl.
CPC ......... *A61M16/0463* (2013.01); *A61M 25/007* (2013.01); *A61M 25/0015* (2013.01); *A61M 25/0021* (2013.01); *A61M 25/0041* (2013.01); *A61M 25/0067* (2013.01); *A61M 25/0068* (2013.01); *A61M 39/10* (2013.01); *A61M 16/0404* (2014.02); *A61M 16/0486* (2014.02); *A61M 25/0023* (2013.01); *A61M 25/0111* (2013.01); *A61M 2025/0681* (2013.01)

(56) References Cited

U.S. PATENT DOCUMENTS

| | | | |
|---|---|---|---|
| 2,949,910 | A | 8/1960 | Brown |
| 3,858,575 | A | 1/1975 | Rose |
| 4,344,436 | A | 8/1982 | Kubota |
| 4,488,548 | A | 12/1984 | Agdanowski |
| 4,502,482 | A | 3/1985 | DeLuccia et al. |
| 4,512,765 | A | 4/1985 | Muto |
| 4,716,896 | A | 1/1988 | Ackerman |
| 4,777,961 | A | 10/1988 | Saltzman |
| 4,840,172 | A | 6/1989 | Augustine et al. |
| 4,981,477 | A * | 1/1991 | Schon et al. ............. 604/264 |
| 5,135,490 | A | 8/1992 | Strickland |
| 5,246,012 | A | 9/1993 | Strickland |
| 5,606,968 | A | 3/1997 | Mang |
| 5,660,175 | A | 8/1997 | Dayal |
| 5,775,322 | A | 7/1998 | Silverstein et al. |
| 5,844,997 | A | 12/1998 | Murphy, Jr. |
| 5,964,223 | A | 10/1999 | Baran |
| 6,053,166 | A | 4/2000 | Gomez |
| 6,064,902 | A | 5/2000 | Haissaguerre et al. |
| 6,306,097 | B1 | 10/2001 | Park et al. |
| 6,349,720 | B1 | 2/2002 | Clark |
| 6,443,156 | B1 * | 9/2002 | Niklason et al. ......... 128/207.14 |
| 6,513,527 | B1 | 2/2003 | Abdel-Aziz |
| 6,520,183 | B2 | 2/2003 | Amar |
| 6,568,393 | B2 | 5/2003 | Christopher |
| 7,097,643 | B2 | 8/2006 | Cornelius et al. |
| 7,967,770 | B2 * | 6/2011 | Li et al. .............................. 604/8 |
| 2003/0018276 | A1 | 1/2003 | Mansy et al. |
| 2003/0125619 | A1 | 7/2003 | Manning et al. |
| 2003/0144623 | A1 * | 7/2003 | Heath et al. ................. 604/4.01 |
| 2004/0158228 | A1 * | 8/2004 | Perkins et al. ................ 604/514 |
| 2005/0080334 | A1 | 4/2005 | Willis |
| 2005/0103332 | A1 | 5/2005 | Gingles et al. |
| 2005/0197623 | A1 | 9/2005 | Leeflang et al. |
| 2005/0261665 | A1 * | 11/2005 | Voorhees ...................... 604/508 |
| 2006/0241564 | A1 | 10/2006 | Corcoran et al. |
| 2007/0010762 | A1 | 1/2007 | Ressemann et al. |
| 2007/0078463 | A1 | 4/2007 | Malandain |
| 2009/0118612 | A1 | 5/2009 | Grunwald et al. |
| 2009/0187164 | A1 | 7/2009 | Rowe |
| 2009/0204052 | A1 * | 8/2009 | Nimkar et al. ............... 604/6.16 |
| 2009/0248045 | A1 | 10/2009 | Trovato |
| 2009/0292209 | A1 | 11/2009 | Hadjicostis |
| 2010/0198141 | A1 | 8/2010 | Laitenberger et al. |
| 2010/0300449 | A1 | 12/2010 | Chan et al. |
| 2010/0307508 | A1 * | 12/2010 | Li et al. .................... 128/207.15 |
| 2011/0201887 | A1 | 8/2011 | Greenblatt et al. |
| 2011/0245665 | A1 | 10/2011 | Nentwick |
| 2012/0101442 | A1 * | 4/2012 | Legaspi et al. ................ 604/175 |
| 2012/0259206 | A1 | 10/2012 | Roberts et al. |
| 2012/0259208 | A1 | 10/2012 | Bloom et al. |
| 2014/0261407 | A1 * | 9/2014 | Roberts et al. ........... 128/202.16 |

FOREIGN PATENT DOCUMENTS

| | | |
|---|---|---|
| GB | 2397229 A | 7/2004 |
| WO | 97/49445 A1 | 12/1997 |
| WO | 2007/008332 A2 | 1/2007 |
| WO | 2008/032230 A1 | 3/2008 |
| WO | 2010/044051 A1 | 4/2010 |

OTHER PUBLICATIONS

PCT/US2011/062440: International Search Report and Written Opinion dated Jun. 11, 2012.
PCT/US2012/032547: International Search Report and Written Opinion dated Jan. 28, 2013.
Airwaycam.com, Tracheal Tube Design and Delivery, http://www.airwaycam.com/intubation-Endotrachael-Tube-design.html, 2011.
NDT Resource Center, "Vibration" htt;://www.ndt-ed.org/EducationResources/HighSchool/Sound/vibration.htm, 2008.
M.K. Sykes, Improved Plastic Endotracheal Tubes, British Medical Journal, Apr. 20, 1968.
U.S. Appl. No. 13/083,462: Office Action mailed Jan. 2, 2015.
PCT/US2014/029265: International Search Report and Written Opinion mailed Oct. 24, 2014.

* cited by examiner

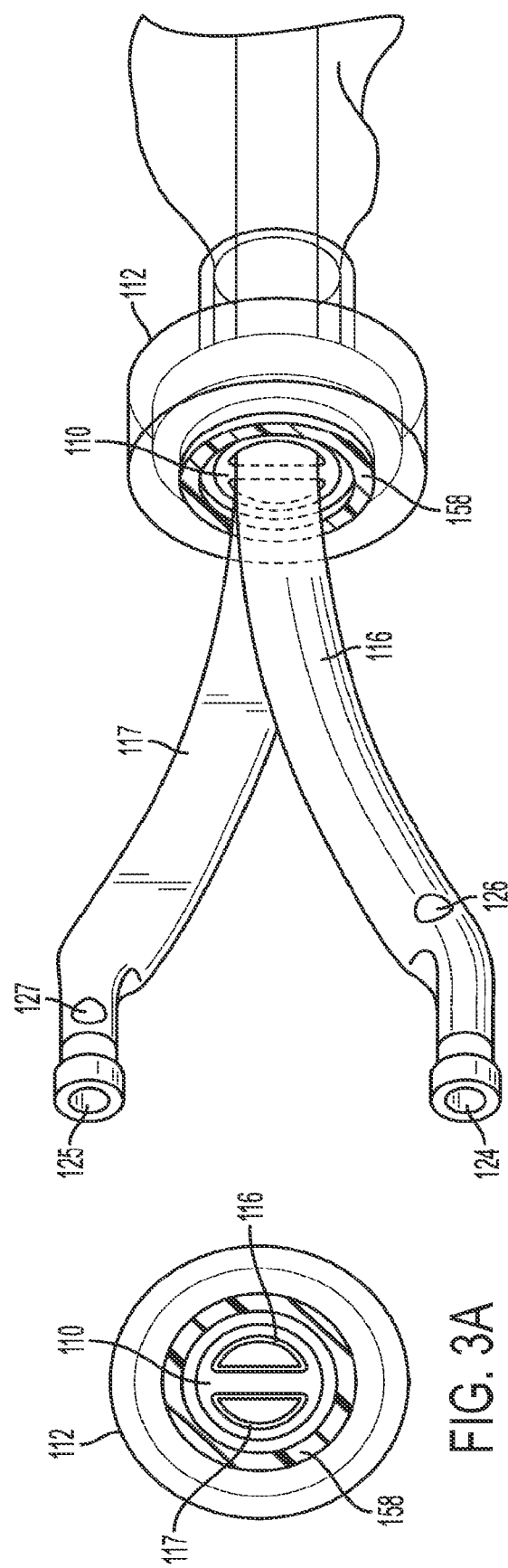

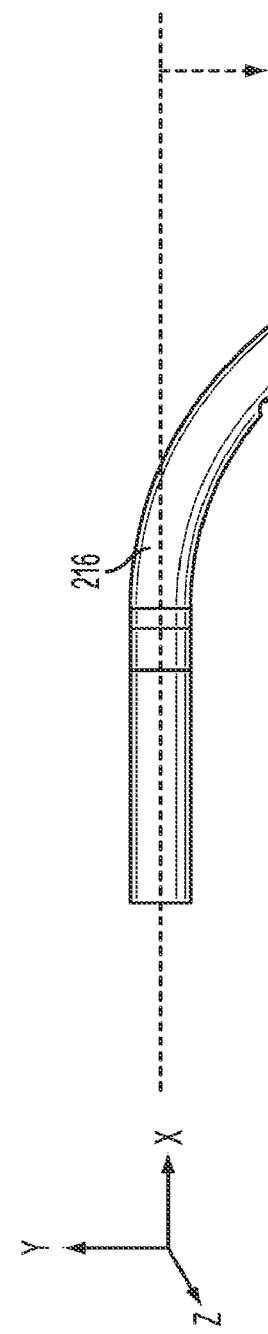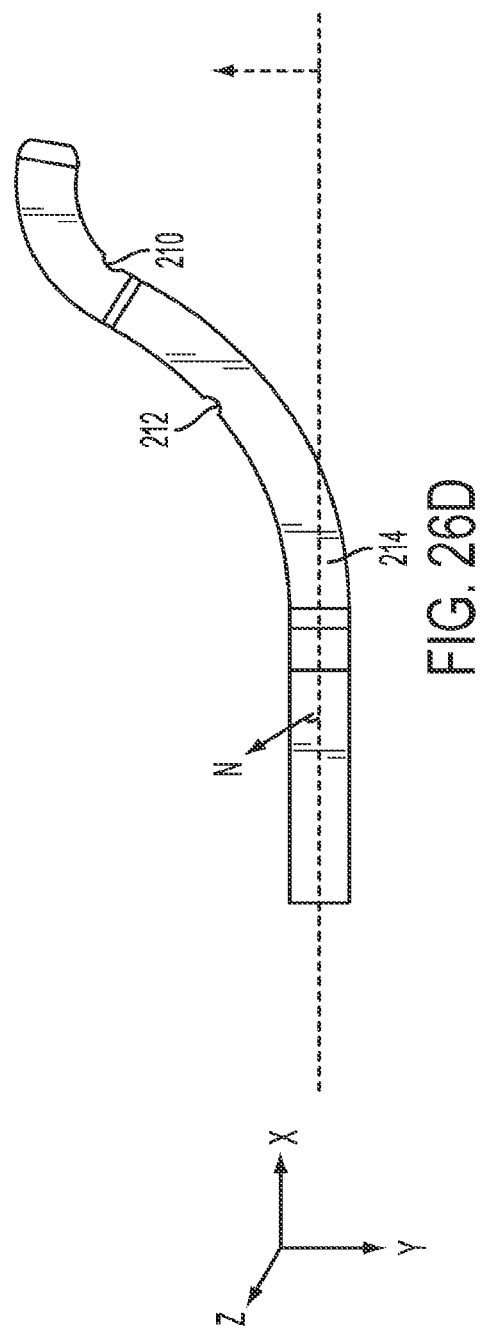
FIG. 26C
FIG. 26D

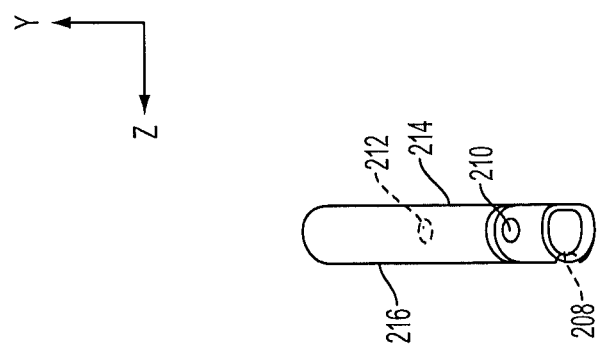
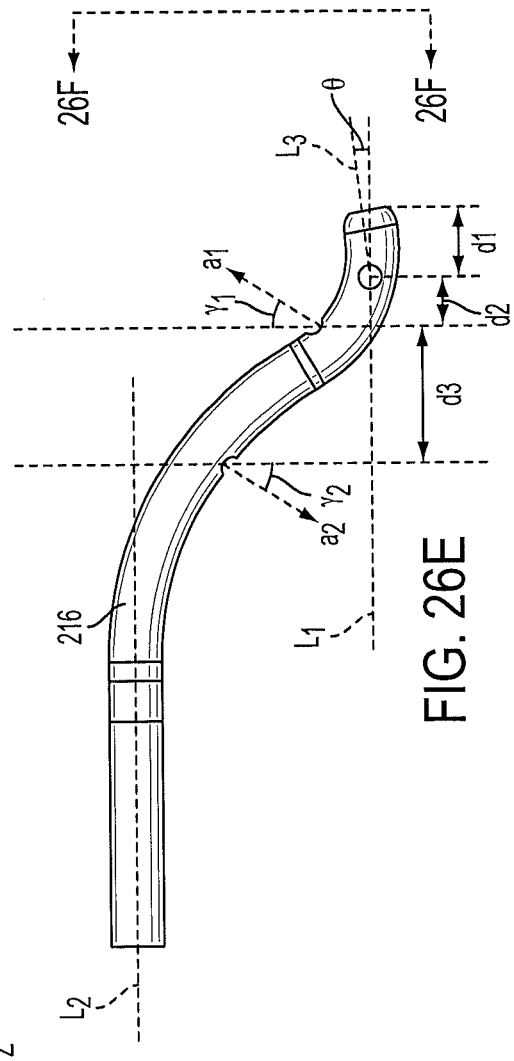
FIG. 26F
FIG. 26E

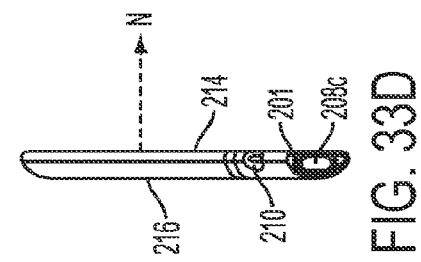
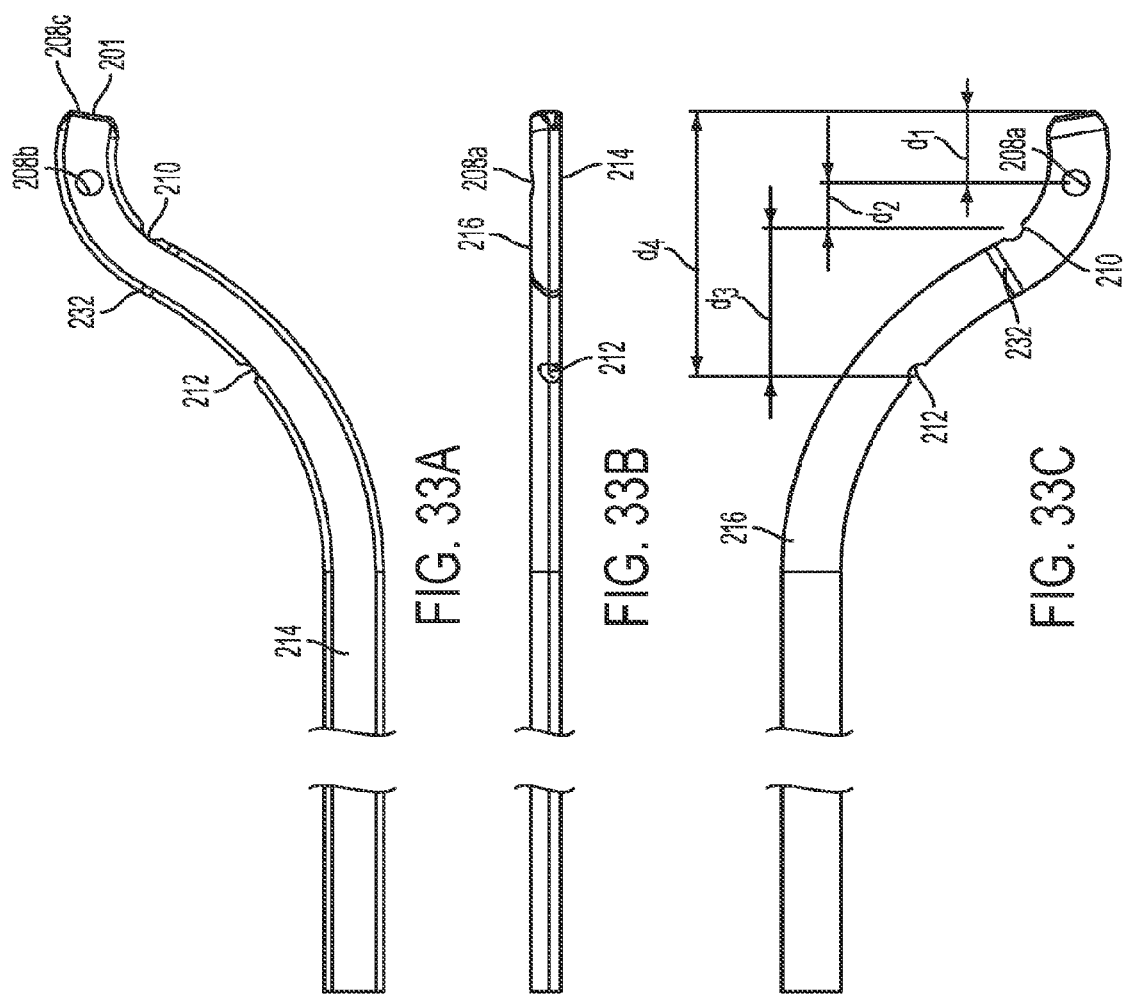
FIG. 33A  FIG. 33B  FIG. 33C  FIG. 33D

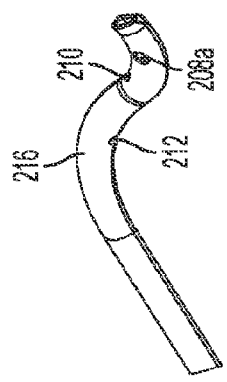
FIG. 34A
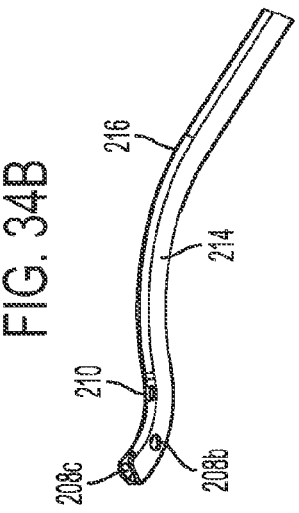
FIG. 34B / FIG. 34C
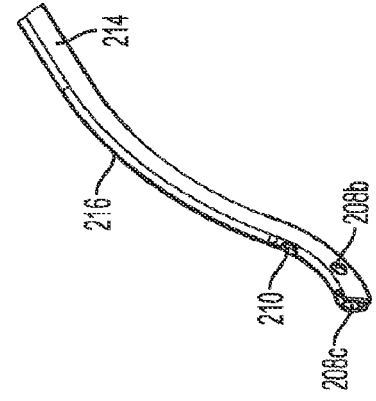
FIG. 34D / FIG. 34F
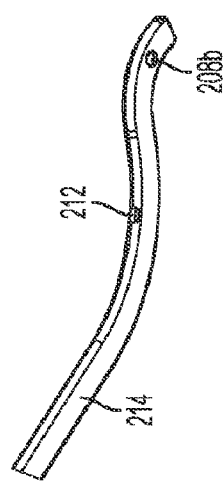
FIG. 34E
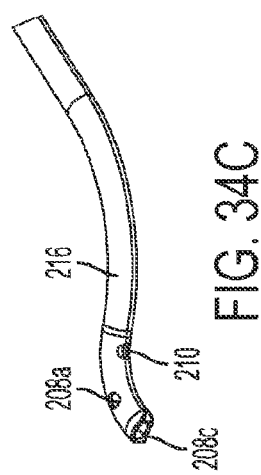

ASPIRATION CATHETERS, SYSTEMS, AND METHODS

CROSS-REFERENCE TO RELATED APPLICATIONS

This application is a continuation of U.S. patent application Ser. No. 14/213,795, filed Mar. 14, 2014, which claims priority to U.S. Provisional Application Nos. 61/787,286, filed Mar. 15, 2013; and 61/921,910, filed Dec. 30, 2013, the disclosures of all of which are incorporated herein by reference in their entireties.

TECHNICAL FIELD

The present invention relates to medical devices and, in particular, to catheters that can be reliably advanced into tortuous body lumens and for which the location and orientation of the catheters within body lumens can be reliably verified.

BACKGROUND

Suction catheters are used to remove respiratory secretions and other material from airways, and in general for treating or preventing a number of respiratory conditions. For example, when patients develop pneumonia or bronchitis they cough to clear the airways. If, however, the pneumonia worsens enough to require intubation with an endotracheal tube and placement on a ventilator (breathing machine), patients are unable to cough (due to sedation and the mechanical impediment of the endotracheal tube), and so suction catheters are passed into the endotracheal tube to clear the infected mucous and thus improve the ability to breathe and to help treat the infection. Suction catheters may also be used in patients without pneumonia to prevent the occurrence of pneumonia or other respiratory complications. However, the right bronchus (airway) is straighter and of greater diameter, so that suction catheters passed into the trachea go into the right bronchus more than 98% of the time. This anatomic fact is well known by all physicians (pulmonologists, surgeons and anesthesiologists) who manage the airway.

The current suction catheters are passed blindly into the trachea and cannot be directed into either side. They are connected to the endotracheal tube, and kept on the patient's bed inside a sleeve that is not sterilized, and allow the bacteria to grow and accumulate. Thus, the catheters become contaminated, contaminate the sleeve, and re-introduce the same bacteria back into the patient's airway when suctioning is repeated. Thus, it re-introduces the problem that it is designed to eradicate: infected secretions.

Because usually only the right lung is cleared of secretions, the left lung becomes a reservoir of infection, even if the right lung is the source of infection, as secretions from either lung move or contaminate the opposite lung. If the right lung is the source of the pneumonia, for example, this reservoir may be limited. However, if the left lung is the source, it will never be cleared by standard suctioning, and often requires bronchoscopy. This failure to clear the lung prolongs time on the ventilator, prolongs the recovery time from pneumonia, and increases the risk of developing resistant infections and of dying from pneumonia.

Together, pneumonia and influenza represented a cost to the U.S. economy in 2005 of $40.2 billion, $6 billion due to indirect mortality I costs and $34.2 billion in direct II costs, according to the American Lung Association. According to preliminary mortality data from 2011 from the CDC, age-adjusted death rates decreased significantly from 2010 to 2011 for 5 of the 15 leading causes of death (heart diseases, Malignant neoplasms, Cerebrovascular disease, Alzheimer's disease, and kidney diseases). However, the age-adjusted death rate increased for six leading causes of death: Chronic lower respiratory diseases, Diabetes mellitus, Influenza and pneumonia, Chronic liver disease and cirrhosis, Parkinson's disease, and Pneumonitis due to solids and liquids. Three of these causes (chronic lower respiratory disease, influenza and pneumonia, and pneumonitis) are all variants of pneumonia. These data demonstrate that pneumonia is an already dangerous disease that is becoming more deadly.

There exists a need for improved treatment and prevention of pneumonia and other respiratory conditions and complications.

BRIEF SUMMARY OF THE INVENTION

An embodiment of the present invention may provide a catheter for insertion into a body lumen of a patient. The catheter may include a distal end for insertion into the body lumen of the patient, a proximal end, and an elongated body extending between the proximal and distal ends. The elongated body may have a cross-section that includes, over at least a portion of the elongated body, a first side that is flat and a second side on an opposite side of the cross-section from the first side. The catheter may also include at least one lumen extending through the elongated body from the proximal end to the distal end, and at least one pre-formed curve near the distal end. When the distal end is inserted into the body lumen of the patient, the first side of the cross-section may contact a first inner side of a delivery lumen of the catheter while the catheter is in a first orientation, and the second side of the cross-section may contact the first inner side of the delivery lumen of the catheter while the catheter is in a second orientation. The second orientation may be a 180° rotation of the catheter about a longitudinal axis of the elongated body relative to the first orientation. The pre-formed curve may have a curve direction that is 90° with respect to a normal direction of the flat side of the cross-section.

Embodiments of the present invention may include a catheter having a distal end for insertion into the body lumen of the patient, a proximal end, and an elongated body extending between the proximal and distal ends. The elongated body may have a cross-section that includes, over at least a portion of the elongated body, a portion that is substantially flat, and also may have a torqueability ratio of 1:1 between the distal and proximal ends. The catheter may also include at least one lumen extending through the elongated body from the proximal end to the distal end. The elongated body may be arranged in a delivery lumen of an outer catheter such that, when the distal end is inserted into the body lumen of the patient, the distal end is directed toward one of a left bronchus and a right bronchus of the patient. The distal end may remain directed toward the one of the left and right bronchi during a rotation of the proximal end about a longitudinal axis of the elongated body until a predetermined angle of rotation of the proximal end is reached, at which point the distal end may flip to the other of the left bronchus and the right bronchus.

Embodiments of the present invention may include a catheter for insertion into a body lumen of a patient. The catheter may include a distal end, a proximal end, and an elongated body extending between the proximal and distal ends and having a torqueability ratio of 1:1 between the distal and proximal ends. The catheter may also include at least one lumen extending through the elongated body from the proximal end to the distal end. The elongated body may also have a torsional stiffness such that, when the elongated body is inserted into a delivery lumen of an outer catheter, the distal end remains in one of a first resting orientation and a second resting orientation during a rotation of the proximal end about a longitudinal axis of the catheter.

Embodiments of the present invention may provide a method of orienting a catheter in a body lumen of a patient. The method may include providing the catheter that may have a distal end, a proximal end, and an elongated body extending between the proximal and distal ends. The method may also include providing an outer catheter for insertion into a body lumen of a patient and to receive the distal end of the catheter. The method may further include inserting the catheter into the body lumen of the patient through the outer catheter, and rotationally orienting the proximal end of the catheter to a first orientation. The distal end of the catheter may be directed toward one of a left bronchus and a right bronchus of the patient in the first orientation. The method may further include changing a direction of the distal end of the catheter by rotating the proximal end of the catheter to a second orientation, the second orientation being a substantially 180° rotation of the proximal end relative to the first orientation, and the distal end being directed toward the other of the left and right bronchi when the proximal end is in the second orientation.

Embodiments of the present invention may provide a catheter for insertion into a body lumen of a patient. The catheter may include a distal end for insertion into the body lumen of the patient, a proximal end, and an elongated body extending between the proximal and distal ends. The elongated body may have a cross-section that includes, over at least a portion of the elongated body, a portion that is substantially flat. The catheter may also include at least one lumen extending through the elongated body from the proximal end to the distal end, and at least one pre-formed curve near the distal end of the elongated body. The at least one pre-formed curve may curve the catheter in a direction that is orthogonal to a normal direction of the flat side of the cross-section.

Embodiments of the present invention may also provide a catheter system that includes a first catheter. The first catheter may include a proximal end, a distal end for insertion into a body lumen of a patient, and an elongated body extending between the proximal and distal ends. The elongated body may have a cross-section that includes, over at least a portion of the elongated body, a first side that is flat and a second side on an opposite side of the cross-section from the first side, and may also have at least one lumen extending through the elongated body from the proximal end to the distal end. The catheter system may also include a second catheter that can include a proximal end, a distal end, an elongated body extending between the proximal and distal ends and having a cross-section that includes, over at least a portion of the elongated body, a first side that is flat and a second side on an opposite side of the cross-section from the first side. The elongated body of the second catheter may also include at least one lumen extending through the elongated body from the proximal end to the distal end. The catheter system may include a key joint component to form a key joint with at least a portion of the elongated bodies near the proximal ends of both the first and second catheters, the portion of the elongated bodies that form the key joint including the first sides that are flat. The first and second catheters may be rotationally fixed with respect to each other via the key joint, and the elongated bodies of the first and second catheters may each include at least one pre-formed curve near the distal end.

Embodiments of the present invention may provide a method of using a catheter system. The method may include providing a dual catheter system including a first catheter and a second catheter. Each of the first and second catheters may have a proximal end, a distal end, and an elongated body extending between the proximal and distal ends. The elongated body may have a cross-section that includes, over at least a portion of the elongated body, a first side that is flat and a second side on an opposite side of the cross-section from the first side. The catheter system may also include a key joint component configured to form a key joint with at least a portion of the elongated bodies near the proximal ends of both the first and second catheters. The portion of the elongated bodies that form the key joint may include the first sides that are flat. The first and second catheters may be rotationally fixed relative to the key joint component via the key joint. The first side that is flat of the first catheter may face the first side that is flat of the second catheter. The method may also include advancing the distal ends of the first and second catheters through the body lumen of the patient, and controlling a disposition of the first and second catheters such that at least one of the first and second catheters is directed toward one of a left bronchus and a right bronchus of the patient Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 3A shows a cross-section view, according to the broken line in FIG. 2B, of the connection portion with a key joint component of a first catheter, and a second and third catheter forming a keyed joint with the key joint component of the first catheter in an embodiment of the present invention.

FIG. 3B shows a side perspective view of the connection portion with the second and third catheters extending from the key joint component of the first catheter in an embodiment of the present invention.

FIG. 26C shows a first side view of the distal end of the catheter shown in FIG. 26A according to an embodiment of the present invention.

FIG. 26D shows a second side view of the distal end of the catheter shown in FIG. 26A according to an embodiment of the present invention.

FIG. 26E shows an additional first side view of the distal end of the catheter shown in FIG. 26A according to an embodiment of the present invention.

FIG. 26F shows a front view of distal end of the catheter shown in FIG. 26A according to an embodiment of the present invention.

FIG. 33A shows a bottom view of the distal end of the catheter showing the flat side in an embodiment of the invention.

FIG. 33B shows a side view of the distal end of the catheter in an embodiment of the invention.

FIG. 33C shows a top view of the distal end of the catheter in an embodiment of the invention.

FIG. 33D shows a front view of the distal end of the catheter in an embodiment of the invention.

FIGS. 34A, 34B, 34C, 34D, 34E, and 34F show a variety of isometric views of the distal end of the catheter in an embodiment of the invention.

DETAILED DESCRIPTION OF THE INVENTION

Figure 1:
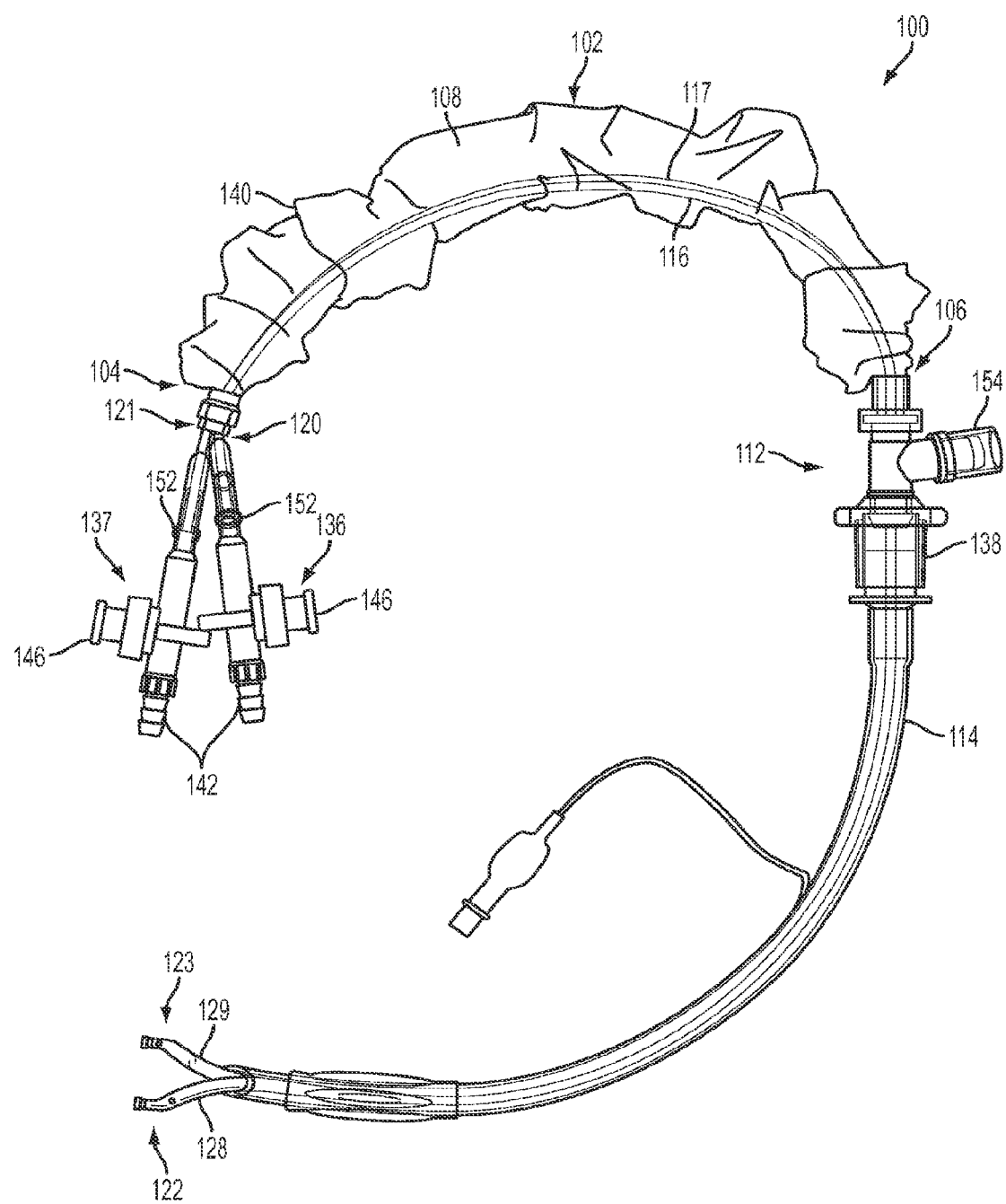
FIG. 1 shows a view of a catheter system with endotracheal tube in an embodiment of the present invention.

Systems and methods are provided for positioning and using a catheter within a body lumen of a patient (e.g., the left and right main bronchi), without requiring direct visualization. The system may allow the desired placement of a working catheter within either bronchus without using endoscopy to assure placement.

The catheters, systems, and methods can be utilized in various applications to suction and/or remove material, such as respiratory secretions from the airways. The catheters, systems, and methods can also be utilized for irrigation, alone, or in combination with aspiration. The catheters, systems, and methods can be used for treating and/or preventing conditions requiring aspiration and/or irrigation, including any type of respiratory conditions. Such respiratory conditions can include pneumonia or bronchitis, for example, and prevention or treatment, for example.

The system and methods may include various implementations, examples of which are described herein. The methods and systems may be implemented as open and/or closed methods and systems. The catheters may be utilized as a single catheter, dual catheter, and/or a combination of both.

In some embodiments, a catheter system includes a first catheter including a first proximal end portion, a first body portion, a first distal end portion, a lumen extending through the first body portion from the first proximal end portion to the first distal end portion, and a first key joint component. The catheter system may also include a second catheter including a second proximal end portion, a second body portion, a second distal end portion, a primary lumen extending through the second body portion from the second proximal end portion to the second distal end portion, at least a portion of the second body portion being disposed within the lumen of the first catheter, the second catheter further including a second key joint component. The second key joint component may form a first keyed joint with the first key joint component such that the second catheter is rotationally fixed with respect to the first key joint component via the first keyed joint, the second distal end portion being configured be inserted into a body of a patient. The second catheter may be configured to have a torqueability ratio of 1:1 between the second distal end portion and the second key joint component.

In some embodiments, a method of positioning and using a catheter system is provided. The method of positioning and using at least one catheter within a lumen of a body of a patient may include providing a first catheter that includes a first distal end portion, a first proximal end portion, a first lumen extending between the first proximal end portion and the first distal end portion, and a first key joint component. The method may further include providing, within the first lumen of the first catheter, a second catheter that includes a second distal end portion, a second proximal end portion, a second lumen extending between the second proximal end portion and the second distal end portion, and a second key joint component forming a first keyed joint, within the first distal end portion, with the first key joint component. Further, the method may include extending the second distal end portion of the second catheter from the first distal end portion into the body of the patient, and positioning the second distal end portion in a predetermined relationship with a first targeted lumen within the body of the patient by rotating the first keyed joint such that the second distal end portion is rotated into an orientation for establishing the predetermined relationship.

In some embodiments, the catheter includes an elongated body having a proximal end portion and a distal end portion. The elongated body can define a lumen extending from the proximal end portion to the distal end portion, and can include a key joint component that corresponds with a key joint component of a lumen of a delivery catheter. The key joint component of the elongated body of the catheter can be configured to be selectively coupled to the key joint component of the lumen of the delivery catheter such that a rotational orientation of the catheter is fixed relative to a rotation orientation of the delivery catheter.

In some embodiments, the catheter system includes a ventilation adapter attached to the proximal end of an endotracheal tube. The adapter includes a first key joint component. The first catheter can include a first elongated body having a first proximal end portion, a first distal end portion, and a shaped elongated body disposed within the ventilation adapter. The catheter system can also include a second catheter slideably disposed within the ventilation adapter. The second catheter can include a second elongated body having a second distal end portion and a second key joint component that corresponds with the first key joint component in the adapter. The adapter key joint component, the first catheter key joint component and the second catheter key joint component can be configured to be coupled together such that a rotational orientation of the catheters is fixed relative to a rotational orientation of the ventilation adapter.

In some embodiments, the catheter system includes a ventilation adapter attached to the proximal end of an endotracheal tube. The first catheter has a first elongated body including a first proximal end portion, a first distal end portion, and first and second lumens extending from the first proximal end portion to the first distal end portion slideably disposed within the adapter. The first catheter has a second elongated body including a second distal end portion and a second proximal end portion. The second distal end portion of the first catheter can include a pre-formed bend that extends at a non-zero angle relative to a longitudinal axis of the first catheter when the second distal end portion is extended through the adapter. The catheter system can also include a second catheter slideably disposed within the ventilation adapter. The second catheter can have a second elongated body including a second distal end portion and a second proximal end portion. The second distal end portion of the second catheter can include a pre-formed bend that extends at a non-zero angle relative to a longitudinal axis of the second catheter when the second distal end portion is extended through the adapter.

In some embodiments the suction tube is constructed so that the distal end would be round and a-traumatic, and pre-curved to ease the insertion process into the airway system. The outer side of the curved tube may be marked so that the operator can orient it appropriately when inserted.

In some embodiments the suction tube can be marked along the entire length to indicate how deep the distal end is inserted. In addition, the suction tubes are marked on the proximal part protruding from the tracheal tube (when the distal end of the large and smaller tubes are aligned) every 1 cm with a line around the tube.

In some embodiments the suction tubes' distal ends are visible under X-Ray, with the marker band secured to the distal end.

In some embodiments the suction tube is constructed of two or more lumens, one main lumen for suction and a secondary for therapeutic agent infusion. The catheter is dual lumen; the primary lumen may be used to aspirate mucus from the lungs. Because the catheter can be keyed, the catheter form represents a novel device as it can access entire either main branch of the bronchi and aspirate mucus. The second lumen can be used to introduce saline and perform lavage. The second lumen can also be used to introduce a multitude of medications. In conjunction with aspiration the ability to medicate after aspiration assures the medication interfaces with tissue rather than sitting on mucus providing little benefit to the patient. Thus, this invention can be a multitude of devices, to be used for the following procedures:

Aspiration
Lavage
Aspiration with Lavage
Aspiration in conjunction with a drug delivery system
Aspiration, lavage and drug delivery In some embodiments the suction tube main is constructed so that the distal end would be round and a-traumatic, and the proximal end connected to a suction type connector.

In some embodiments the suction tube secondary is constructed so that the distal end is skived open, rounded and a-traumatic. In this case, the inflation port may pass through a y-piece and the proximal end thermally formed to be sealed near the suction connector.

In some embodiments the suction tubes are keyed inside the tracheal tube to control the orientation of the curved distal ends, and ensure that the two distal ends of the suction tubes will be pointed inside the tracheal tube to form a Y shape.

In some embodiments the suction tubes are pre-formed to enable retraction into the tracheal tube and blind deployment into the pre-formed curved form, confirming the two distal ends of the suction tubes will point in opposite directions inside the tracheal tube to form a Y shape.

In some embodiments, the above catheter system comprises a closed system suction catheter assembly including the above described suction catheter, a ventilation adapter that can be attached to the proximal end of an endotracheal tube using a fitting connected between the end of a tracheal tube and a ventilation circuit. The above aspiration catheter can be advanced through the forward coupling down the tracheal tube to enable suctioning. A flexible envelope extends between the two couplings, enclosing the catheter so that it can be manipulated through the envelope. A wiper seal in the forward coupling prevents gas from the ventilation system inflating the envelope.

In some embodiments the closed system suction catheter assembly is used to remove secretions from within the trachea or bronchi of an intubated patient. The assembly comprises a flexible catheter connected at its distal end to the proximal end of an endotracheal tube. The proximal end of the flexible catheter may be connected with a fitting, including a valve that can be opened or closed, to control the application of suction to the catheter.

In some embodiments, provision is made for cleaning the catheter after its distal end has been withdrawn into the forward coupling. A manually-operable valve is located forwardly of the wiper seal providing a cleaning chamber between the valve and the wiper seal. An irrigation port opens into this chamber so that saline can be supplied to it, which is then drawn along the bore of the catheter by the applied suction to remove matter collected within the bore.

Methods for using catheter systems according to embodiments described herein are also provided. FIG. 1 shows a catheter system 100 according to an embodiment. The system 100 includes an elongated body 102 having a proximal end 104 and a distal end 106, and a lumen 108 extending between the proximal end 104 and distal end 106. Within the lumen 108 is a first inner catheter 116 having a proximal end 120 and a distal end 122. A second inner catheter 117 may also be provided within the lumen 108, the second inner catheter having a proximal end 121 and a distal end 123. The inner catheters 116, 117 may emerge from one or both of the proximal and distal ends 104, 106 of the elongated body 102. The elongated body 102 may be formed of a flexible envelope 140, which may enable a user of the system 100 to manipulate one or both of the inner catheters 116, 117 with the user's hands through the flexible envelope 140. Thereby, the user may extend adjust the position or extend one or both the inner catheters 116, 117 into a body of a patient.

The distal end 106 of the elongated body 102 may include a ventilation adapter portion 112 that may be provided with a fitting 138 to connect the system 100 to, for example, an endotracheal tube 114 or some other member. The first and second inner catheters 116, 117 may extend out through the ventilation adapter portion 112 and through an attached member, such as the endotracheal tube 114, to emerge from an opposite end of the endotracheal tube 114 positioned within a body of a patient. Additionally, the fitting 138 may be rotatable relative to the elongated body 102. The ventilation adapter portion 112 may also include a ventilation adapter 154 for providing ventilation to the patient.

The first and second inner catheters 116 and 117 may be provided with connector portions 136 and 137, respectively, on the proximal ends 120, 121. The connector portions 136, 137 may each include a wiper seal 142 to prevent leakage when the connector portions 136, 137 are connected to, for example, a source of a fluid. The connector portions 136, 137 may each also include a valve 146 and an irrigation port 152. In the embodiment shown in FIG. 1, the valve 146 is a manually operated valve, but other embodiments are also possible.

The distal end 122 of the first inner catheter 116 may have a bend 128. The distal end 123 of the second inner catheter 117 also may have a bend 129. The bends 128 and 129 may curve in opposite directions to create a V- or Y-shape formed by the first and second inner catheters 116, 117.

Figure 2A:
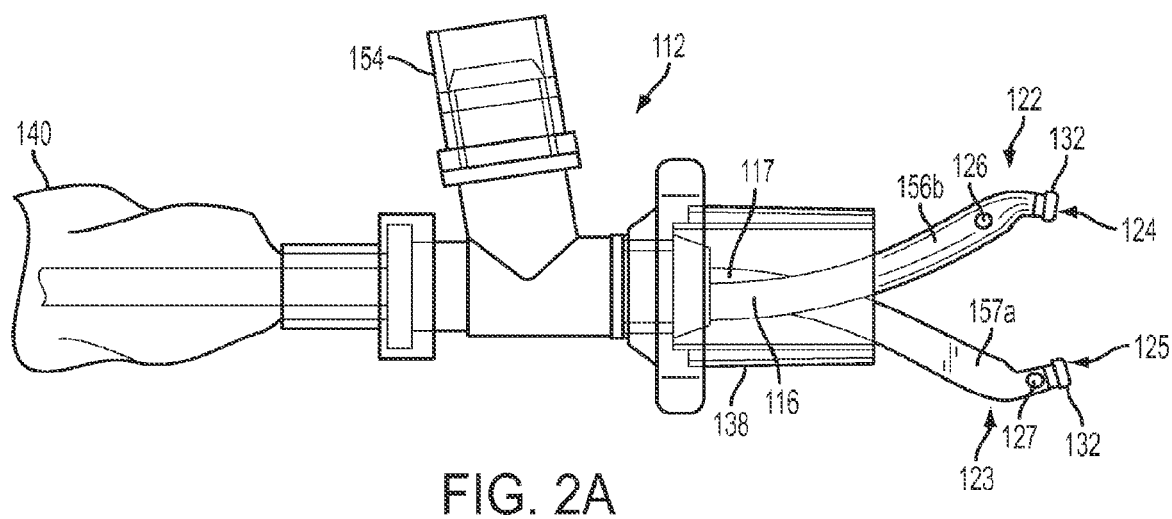
FIG. 2A shows a close-up side view of the connection portion of the catheter system shown in FIG. 1 that connects to the endotracheal tube in an embodiment of the present invention.

FIG. 2A shows a close-up view of the ventilation adapter portion 112 with no endotracheal tube connected to the fitting 138. The ventilation adapter portion 112 may include a key joint component (discussed below) that forms a keyed joint with one or both inner catheters 116, 117. The keyed joint may, for example, rotationally fix the inner catheters 116, 117 with respect to the ventilation adapter portion 112. In the embodiment shown in FIG. 2A, the inner catheters 116, 117 are fixed such that the first inner catheter 116 curves in the same direction as the direction in which the ventilation adapter 154 points. As such, the ventilation adapter 154 may serve as an indicator to a user of the orientation of the distal ends 122, 123 of the inner catheters. However, other configurations are possible. For example, the orientation of the inner catheters may be indicated by some other feature provided on the catheter system 100.

The shape of the inner catheters 116, 117 may be a D-shape, with one side of the catheter curved, and the other side flat. FIG. 2A shows the curved side 156b of the first inner catheter 116 and the flat side 157a of the second inner catheter 117. In the configuration shown, the flat sides 156a (not shown) and 157a face each other. The shapes and orientations of the inner catheters are not limited to this configuration as other shapes and orientations may be provided in accordance with the principles of the invention. In embodiments where the catheters have differently shaped cross-sections, the catheters may still have cross-sections with flat sides that face each other, thereby allowing the catheters to be in close proximity and minimizing the volume occupied by the catheters. However, the catheters may have still other cross-sectional shapes, and the facing sides may not be flat, but may have sides that nonetheless correspond with one another. Additionally, the cross-section of the catheter may not be constant across the entire length of the catheter. For example, FIG. 3B shows a circular opening of the lumens 124, 125 on the distal ends of the inner catheters 116, 117, while the catheters nonetheless have a D-shaped cross-section over a remaining portion of the catheters that are shown.

The first inner catheter 116 has a primary lumen 124. A secondary lumen 126 may also be provided within the first inner catheter 116. When a second inner catheter 117 is provided, it has a primary lumen 125, and may also have a secondary lumen 127. The numbers of lumen in the inner catheters 116, 117 is not limited to these configurations, and more lumens may be provided.

The inner catheters 116, 117 may also be provided with a-traumatic ends 132 that are curved or folded back to be less traumatic to surfaces inside the patient. Openings to the primary lumens 124, 125 of the first and second inner catheters 116, 117 may be formed on these a-traumatic ends 132. Additionally, secondary lumens 126, 127 may open on a side of the inner catheters 116, 117, respectively.

Figure 2B:
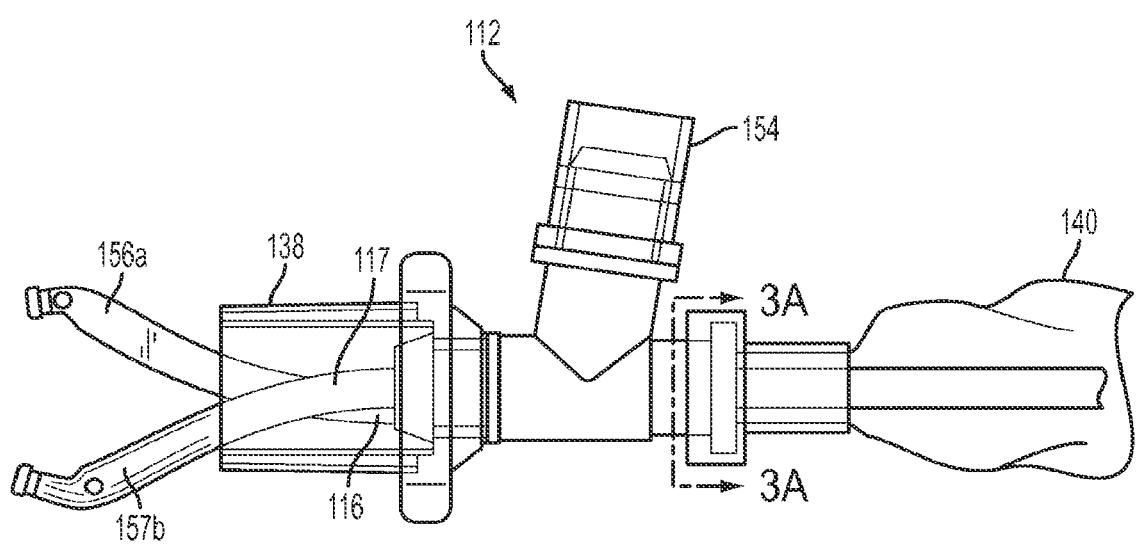
FIG. 2B shows an opposite side view of the connection portion shown in FIG. 2A in an embodiment of the present invention.

FIG. 2B shows an opposite-side view of the ventilation adapter portion 112 shown in FIG. 2A. The flat side 156a of the first inner catheter 116 and the curved side 157b of the second inner catheter 117 can be seen in FIG. 2A.

Figure 2C:
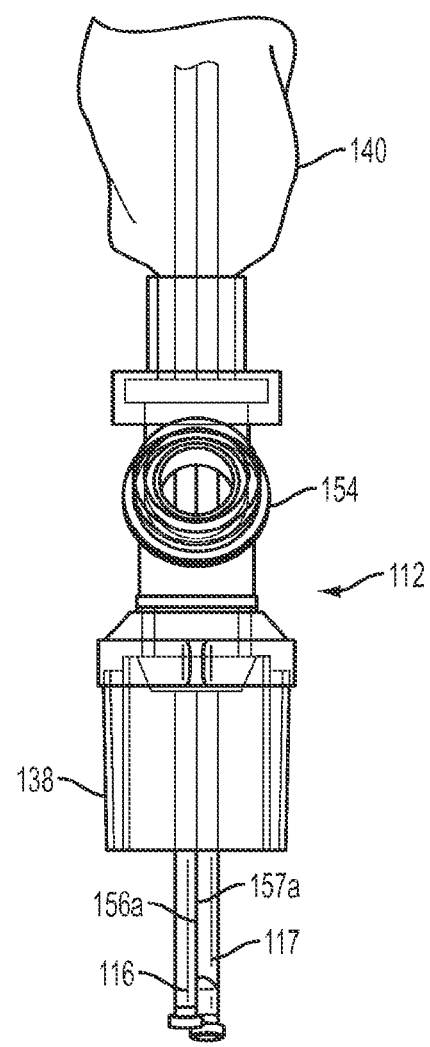
FIG. 2C shows a top view of the connection portion shown in FIG. 2A in an embodiment of the present invention.
Figure 2D:
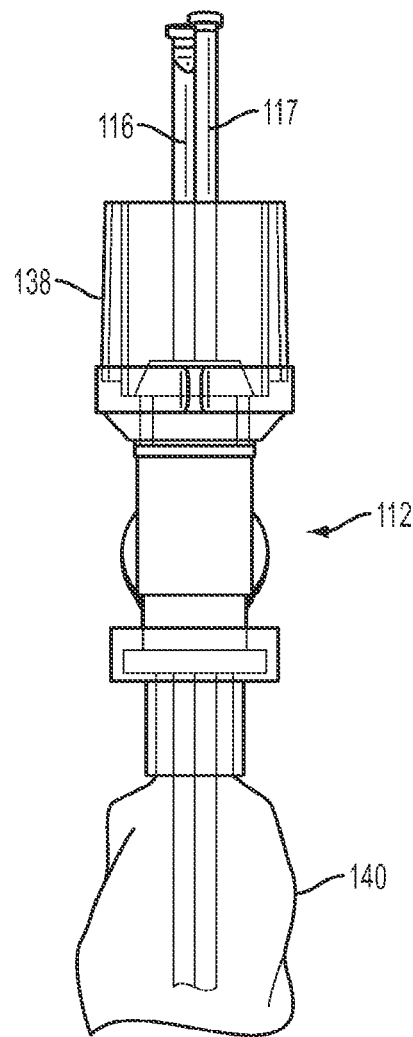
FIG. 2D shows a bottom view of the connection portion shown in FIG. 2A in an embodiment of the present invention.

FIG. 2C shows a top view of the ventilation adapter portion 112 looking down onto the ventilation adapter 154. The inner catheters 116, 117 may be arranged such that the flat sides 156a and 157a are facing and proximate to each other. As mentioned above, the shapes of the inner catheters are not limited to a D-shape, and other shapes may have different shaped surfaces that face and/or contact one another. FIG. 2D shows a bottom view of the ventilation adapter portion 112.

FIG. 3A shows a sectional view of a portion of the ventilation adapter portion 112, the sectional view being coaxial with the ventilation adapter portion 112 and from the section line 3A shown in FIG. 2B. FIG. 3B shows the same portion from an isometric, side perspective. The key joint component 110 is disposed within the ventilation adapter portion 112. In the embodiment shown in FIGS. 3A and 3B, the key joint component 110 is keyed for first and second inner catheters 116, 117. A key joint fitting 158 may be provided between the key joint component 110 and the ventilation adapter portion 112. The key joint fitting 158 may, for example, help secure the key joint component 110 within the ventilation adapter portion 112.

Figure 4A:
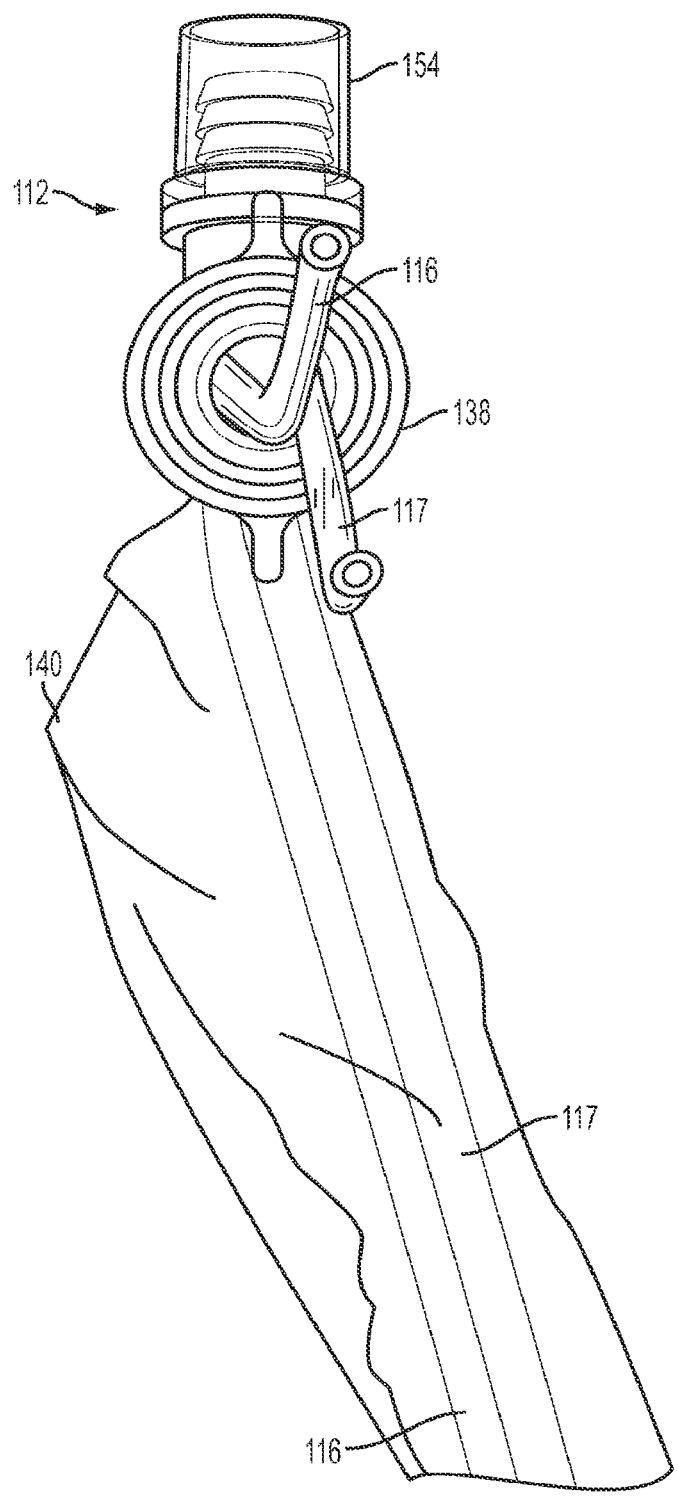
FIG. 4A shows another perspective view of the catheter system shown in FIG. 3B in an embodiment of the present invention.
Figure 4B:
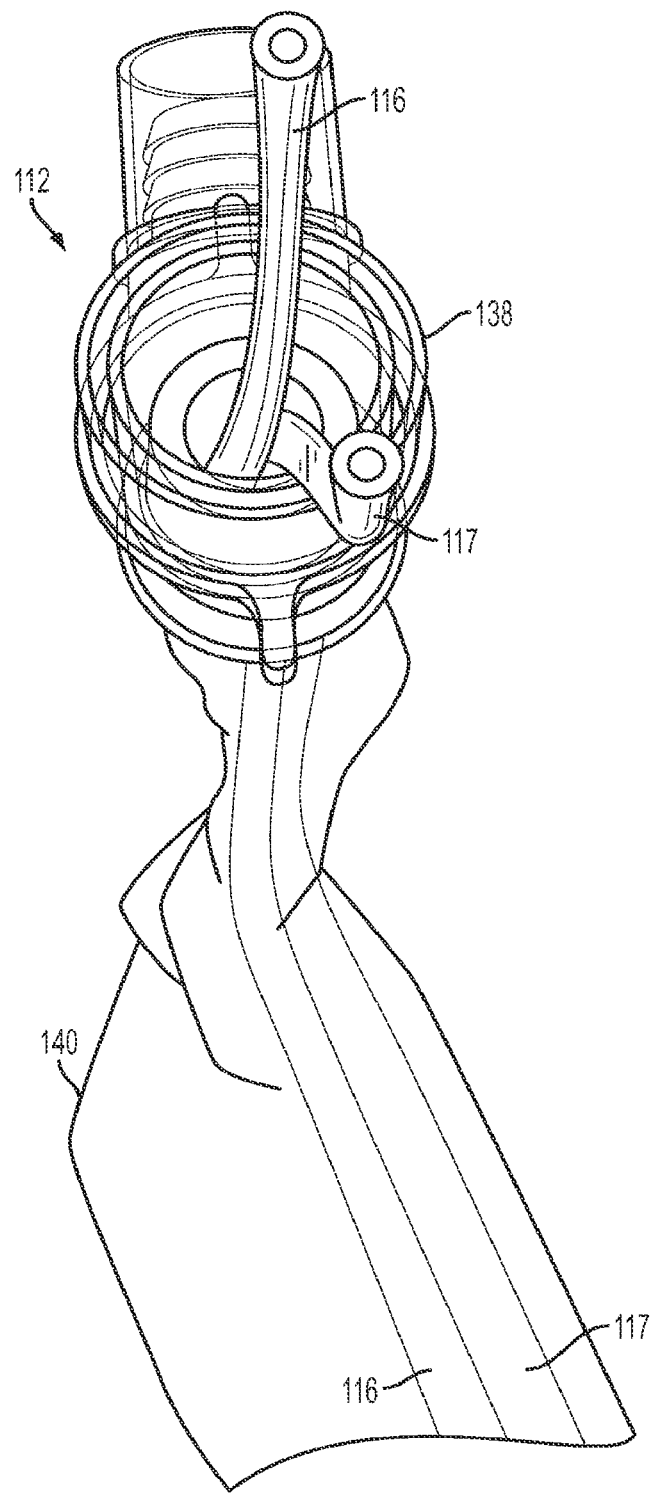
FIG. 4B shows another perspective of the catheter system shown in FIG. 4A in an embodiment of the present invention.

FIG. 4A a view that is coaxial with the fitting 138 of the ventilation adapter portion 112. FIG. 4B is an alternative perspective of the portion shown in FIG. 4A.

Figure 5:
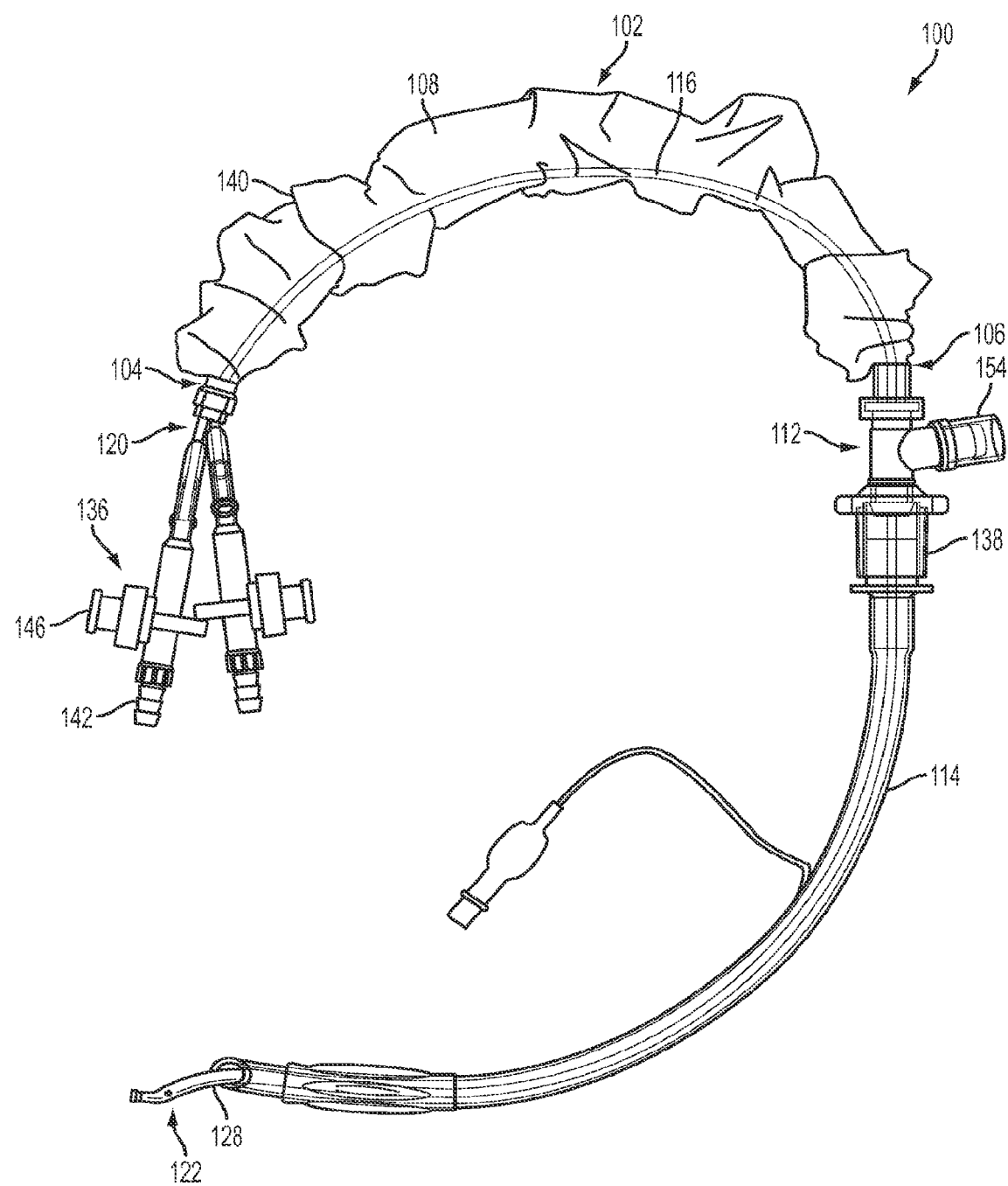
FIG. 5 shows a side view of an endotracheal tube connected to a catheter system having a single internal catheter within a first catheter in an embodiment of the present invention.
Figure 6A:
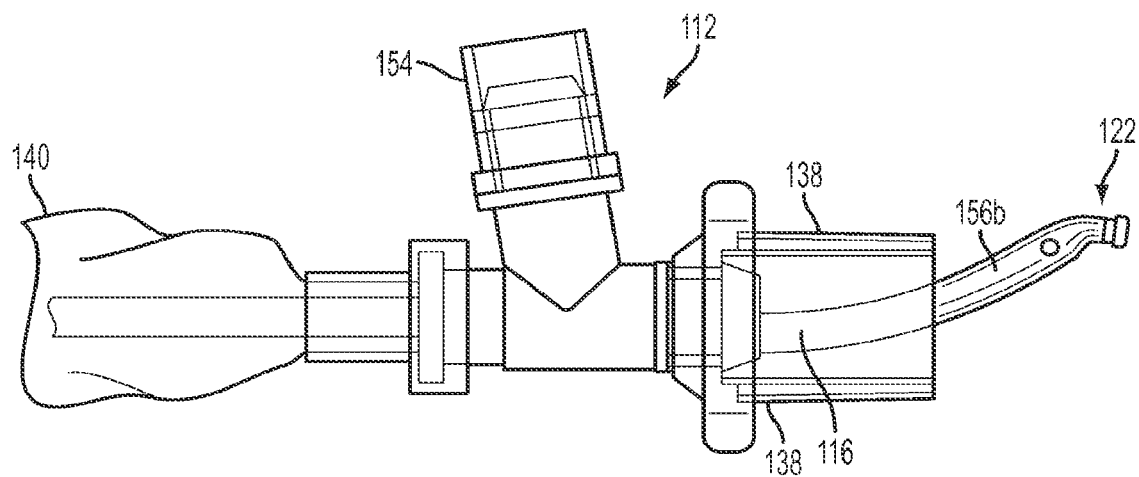
FIG. 6A shows a close-up side view of the connection portion of the catheter system shown in FIG. 5 that connects to the endotracheal tube in an embodiment of the present invention.
Figure 6B:
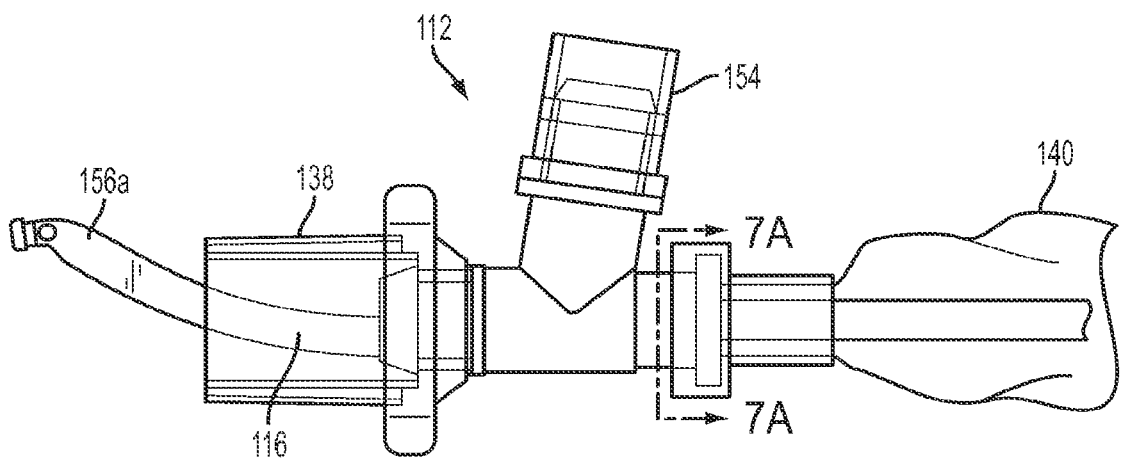
FIG. 6B shows an opposite side view of the connection portion shown in FIG. 6A in an embodiment of the present invention.
Figure 6C:
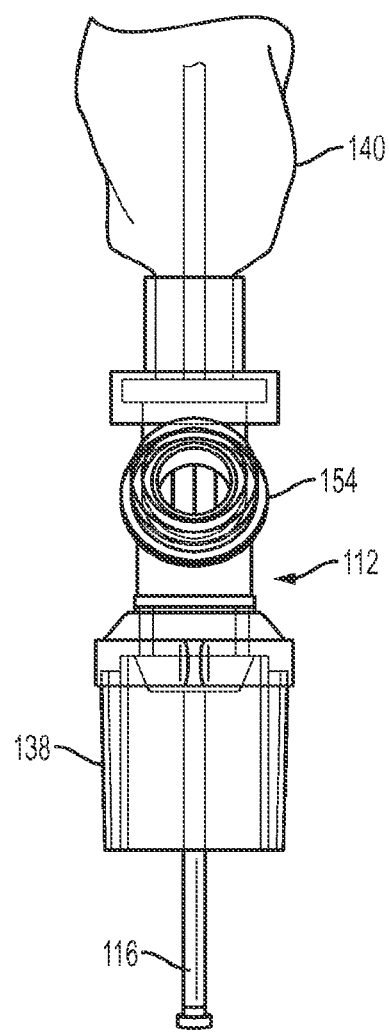
FIG. 6C shows a top view of the connection portion shown in FIG. 6A in an embodiment of the present invention.
Figure 6D:
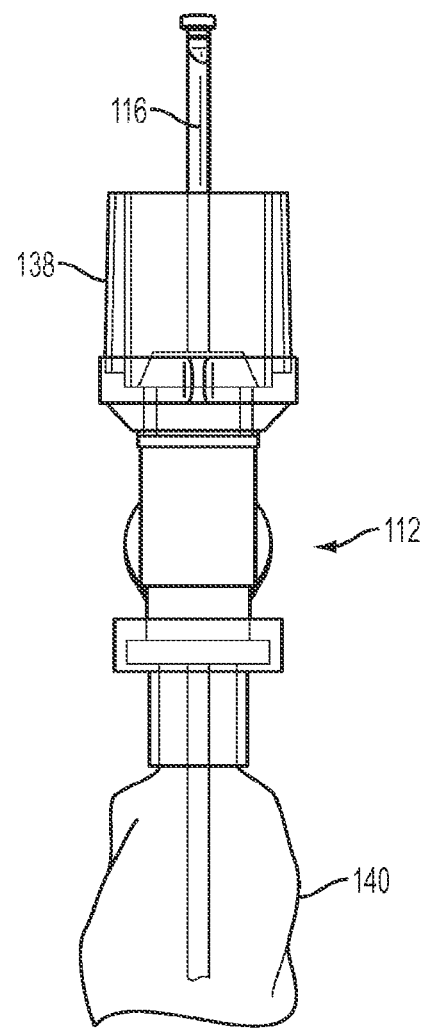
FIG. 6D shows a bottom view of the connection portion shown in FIG. 6A in an embodiment of the present invention.

FIG. 5 shows the catheter system 100 according to an embodiment in which only a single catheter (e.g., first inner catheter 116) is disposed within the system. Except for the exclusion of a second inner catheter, the parts of the system shown in FIG. 5 are identical to those in FIG. 1, and descriptions of those parts will not be repeated here.

The catheter systems described herein may be utilized as a single catheter and/or a double catheter. The catheters can be independently movable proximally and distally. The double catheters can be independently moveable so that they can each move independently from the other proximally and distally to reach different locations. Each can be removed, replaced, and reinserted independently from the other, as well.

FIGS. 6A-6D show views of a single catheter embodiment similar to the views of the double catheter embodiment shown in FIGS. 2A-2D. Features that were previously discussed will not be repeated here.

Figure 7B:
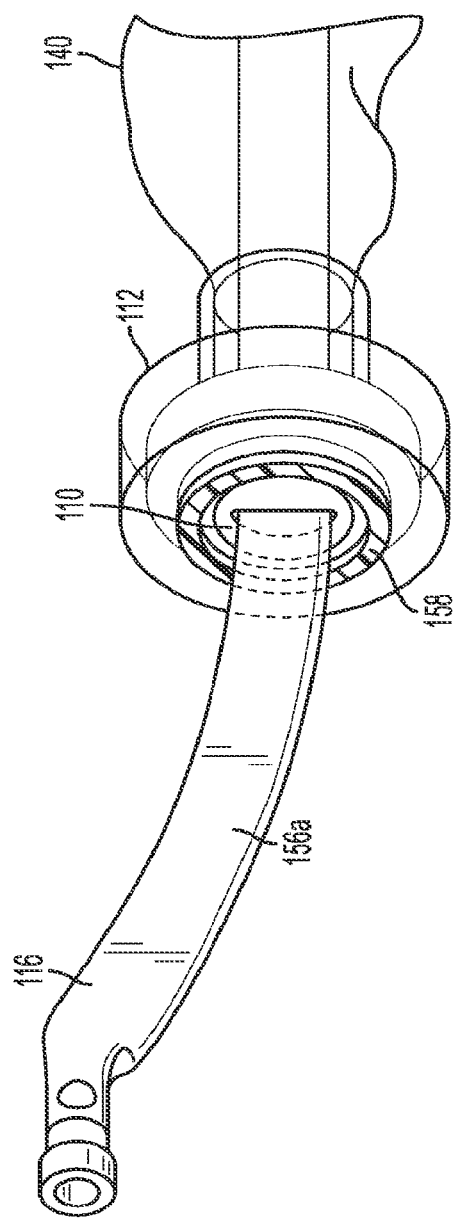
FIG. 7B shows a side perspective view of the connection portion with the second catheter extending from the key joint component of the first catheter in an embodiment of the present invention.
Figure 7A:
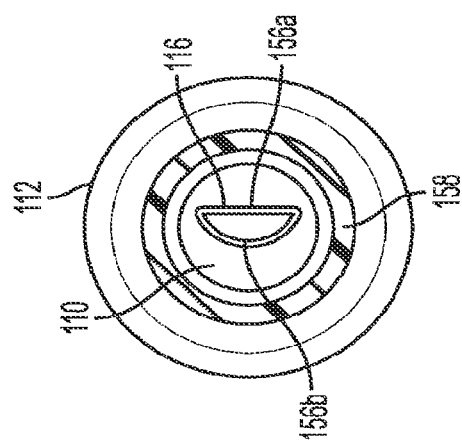
FIG. 7A shows a cross-section view, according to the broken line in FIG. 6B, of the connection portion with a key joint component of a first catheter and a second catheter forming a keyed joint with the key joint component of the first catheter in an embodiment of the present invention.
Figure 8A:
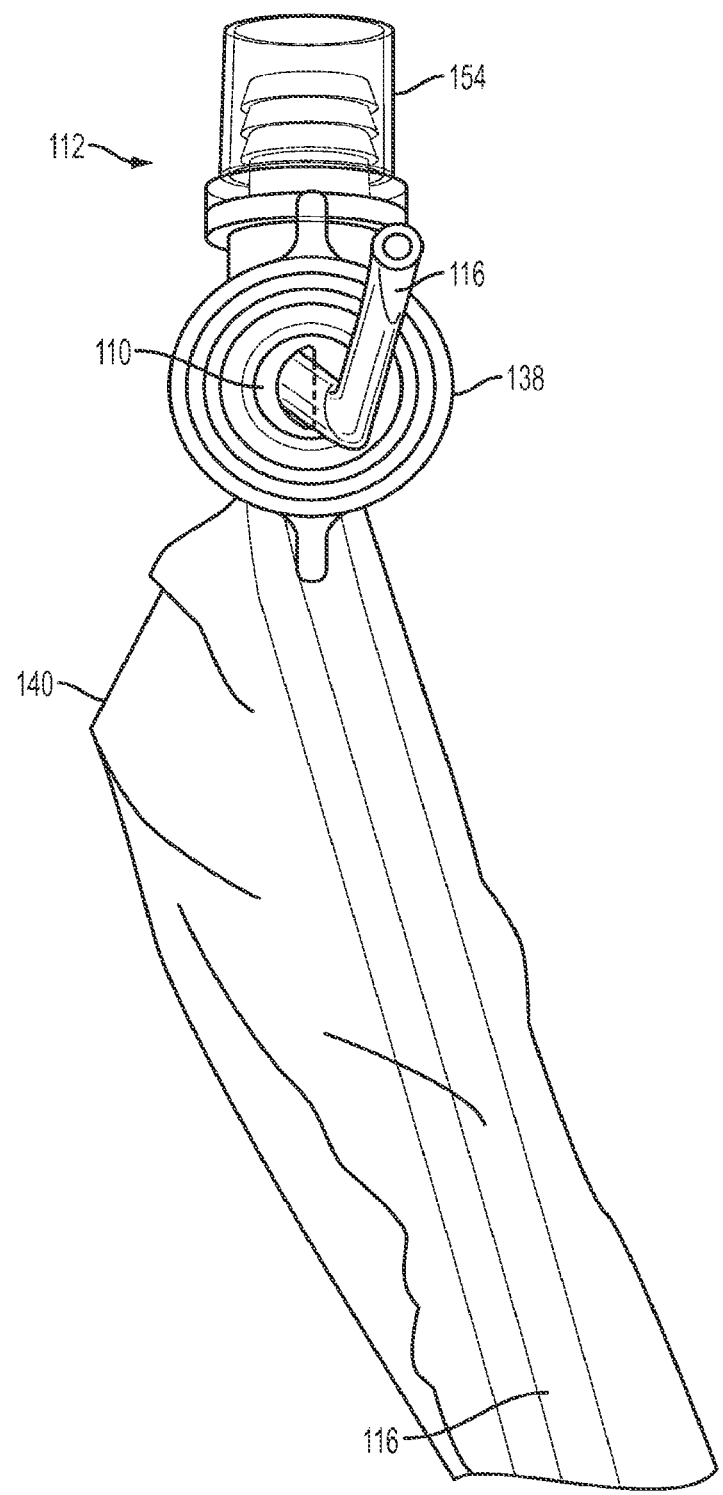
FIG. 8A shows another perspective view of the catheter system shown in FIG. 7B in an embodiment of the present invention.
Figure 8B:
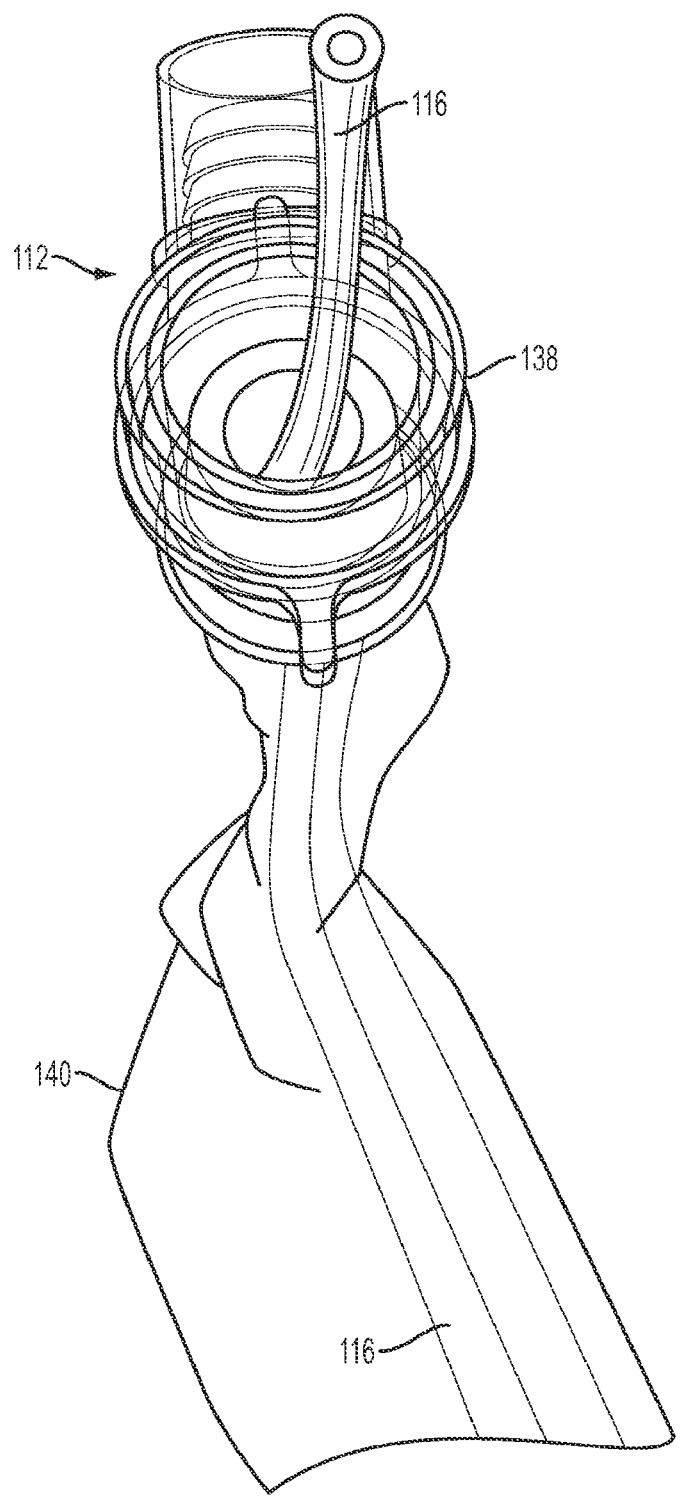
FIG. 8B shows another perspective view of the catheter system shown in FIG. 7B in an embodiment of the present invention.

FIGS. 7A and 7B show views of a single catheter embodiment with a key joint component 110 that is keyed only for a single inner catheter 116 according to the single catheter embodiment. Embodiments with a single catheter 116 are also shown in FIGS. 8A and 8B.

Figure 9A:
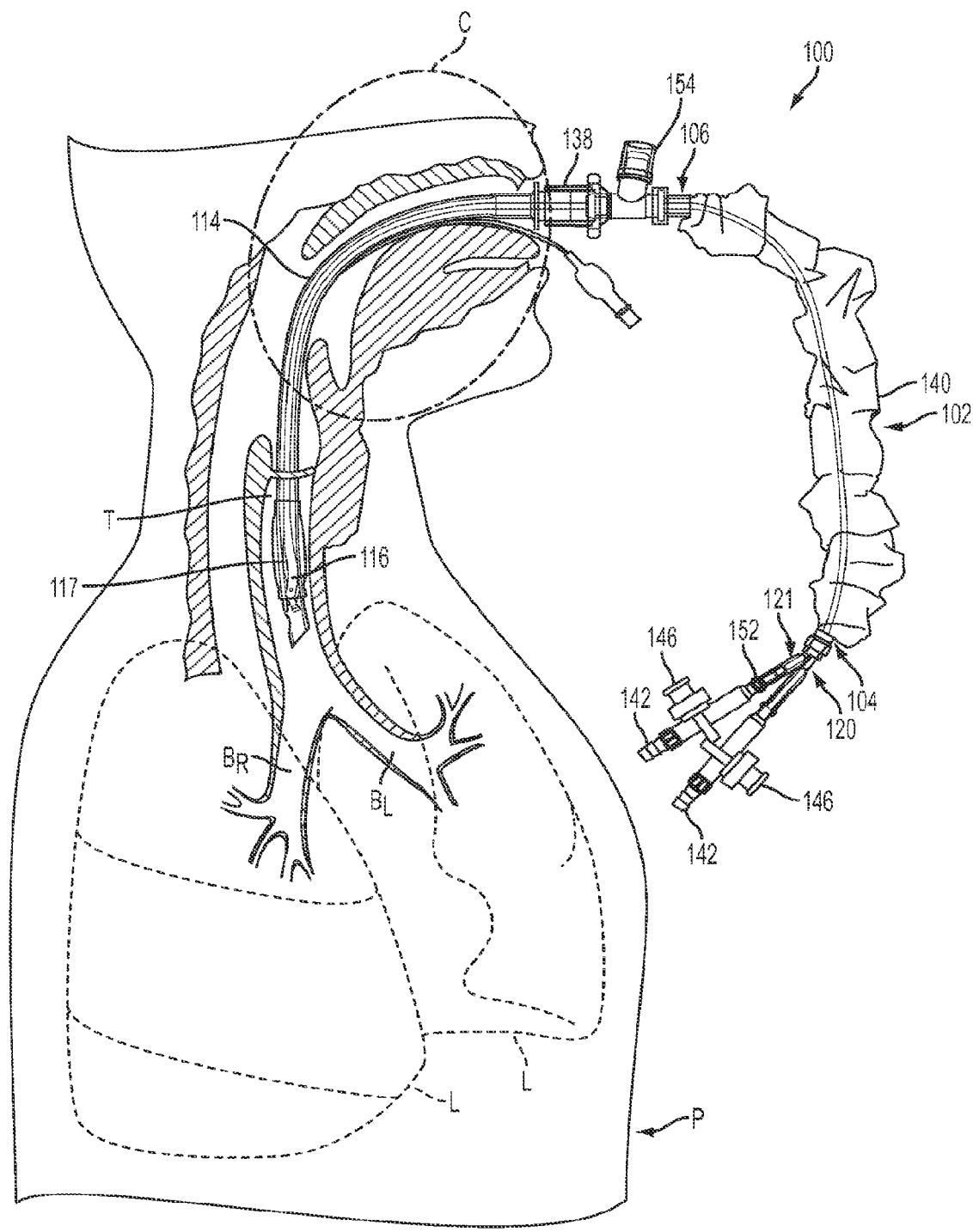
FIG. 9A shows a catheter system with an endotracheal tube disposed within a patient prior to inner catheters being extended from the endotracheal tube in an embodiment of the present invention.
Figure 9B:
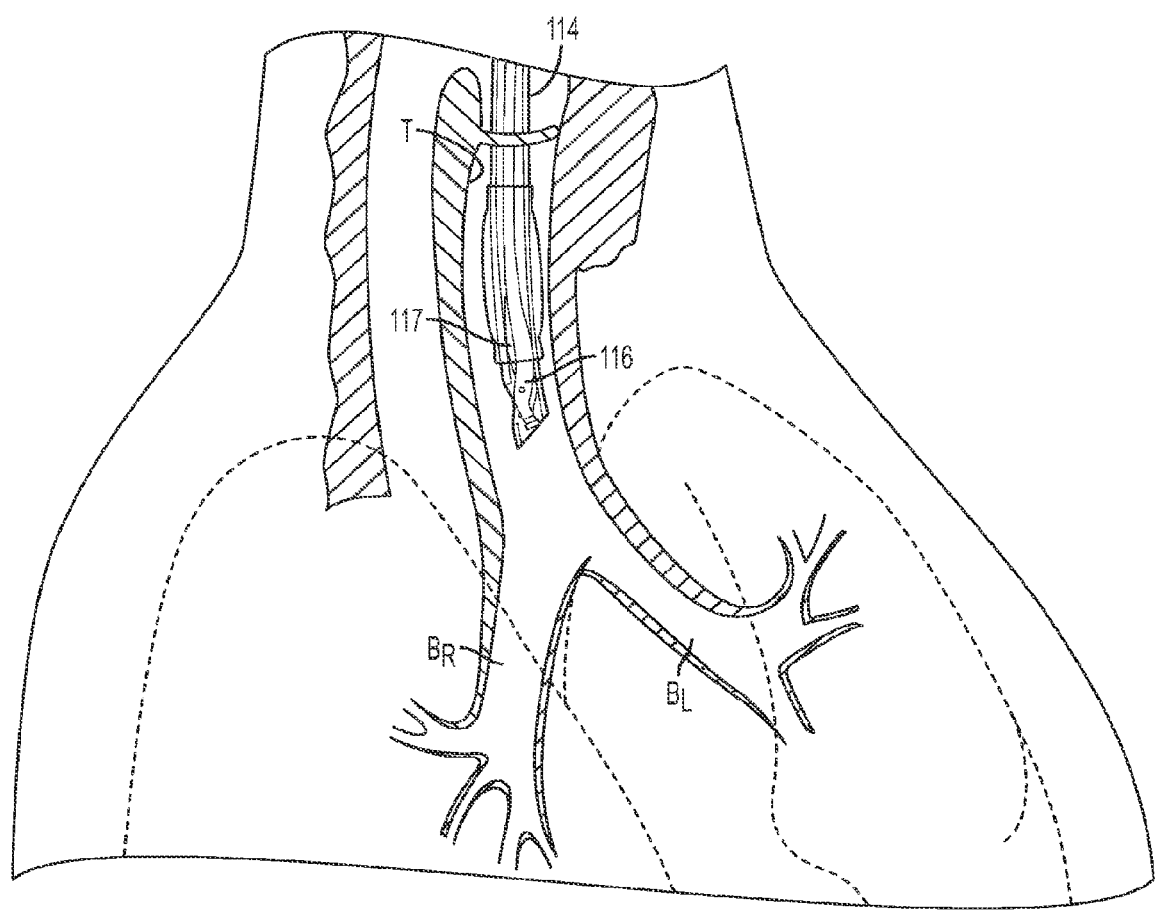
FIG. 9B shows a close-up view of the end of the endotracheal tube shown in FIG. 9A as the inner catheters are about to emerge from the endotracheal tube in an embodiment of the present invention, and reliably passing by the Murphy's eye in the endotracheal tube.
Figure 9C:
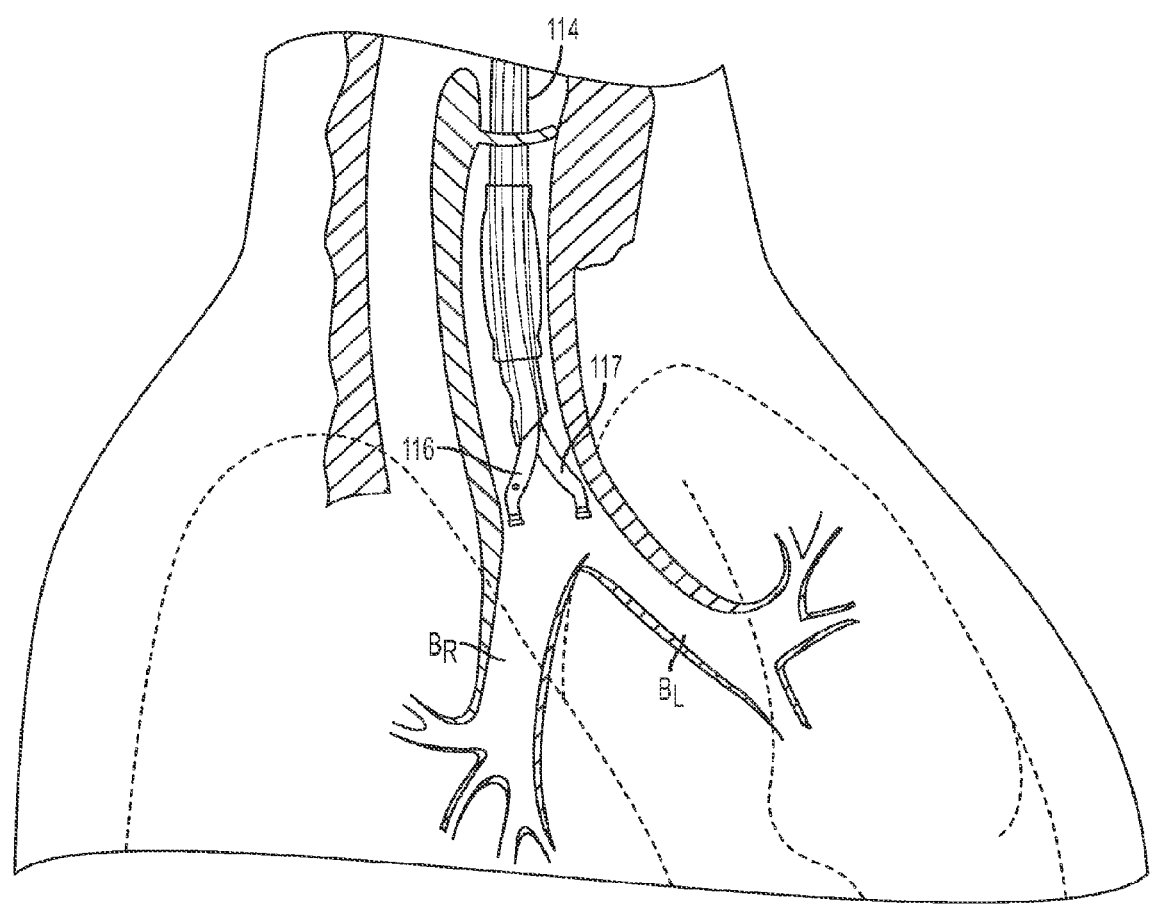
FIG. 9C shows a close-up view of the system shown in FIG. 9A after the inner catheters have emerged from the endotracheal tube in an embodiment of the present invention.
Figure 9D:
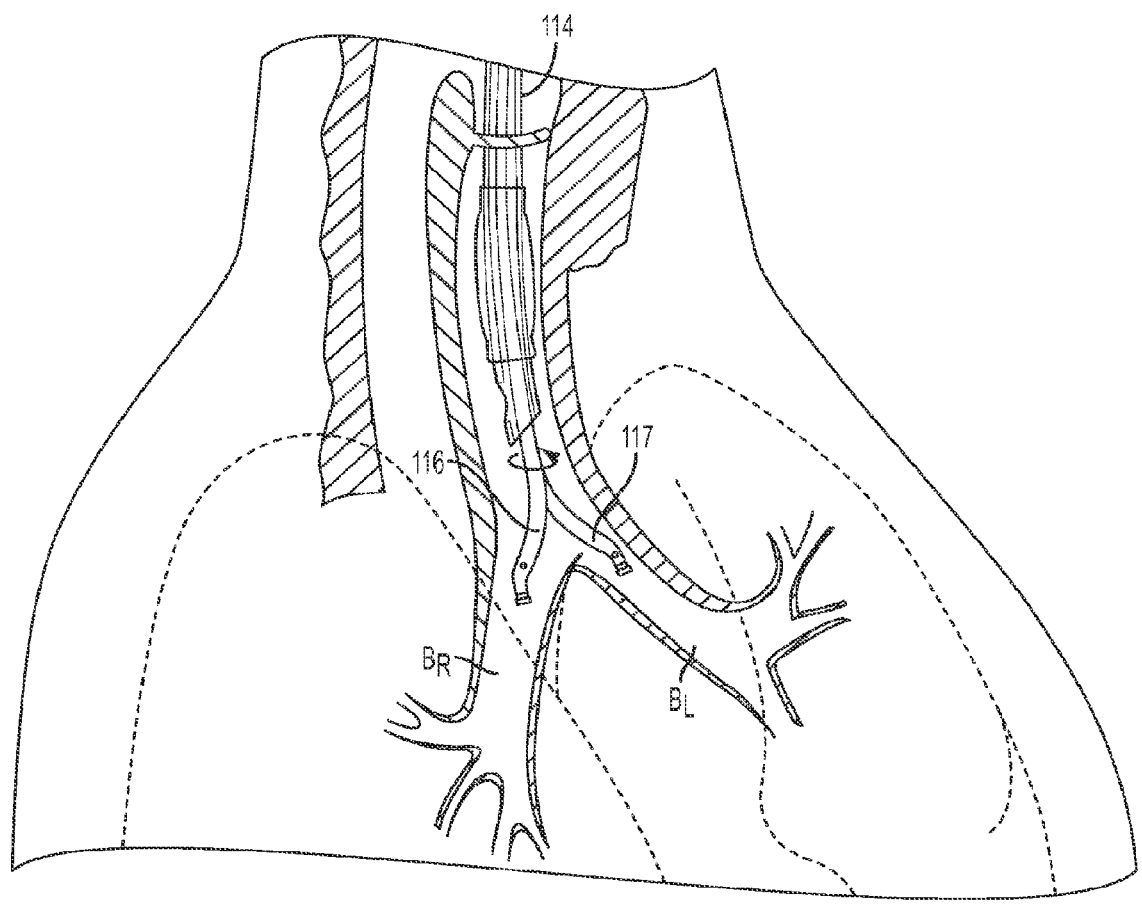
FIG. 9D shows a close-up view of the system shown in FIG. 9A after the inner catheters have extended farther than the position shown in FIG. 9C in an embodiment of the present invention where the placement can be accomplished by a push/pull positioning alone, and/or in combination with rotation of the pair of catheters as shown by a rotational arrow.
Figure 9E:
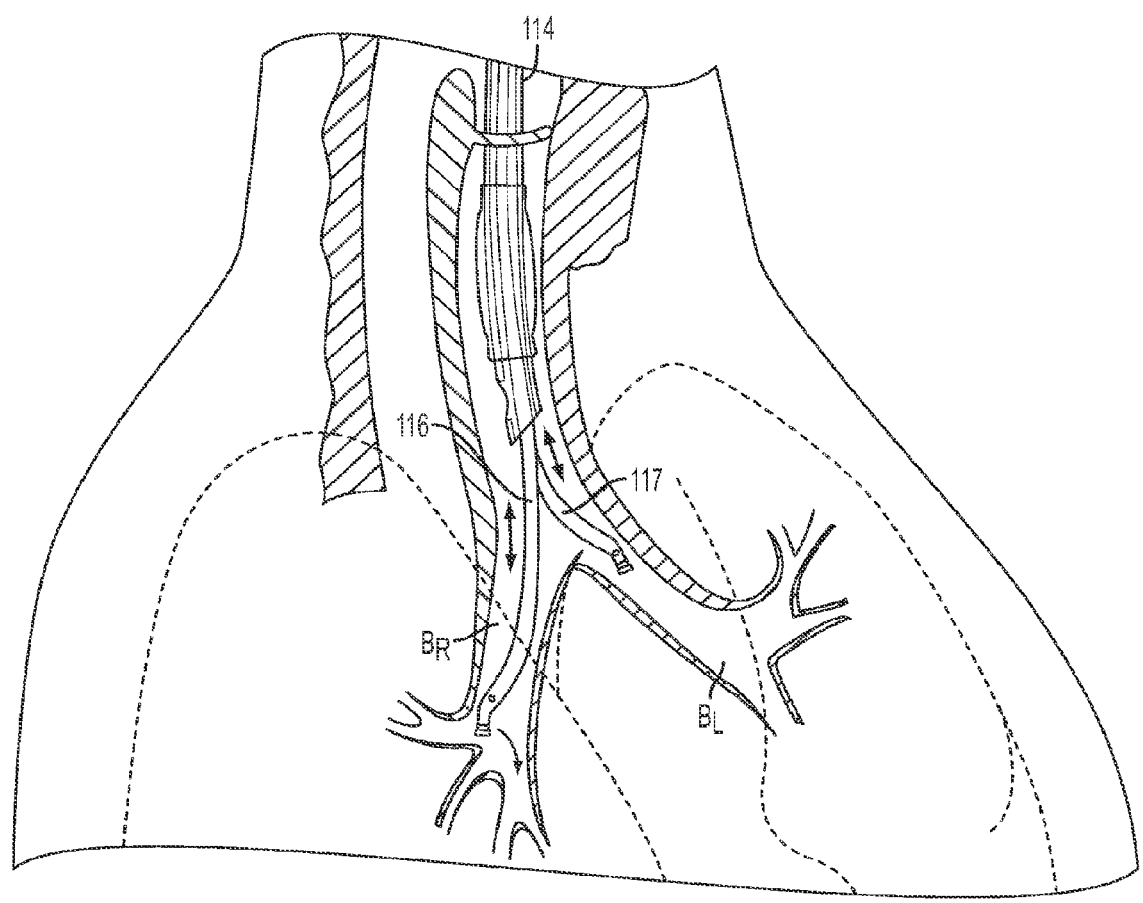
FIG. 9E shows a close-up view of the system shown in FIG. 9A after one of the inner catheters has extended farther than the position shown in FIG. 9D, the directional arrow indicating that the catheters are independent and separately moveable to target separate areas or lumens in an embodiment of the present invention.

An embodiment of the catheter system 100 having two catheters is shown in FIGS. 9A-9E with the inner catheters 116, 117 in various stages of deployment from the endotracheal tube 114. To illustrate the positioning of the catheter system 100, the lungs L of patient P are also shown with the left bronchus $B_L$ and right bronchus $B_R$. In FIG. 9A, the catheter system 100 is shown attached to an endotracheal tube 114 that is inserted into the trachea T of the patient P. The first and second inner catheters 116, 117 are shown within the endotracheal tube 114. FIG. 9B shows a close-up view of the endotracheal tube 114 disposed near the left and right bronchi $B_L$ and $B_R$. The distal ends of the inner catheters 116, 117 have been positioned near the opening at the end of the endotracheal tube 114. As an operator of the catheter system 100 pushes the inner catheters 116, 117 further past the distal end 106 of the elongated body 102 (see FIG. 9A), the inner catheters emerge from the endotracheal tube 114, as shown in FIG. 9C. As discussed above, the inner catheters 116, 117 may be shaped to form a V- or Y-shape as they emerge from the confines of the endotracheal tube 114. This shape can position the inner catheters 116, 117 to correspond to the branches of the left and right bronchi $B_L$ and $B_R$ such that one or both of the inner catheters may be easily positioned into one or both bronchi. For example, FIG. 9D shows the inner catheters 116, 117 after being further pushed through the endotracheal tube 114. The first inner catheter 116 extends toward and into the right bronchus $B_R$ and the second inner catheter 117 extends toward and into the left bronchus $B_L$. One or both inner catheters 116, 117 may be pushed even farther into the lungs to reach various branches within the lungs. For example, FIG. 9E shows the first inner catheter 116 positioned farther into the right bronchus $B_R$.

The inner catheters 116, 117 can also be rotated while inserted into the patient, as indicated by the circular arrow in FIG. 9D. This rotation can be achieved by the operator of the catheter system 100 rotating the portion of the inner catheter on the exterior of the patient. This rotation can be used to facilitate insertion of the inner catheters into the bronchi. However, in some embodiments, rotation of inner catheters 116, 117 may not be needed because the inner catheters 116, 117 may already be in desired positions. For example, due to the form or curvature of the inner catheters 116, 117, they may each be directed to different bronchi such that one may be used for one bronchus, and the other for the other bronchus without requiring a rotation. As indicated by the arrows in FIG. 9E, the inner catheters can each target smaller lumens within one or both of the bronchi.

Figure 9F:
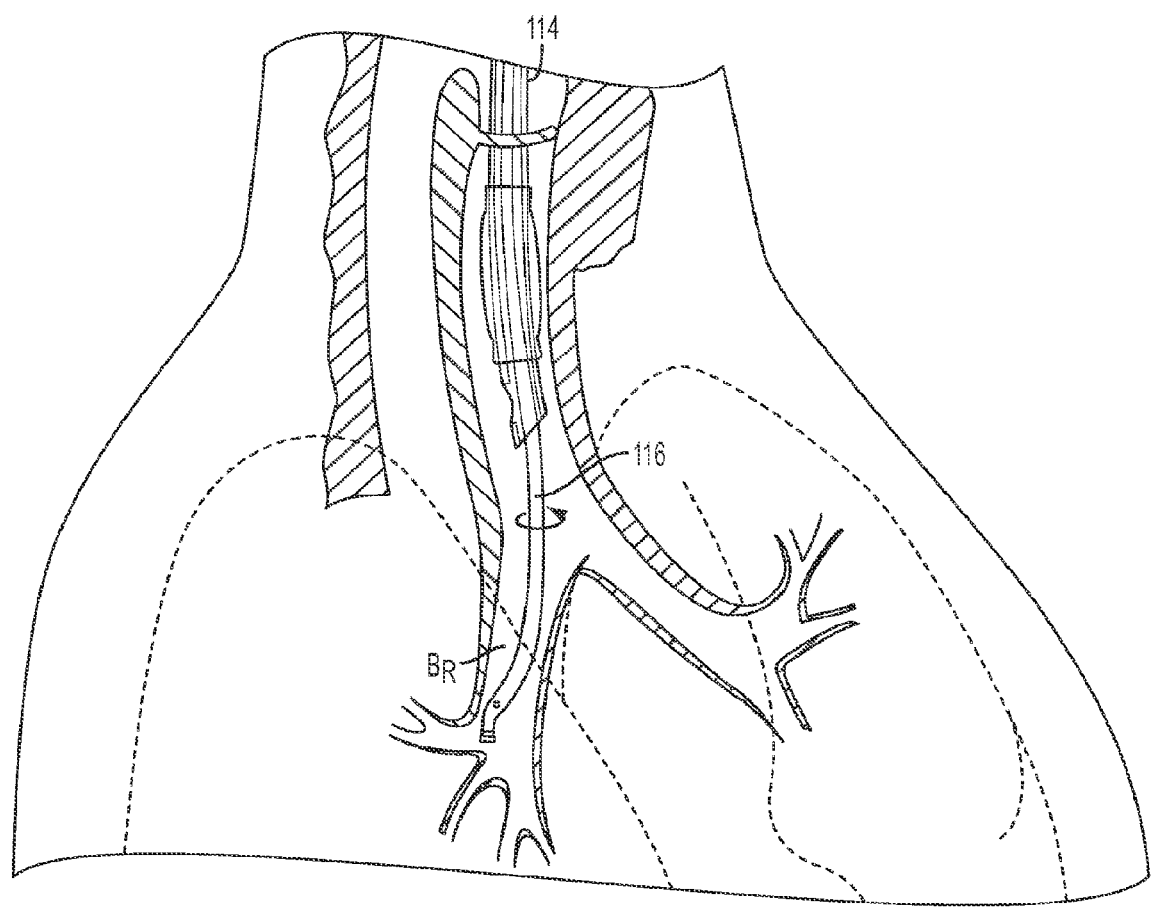
FIG. 9F shows a catheter system with only a single inner catheter extending out of the endotracheal tube which can indicate that the second catheter was removed and can be reintroduced and/or the single catheter can be delivered as a single catheter in an embodiment of the present invention.

FIG. 9F shows an example of the single catheter embodiment of the catheter system 100. The inner catheter 116 is shown inserted into the right bronchus $B_R$, but the inner catheter 116 could also be positioned into the left bronchus $B_L$.

Figure 10:
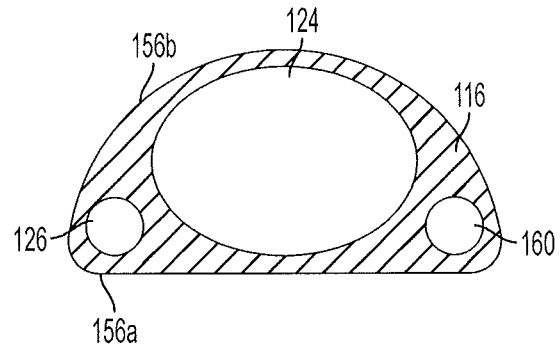
FIG. 10 shows a cross-section of an inner catheter in an embodiment of the present invention.

A cross-section of an embodiment of an inner catheter 116 is shown in FIG. 10. In this embodiment, the catheter 116 has a D-shaped cross-section, having a curved side 156b and a flat side 156a. The catheter 116 has a primary lumen 124. The catheter 116 may also include a secondary lumen 126 and a tertiary lumen 160. In some embodiments, the primary lumen 124 can be used to perform suction, and the secondary and tertiary lumens 126, 160 can be used for therapeutic agent infusion, including lavage or medicinal delivery. The catheter is not limited to this configuration and may have a differently shaped cross-section or more or fewer lumens.

The primary lumen 124 may be constructed such that the distal end can be rounded and a-traumatic, and the proximal end may be connected to a suction type connector. The secondary and tertiary lumens 126, 160 may be constructed so that the distal end can be skived open, rounded, and a-traumatic. An inflation port could be included through a y-piece and the proximal end thermally formed to be sealed near the suction connector.

According to some embodiments, the cross section of the inner catheter 116 may be based on an extruded polymer shaped like the letter "D" and may have an oval primary lumen 124 to allow mucus aspiration and two round secondary and tertiary lumens 126, 160 on each side to give symmetry to the design, as well as contributing to the torqueability of the cross section in some embodiments.

The "D" shape may be used as a key inside a ventilator adapter and will allow flexibility of the catheter around one axis of the cross section and the stiffness to maintain the shaped distal end on the other axis of the cross section. The dimensions of the D shape according to an embodiment are around 10 mm high and 5 mm width with a minimum oval lumen of 4 mm. However, the cross-section in FIG. 10 is an example of an embodiment of the invention. Other cross-section shapes and lumen configurations and dimensions are also possible according to various embodiments.

Figure 11A:
FIG. 11A shows a bottom view of an inner catheter in an embodiment of the present invention.
Figure 11B:
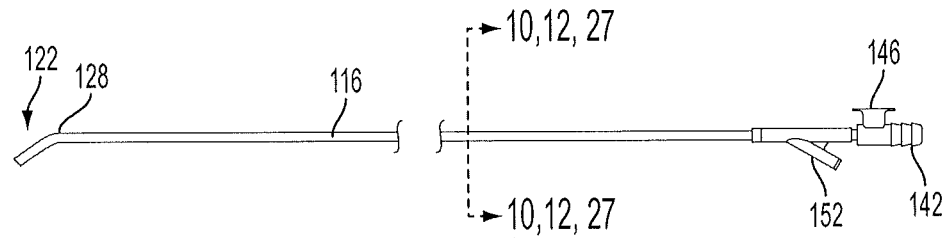
FIG. 11B shows a side view of the inner catheter shown in FIG. 11A in an embodiment of the present invention.
Figure 11C:
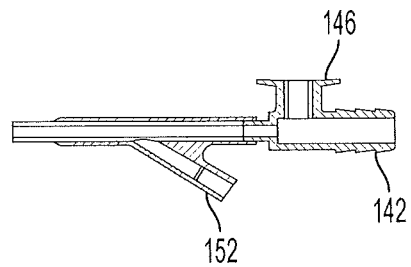
FIG. 11C shows a cross-section detail view of one end of the inner catheter shown in FIG. 11B in an embodiment of the present invention.

An embodiment of an inner catheter 116 without the elongated body 102 is shown in FIGS. 11A and 11B. The catheter of this embodiment includes a curved suction tube (bend 128) with a proximal end suction adapter/valve (having a wiper seal 142) and the Y connector fluid connector (irrigation port 152) for the fluid infusion. The primary lumen 124 may be connected directly to the suction adapter/valve and the secondary and tertiary lumens 126, 160 may be skived and bonded to the Y adapter to create a luer infusion port. FIG. 11A shows a top view of the catheter according to this embodiment. The active length of the catheter of FIG. 11A may be about 24 inches in some embodiments. The lower projection shows the orientation of the J shaped tip and the corresponding orientation of the inflation port at the distal end of the catheter. FIG. 11C shows a close-up cross-section of the proximal end of the inner catheter 116 shown in FIGS. 11A and 11B. As shown in FIG. 11C, the suction adapter/valve is attached to the primary lumen 124 by skiving off the two secondary lumens and bonding the single lumen to the suction adapter/valve. The cross section also shows how the infusion port is attached to the secondary lumen by partially skiving off the two secondary lumens and bonding the Y adapter to attach the irrigation port 152.

Figure 12:
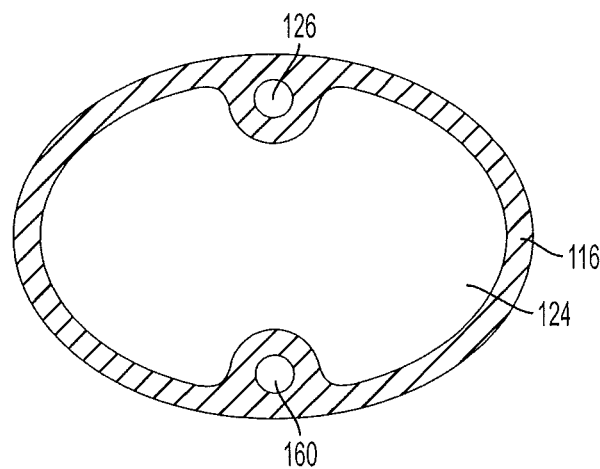
FIG. 12 shows a cross-section of an inner catheter in an embodiment of the present invention.

FIG. 12 shows another embodiment of an inner catheter 116 with an oval-shaped cross-section. The catheter includes a primary lumen 124, and may also include secondary and tertiary lumens 126 and 160. The primary, secondary, and tertiary lumens 124, 126, and 160 may have similar uses to the primary, secondary, and tertiary lumens 124, 126, and 160 discussed above. The cross section of the inner catheter 116 in this embodiment may be based on an oval shaped extruded polymer with an oval primary lumen 124 to allow mucus aspiration and two round lumens 126, 160 on each side of the primary lumen 124 to give symmetry to the design and to contribute to the torqueability of the cross section. The oval shape may be used as a key inside the ventilator adapter and will allow flexibility of the catheter around one axis of the cross section and the stiffness helpful to maintain the shaped distal end on the other axis of the cross section.

Figure 13:
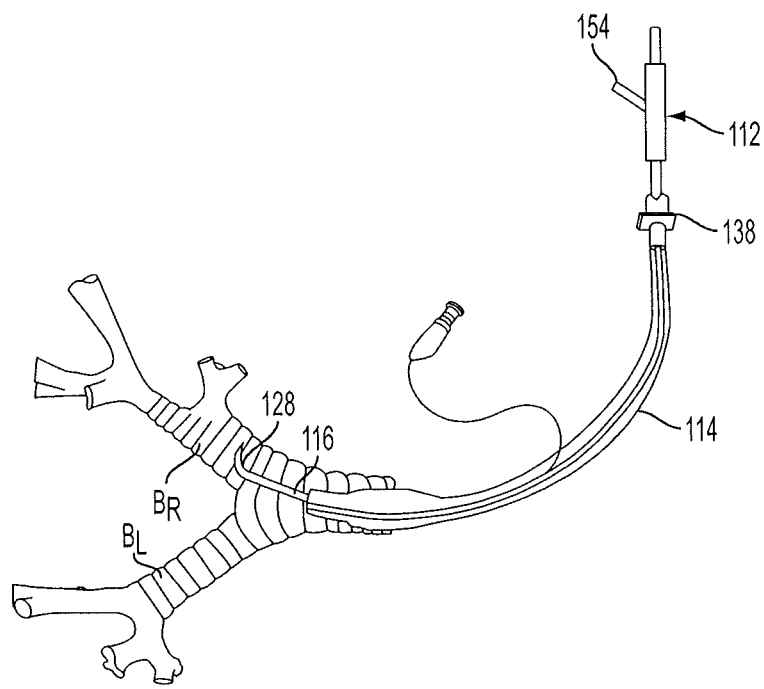
FIG. 13 shows a catheter system with a single inner catheter extended in a first orientation into a patient in an embodiment of the present invention.
Figure 14:
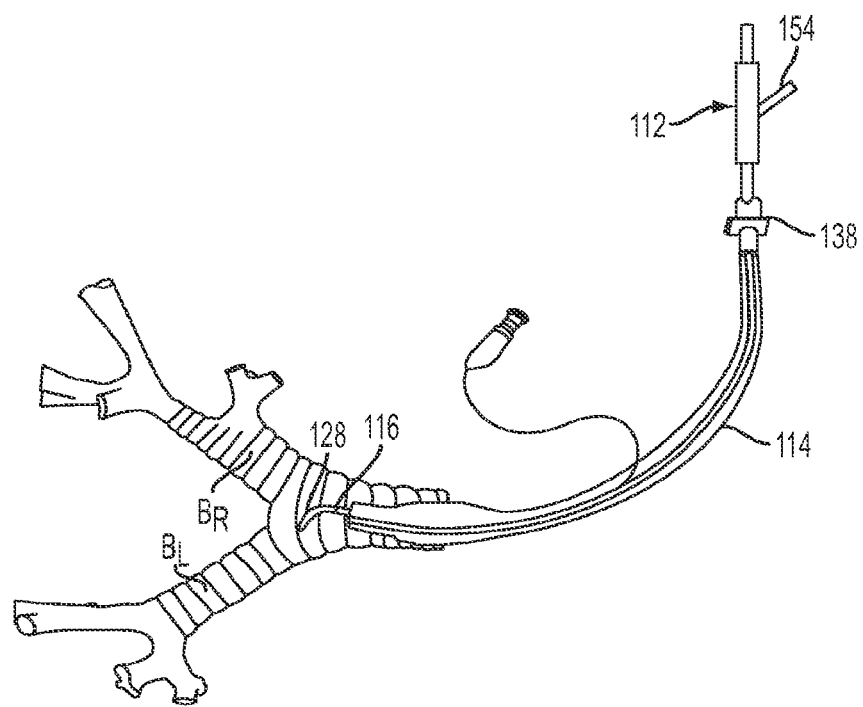
FIG. 14 shows a catheter system with a single inner catheter extended in a second orientation into a patient in an embodiment of the present invention.

A representation of an embodiment of the catheter system 100 being used on a patient is shown in FIGS. 13 and 14. In particular, FIGS. 13 and 14 show how an operator can orient the distal end of the inner catheter 116 towards the desired bronchi branch by pointing the ventilation adapter 154, which is keyed to the inner catheter 116, to the desirable direction in an embodiment of the invention. The catheter 116 may be inserted through an endotracheal tube 114 and steered to the target bronchi using the ventilation adapter 154 on the proximal end of the catheter 116. In FIG. 13, the inner catheter 116 is positioned in the right bronchus BR. As discussed above, the direction of the bend 128 of the inner catheter 116 can be adjusted by the operator on the exterior of the patient. In some embodiments, the torqueability of the catheter 116 can confirm corresponding orientations between the ventilation adapter 154 and the bend 128 of the distal end of the catheter 116. For example, the ventilation adapter 154 can be configured to point in the same direction as the inner catheter 116. By turning the ventilation adapter portion 112, the direction of the ventilation adapter 154 can point in different directions. Additionally, due to the keyed joint formed by the key joint component 110 and the inner catheter 116 (see FIG. 7A or 17B, for example), the rotation of the ventilation adapter portion 112 will correspond to a rotation of the inner catheter 116 positioned within the patient, according to some embodiments. For example, FIG. 13 shows the ventilation adapter 154 and bend 128 of the inner catheter pointing in the same direction with respect to the body of the inner catheter 116. When the ventilation adapter 154 is turned to point in the opposite direction, as shown in FIG. 14, the inner catheter 116 also turns to point in the opposite direction. Accordingly, an operator of the catheter system 100 can easily adjust the inner catheter 116.

Figure 15A:
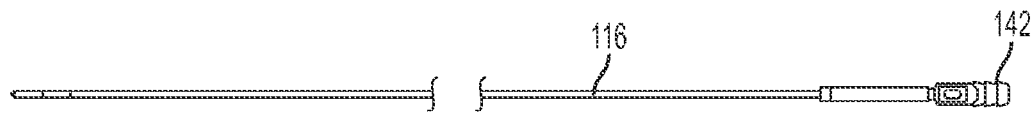
FIG. 15A shows a bottom view of an inner catheter in an embodiment of the present invention.
Figure 15B:
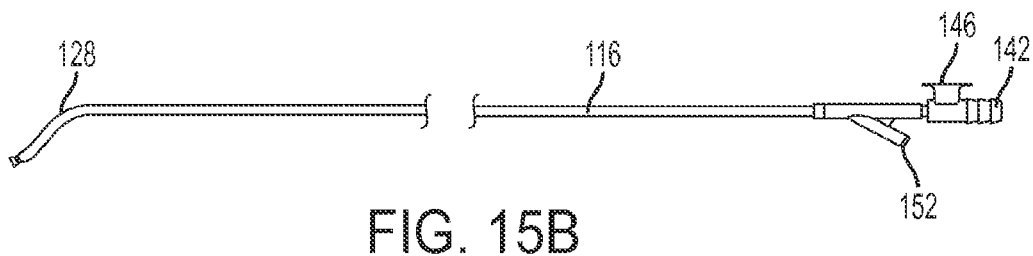
FIG. 15B shows a side view of the inner catheter shown in FIG. 15A in an embodiment of the present invention.
Figure 15C:
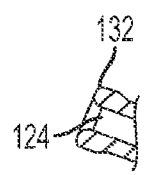
FIG. 15C shows an end tip of an inner catheter in an embodiment of the present invention.
Figure 15D:
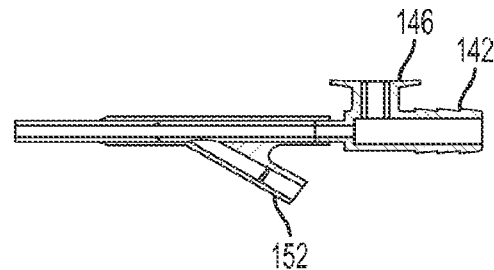
FIG. 15D shows a cross-section detail view of one end of the inner catheter shown in FIG. 15B in an embodiment of the present invention.
Figure 15E:
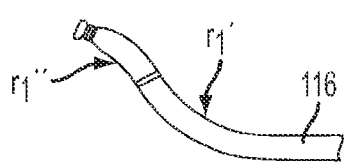
FIG. 15E shows a shape of a distal end of an inner catheter in an embodiment of the present invention.
Figure 15F:
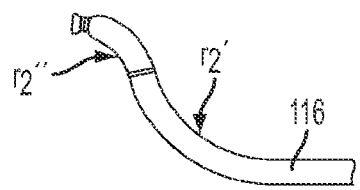
FIG. 15F shows a shape of a distal end of an inner catheter in an embodiment of the present invention.
Figure 15G:
FIG. 15G shows a shape of a distal end of an inner catheter in an embodiment of the present invention.
Figure 15H:
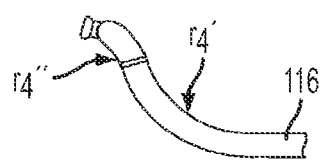
FIG. 15H shows a shape of a distal end of an inner catheter in an embodiment of the present invention.

FIGS. 15A and 15B show an inner catheter 116 according to an embodiment with one example of a possible shape of the bend 128. FIG. 15C shows a close-up of the end of the catheter 116 with a tip formed as an a-traumatic end 132 surrounding the lumen 124. As shown in FIGS. 33A and 33C, for example, X-Ray radiopaque marker band 232 may be attached to the distal end of the catheter 116 to allow visualization under X-Ray. For example, the catheter 116 (or primary lumen 124) may be folded over the marker band and reflowed to secure the marker band to the catheter. FIG. 15D shows a close up of the proximal end of the catheter according to this embodiment. The shape of the bend 128 is not limited to the example shown in FIG. 15B.

Figure 16A:
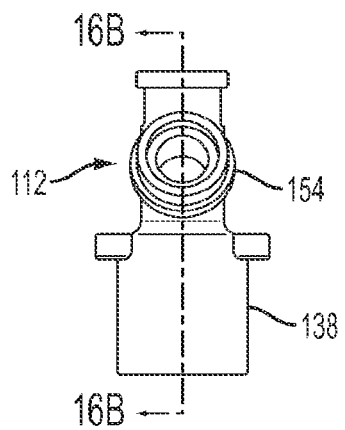
FIG. 16A shows a top view of a connection portion of the catheter system in an embodiment of the present invention.
Figure 16B:
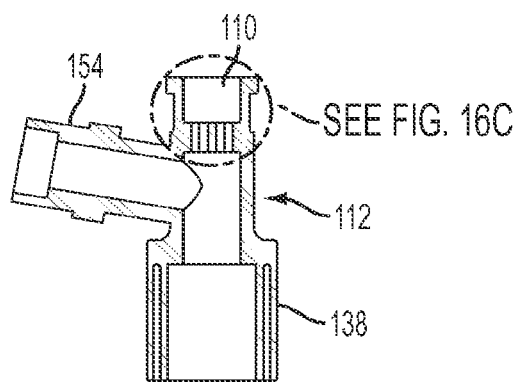
FIG. 16B shows a cross-section of the connection portion shown in FIG. 16A, viewed according to the broken line in FIG. 16A, in an embodiment of the present invention.
Figure 16C:
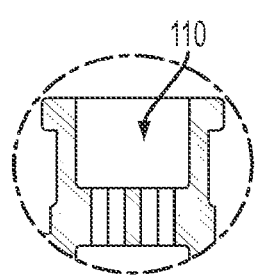
FIG. 16C shows a close-up view of the portion of the connection portion that is circled in FIG. 16B with a key joint component of the connection portion in an embodiment of the present invention.
Figure 16D:
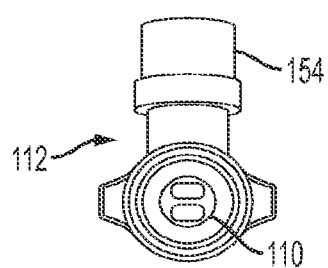
FIG. 16D shows a view of the connection portion of FIG. 16A that is axial with the lumen of the catheter, showing the key joint component in an embodiment of the present invention.

FIGS. 15E-15H show various shapes of the distal end of the of the catheter 116. In each example, the bend is formed having a first radius of curvature $r_1'$, $r_3'$, and $r_4'$, and also a second radius of curvature $r_1''$, $r_2''$, $r_3''$, and $r_4''$. The combination of two curves may be referred to herein as a compound bend or compound curve. In the dual inner catheter embodiments, the inner catheters 116, 117 may have the same or different combination of radii $r_i'$ and $r_i''$. The compound curve of the bend 128 may improve suction and optimize navigation into one or both lungs to efficiently aspirate mucus from one or both lungs FIG. 16A shows an example of the ventilation adapter portion 112 according to an embodiment. In FIG. 16B, a sectional view taken from the dashed line 16B in FIG. 16A reveals the key joint component 110. In this example, the key joint component 110 is keyed for two catheters. A close-up of the key joint component 110 is shown in FIG. 16C. FIG. 16D shows a view looking into the ventilation adapter portion 112. The key joint component 110 with spaces for two inner catheters.

Figure 17A:
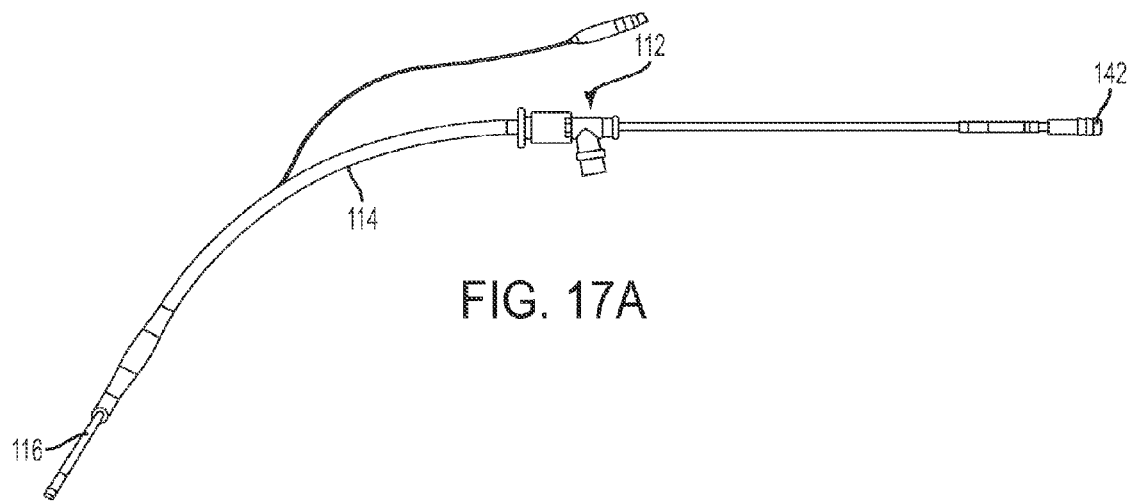
FIG. 17A shows a side view of a catheter system with a single inner catheter in an embodiment of the present invention.
Figure 17B:
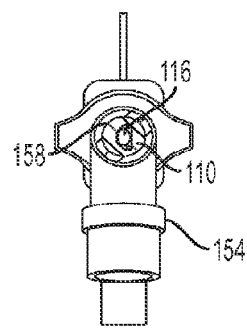
FIG. 17B shows a close-up view of the connection portion of the catheter system shown in FIG. 17A with the key joint component for the single inner catheter in an embodiment of the present invention.
Figure 17C:
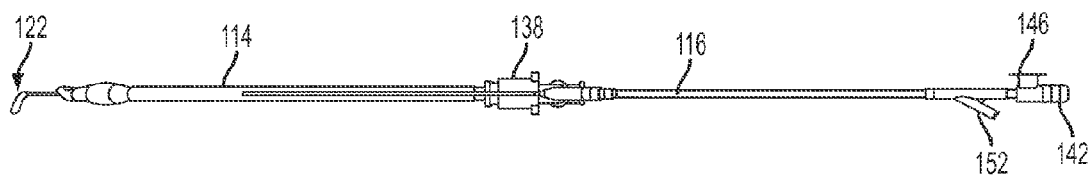
FIG. 17C shows a bottom view of the catheter system shown in FIG. 17A in an embodiment of the present invention.

A single inner catheter 116 embodiment is shown in FIGS. 17A and 17B, with the inner catheter 116 being inserted through an endotracheal tube 114. The key joint component 110, as shown in FIG. 17B, is keyed for a single catheter. FIG. 17C shows an alternate embodiment of a single catheter system.

Figure 18A:
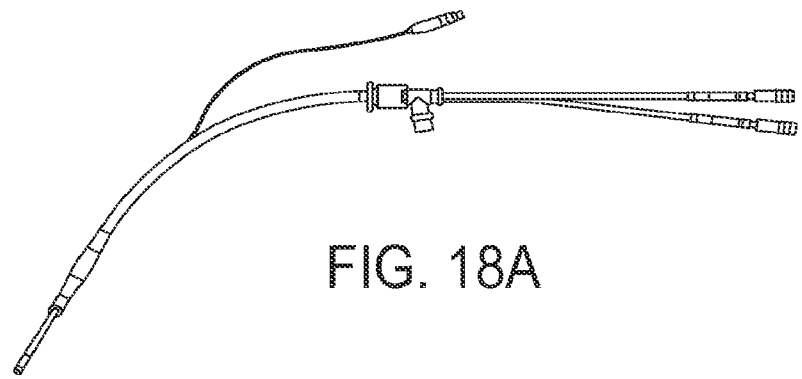
FIG. 18A shows a side view of a catheter system with two inner catheters in an embodiment of the present invention.
Figure 18B:
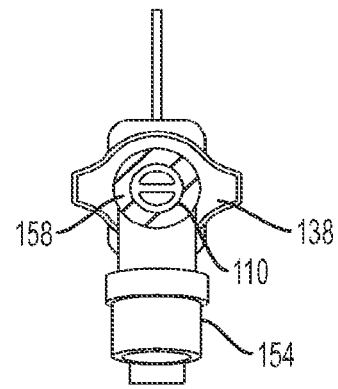
FIG. 18B shows a close-up view of the connection portion of the catheter system shown in FIG. 18A with the key joint component for the two inner catheters in an embodiment of the present invention.
Figure 18C:
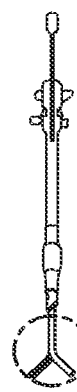
FIG. 18C shows a bottom view of the catheter system shown in FIG. 18A with the two inner catheters oriented in different directions in an embodiment of the present invention.
Figure 18D:
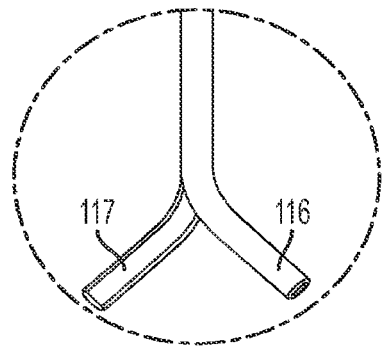
FIG. 18D shows a close-up of the ends of the inner catheters shown in FIG. 18C in an embodiment of the present invention.

A two inner catheter embodiment is shown in FIG. 18A, with both catheters 116, 117 inserted through a single endotracheal tube 114. The key joint component 110 in this example is keyed for two D-shaped inner catheters. D-shaped first and second inner catheters 116, 117 are shown in FIGS. 18C and 18D. In embodiments where the catheters have a different cross-sectional shape, the key joint component may also have a different configuration such that the inner catheters pass through holes in the key joint component that have a shape corresponding to that of the catheter cross-sections.

Figure 19:
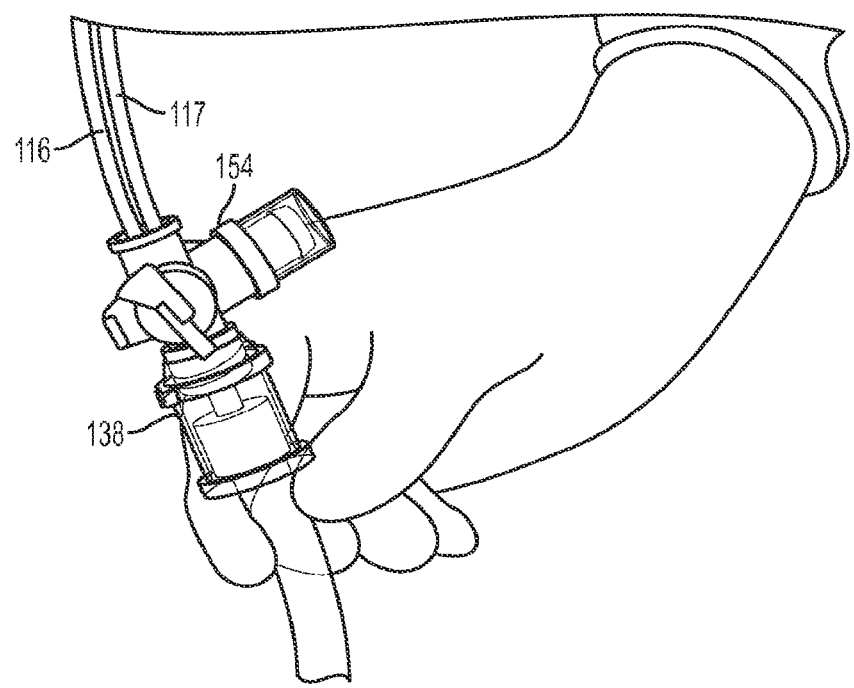
FIG. 19 shows a catheter system being operated in a first orientation by a hand of a user in an embodiment of the present invention.
Figure 20:
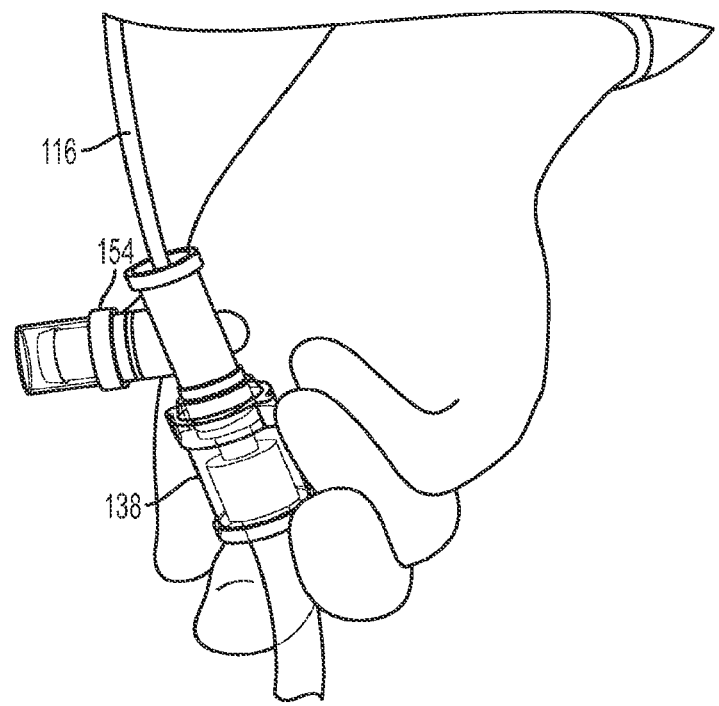
FIG. 20 shows a catheter system being operated in a second orientation by a hand of a user in an embodiment of the present invention.
Figure 21:
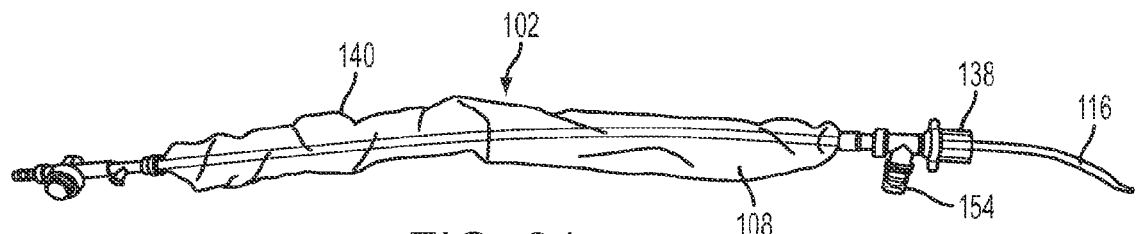
FIG. 21 shows a side view of a catheter system in an embodiment of the present invention.
Figure 22:
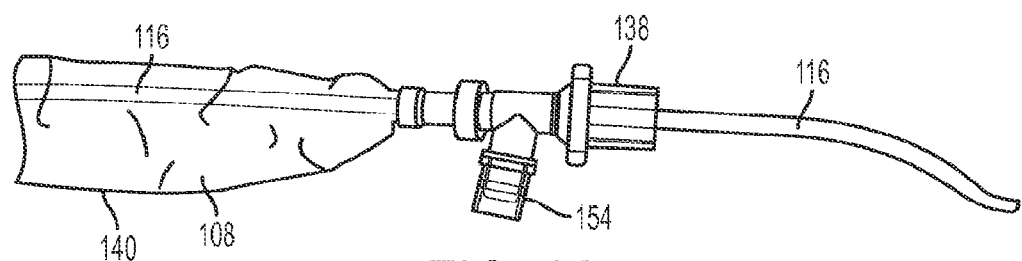
FIG. 22 shows a close-up view of a distal end portion of the system shown in FIG. 21 in an embodiment of the present invention.
Figure 23:
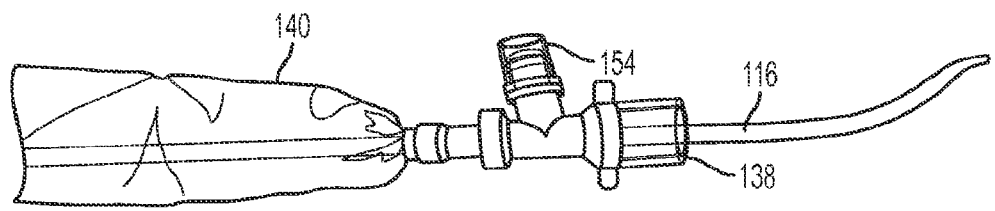
FIG. 23 shows a close-up view of the distal end portion shown in FIG. 22 as shown in an opposite orientation in an embodiment of the present invention.

FIGS. 19 and 20 show examples of how the catheter system can be handled and operated by a user of the system. In FIG. 19, a hand of the user grips the system near the fitting 138 of the ventilation adapter 154. The ventilator adapter allows artificial respiration. While the catheters 116, 117 are introduced through the top port adjacent to the ventilator adapter 154, the ventilation adapter 154 is connected to the artificial respiratory system that can allow a continuous flow of air through the endotracheal tube 114, for example. The user is holding the system such that the ventilation adapter 154 pointing in the direction shown. Due to the keyed joint, the direction in which the distal ends (not shown) of the inner catheters 116, 117 are pointed can be known and controlled even when the distal ends are inside the patient. In FIG. 20, showing a single catheter embodiment, the ventilation adapter 154 is pointed in an opposite direction to that shown in FIG. 19.

Figure 24:
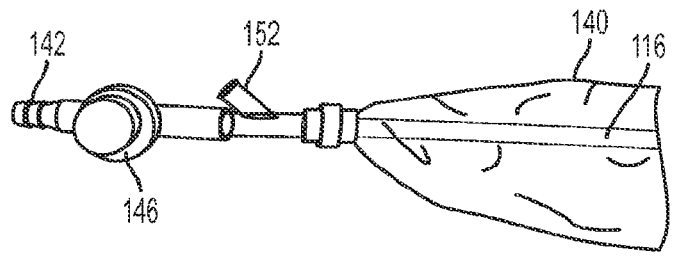
FIG. 24 shows a proximal end of the catheter system in an embodiment of the present invention.

FIGS. 21-24 show an embodiment of the catheter system with a single inner catheter 116. The system is shown without an endotracheal tube connected to the fitting 138. As discussed above, the system can be configured such that the direction in which the ventilation adapter 154 points corresponds to a direction of the orientation of the inner catheter 116 (see FIGS. 22 and 23). Although in these examples the ventilation adapter 154 is used to indicate the orientation of the inner catheter 116, other embodiments are possible. For example, the orientation of the inner catheter can be indicated by another structure or indicator on the system that is external to the patient when the system is in use, such as a marking or other structural feature. The embodiments shown in FIGS. 21-24 show a so-called "closed system" which uses the flexible envelope 140 to keep the catheter 116 in a closed environment to segregate it from the operator for contamination control. However, embodiments are not limited to closed-systems, and may include systems without flexible envelope 140. FIG. 24 shows the valve 146 at the proximal end of the catheter 116 according to an embodiment. This valve 146 can be opened or closed to control the application of suction to the catheter 116 using the primary lumen of the shaft. In a closed system, the valve 146 may have a top or covering that is depressed by an operator of the catheter to control suction. In this way, the valve 146 keeps the interior of the catheter system closed and separated from the operator. Next to the valve 146 there can be an infusion port 152 for administrating fluids through the catheter 116 using, for example, one or more secondary lumens of the catheter 116.

In some embodiments, the catheter 116 is a so-called "open system." FIGS. 15B and 15D, for example, show an embodiment of an open system. The valve 146 in an open system may be an open valve (see FIG. 15D), which is controlled by the operator placing, for example, a thumb over the top of the top valve to control suction. When the top of the open valve is covered (e.g., with a thumb) suction will be performed through the catheter, but when the valve is uncovered, suction will cease. The level of suction may also be controllable by the degree to which the open valve is covered or uncovered. An open system may be provided with or without the flexible envelope surrounding the catheter.

The valve is usually of a kind having a flow control positioned lateral to the flow path and having two distinct positions where flow is either enabled or disabled In the some embodiments discussed herein, the orientation of the inner catheter may be known and/or controlled even when inside the patient due in part to the keyed joint formed by the key joint component 110 and the one or more inner catheters. The inner catheters may have structural or material properties to ensure a correspondence between the orientations of the one or more inner catheters near the keyed joint and at the distal ends of the catheters. For example, the inner catheters may exhibit a 1:1 torqueability ratio along the length of the inner catheter, or at least along a portion of the inner catheter extending from the key joint component 110 to the distal end 122, 123 of the inner catheters 116, 117 in an operating position inside the patient. According to the 1:1 torqueability ratio, a turning or rotating of the one or more inner catheters at the key joint component 110 will result in an equal amount of turning or rotation of the distal ends of the one or more catheters. In other words, a torque at a first end of the catheter will result in an equal degree of rotation at both the first end and a second end, the second end being an opposite end from the first end. Therefore, the orientation of the distal end of a catheter may be known based on the orientation of the catheter on the proximal end, which may be external to the patient. As discussed above, the orientation of the catheter on the exterior of the patient may be indicated by, for example, the orientation of the ventilation adapter 154 or some other indicator.

In some embodiments, rotating the proximal end of the inner catheter may result in the inner catheter twisting over at least a portion of its body due to the tortuosity of the inner catheter when the distal end is inserted into a body lumen (e.g., trachea). Thus, the inner catheter, while in a curved configuration due to the anatomy of the body, may twist such that the orientation of the proximal end may not correspond to the orientation of the distal end. Nonetheless, the inner catheter may still be considered to have "1:1 torqueability" consistent with the definition used herein, because the catheter, while in a straight configuration (i.e., not confined by the body lumen) may exhibit the 1:1 correspondence between distal and proximal ends when the proximal end is rotated.

This 1:1 torqueability ratio may overcome a potential problem in catheters where the disposition (e.g., degree of rotation) of the distal end of a catheter may be unknown when the distal end is inside the body lumen. For example, a catheter may have a distal end disposed in any one of several ways (e.g., any degree of rotation) and the change in disposition of the distal end in response to a rotation of the proximal end of the catheter may be unknown. Specifically, there may be no degree of rotation or disposition of the proximal end that will reliably ensure a given degree of rotation or disposition of the distal end of the catheter. For example, in some catheters, a twist at a proximal end of a catheter may produce no change at the distal end of the catheter, or may produce a rotation at the distal tip that bears no or unreliable relation to the proximal rotation, as described above. Thus, a change at the distal end will produce a different degree of rotation and thus cause unreliable performance for the user. In other words, reliable use of some catheters may be difficult to achieve because the position or orientation of the distal end cannot be reliably known by the user based on controlling or manipulating the proximal end. Regarding these challenges, embodiments of the current invention may offer improved performance.

The inner catheters may be made of, for example, polyvinylidene fluoride or polyvinylidene difluoride (PVDF), which is highly non-reactive thermoplastic fluoropolymers produced by the polymerization of vinylidene difluoride. Kynar™ is one example of such a material. The 1:1 torqueability may be achieved by the inner catheter being formed from a rigid material having properties that include, for example, one or more of the following: (1) a Shore D hardness of about 55.0 to 60.0; (2) an ultimate tensile strength of about 4000 to 6000 psi; and (3) a yield tensile strength of about 1700 to 2800 psi. However, other material properties or combinations of properties may also achieve or contribute to 1:1 torqueability. Additionally, the inner catheter may be formed to have a cross-section that provides, for example, a high polar moment of inertia, indicating the ability of the shaft to resist torsion in an embodiment of the invention, and which is required to calculate the twist of a shaft subject to torque. In certain embodiments, the cross-section may include a flat portion.

The following discussion uses simplified equations that are representative of general principles of structural and material behavior. Some of the equations below depend on physical geometry of a member (i.e., catheter). Embodiments of the invention include various geometries which may not be exactly described by the equations below. Thus, aspects (e.g., geometry) of embodiments of the invention are not meant to be limited by the geometries implied by any of the below equations. Nonetheless, the general principles below are applicable to design considerations of embodiments of the current invention.

Catheter torqueability describes the behavior of a catheter when a moment of torque is placed about its longitudinal axis. For small deflections, the catheter's mechanical properties approximate a spring system in which torsional stiffness is determined such that:

$$k_{torq} = \frac{GJ}{L}$$

where $k_{torq}$ is the torsional spring constant, G is the shear modulus, J is the polar moment of inertia, and L is the length of the catheter shaft. Maximizing torqueability means maximizing the quantity $k_{torq}$, which can be accomplished by any of the following three ways:

(1) maximizing the polar moment of inertia. For a single tube profile, the governing equation for J is as follows:

$$J = \frac{\pi}{32}(d_o^4 - d_i^4)$$

where $d_o$ is the tube outer diameter and $d_i$ is the tube inner diameter. In order to maximize J, the designer needs to maximize the outside diameter and the wall thickness;

(2) maximizing the shear modulus by using a stiffer material; or (3) decreasing the overall length of the shaft.

Flexibility for a simple tube can be modeled as a clamped beam system subject to a downward force at the beam. For small deflections, the tubing approximates a spring system, with the flexural stiffness determined by:

$$k_{flexural} = \frac{3EI}{L^3}$$

where $k_{flexural}$ is the flexural spring constant, E is the modulus of elasticity, I is the moment of inertia, and L is the length of the catheter shaft. In many cases, it is desirable to minimize the flexural stiffness of the catheter, which may be done by minimizing the quantity $k_{flexural}$, which can be accomplished by, for example, one of the following three ways:

(1) minimizing the moment of inertia. For a cylinder, the governing equation for the moment of inertia is:

$$I = \frac{\pi}{64}(d_o^4 - d_i^4)$$

Where $d_o$ is the tube outer diameter and $d_i$ is the tube inner diameter. In order to minimize I, the outer diameter and the wall thickness may be minimized;

(2) minimizing the modulus of elasticity by using a soft material; and (3) increasing the overall length of the shaft.

Composite tubing designs may be used for catheter delivery systems. These may include one or more plastic materials as well as wire-reinforced (braid or coil) designs. The modeling concepts described previously can also be used to analyze and compare composite tubing designs. The stiffness properties of each separate and distinct layer can be computed and combined using principles of classical lamination theory.

The aspiration catheter system may be a sterile, single-use, disposable device whose primary purpose is to blindly but accurately deliver suction tubes to the left and right bronchi through the endotracheal tube. The secondary purpose of the catheter system is to provide a second channel in order to administer therapeutic agents to the airways. The second channel prevents these agents from mixing with the fluids removed from lungs. The second channel may also be used for lavage.

An intended use of the aspiration catheter system can be to remove fluids and mucus that congest the airways. The system allows the accurate introduction of suction tubes into the left and right bronchi without the use of visual guidance. Removing the fluids will ameliorate the symptoms of pneumonia, improve breathing and overall lung function, thereby accelerating the patient's recovery.

The aspiration catheter system may use multi-lumen shaped suction tubes inserted through an off-the-shelf-endotracheal tube using a keyed ventilation adapter. The combination of pre-shaped, keyed suction tubes inside an off-the-shelf endotracheal tube allows the physician to insert the tracheal tube using standard techniques. Once positioned, one or two suction tubes are deployed from the distal end of the endotracheal tube and form a bifurcated shape that directs these tubes in left and right bronchi. The catheter system allows efficient and sterile delivery of therapeutic agents through a dedicated lumen to avoid contamination.

The catheter system can be used in conjunction with a commercially available stethoscope to confirm the location of both suction tubes, and by listening to the fluid suction noises, the operator can confirm the suction tubes were properly deployed into both primary bronchi.

Increasingly, modern medicine demands devices that can navigate narrow passageways to a desired location within a body so that diagnostic and therapeutic procedures can be performed. Currently, elongated medical devices such as catheters can extend into the body via an access point through various connected passageways to a target location. Though these approaches are common in cardiac and vascular disease, they have not been well applied in pulmonary disease.

The respiratory tract is an example of a tortuous pathway. The respiratory tract begins at the nose and mouth, which open to the trachea. The trachea travels downward into the chest and it splits into the left and right main bronchi. The left and right main bronchi split at an angle from the trachea. The left main bronchus is smaller in diameter and branches at a greater angle from the trachea than the right main bronchus. The main bronchi then split into lobar bronchi, which split into segmental bronchi. The segmental bronchi split into subsegmental bronchi.

Several procedures require intubation of the respiratory tract, including the left and right main bronchi, to aspirate mucus in the lungs or to deliver localized medicine. Intubation of the left main bronchus from the trachea can be difficult because it can have a smaller diameter and greater angle relative to the trachea. For example, a typical procedure for aspirating fluid from the lungs can include introducing an endotracheal tube to the trachea of a patient, followed by extending a working catheter (e.g., an aspiration catheter) through a lumen of the endotracheal tube and into either the right or left main bronchus. Respiratory therapists seeking to intubate the left main bronchus with the aspiration catheter may mistakenly believe the left main bronchus has been intubated, when the catheter has actually entered the right main bronchus instead. In some instances, the endotracheal tube can be mistakenly inserted too deep so that its distal end extends into the right main bronchus, whereby the aspiration catheter can only access the right main bronchus. Often times, a specialist, such as a pulmonologist, is needed to insert a bronchoscope into the left main bronchus and aspirate the left main bronchus using the working channel of the bronchoscope. The bronchoscope is equipped with a vision system (including, for example, a fiberoptic system) and/or a fluoroscopic imaging system, to guide the bronchoscope into the left main bronchus. However, visualization equipment and the endoscopic procedure can be expensive, and specialists may not be readily available to conduct the procedure when desired.

Closed system suction catheter assemblies are used for removing secretions from within the trachea or bronchi of an intubated patient. The assembly comprises a flexible catheter connected at its distal end to the proximal end of an endotracheal tube. The proximal end of the flexible catheter is connected with a fitting, including a valve, that can be opened or closed to control the application of suction to the catheter. The valve is usually of a kind having a flow control positioned lateral to the flow path and having two distinct positions where flow is either enabled or disabled.

Towards its distal end, the catheter extends through a fitting connected between the end of a tracheal tube and a ventilation circuit. The catheter can be advanced through the fitting down the tracheal tube to enable suctioning. A flexible envelope extends between the two couplings, enclosing the catheter so that it can be manipulated through the envelope. A wiper seal in the forward coupling prevents gas from the ventilation system inflating the envelope.

In some assemblies, provision is made for cleaning the catheter after its patient end has been withdrawn into the forward coupling. A manually-operable valve is located forward of the wiper seal providing a cleaning chamber between the valve and the wiper seal. An irrigation port opens into this chamber so that saline can be supplied to it, which is then drawn along the bore of the catheter by the applied suction to remove matter collected within the bore.

Figure 25:
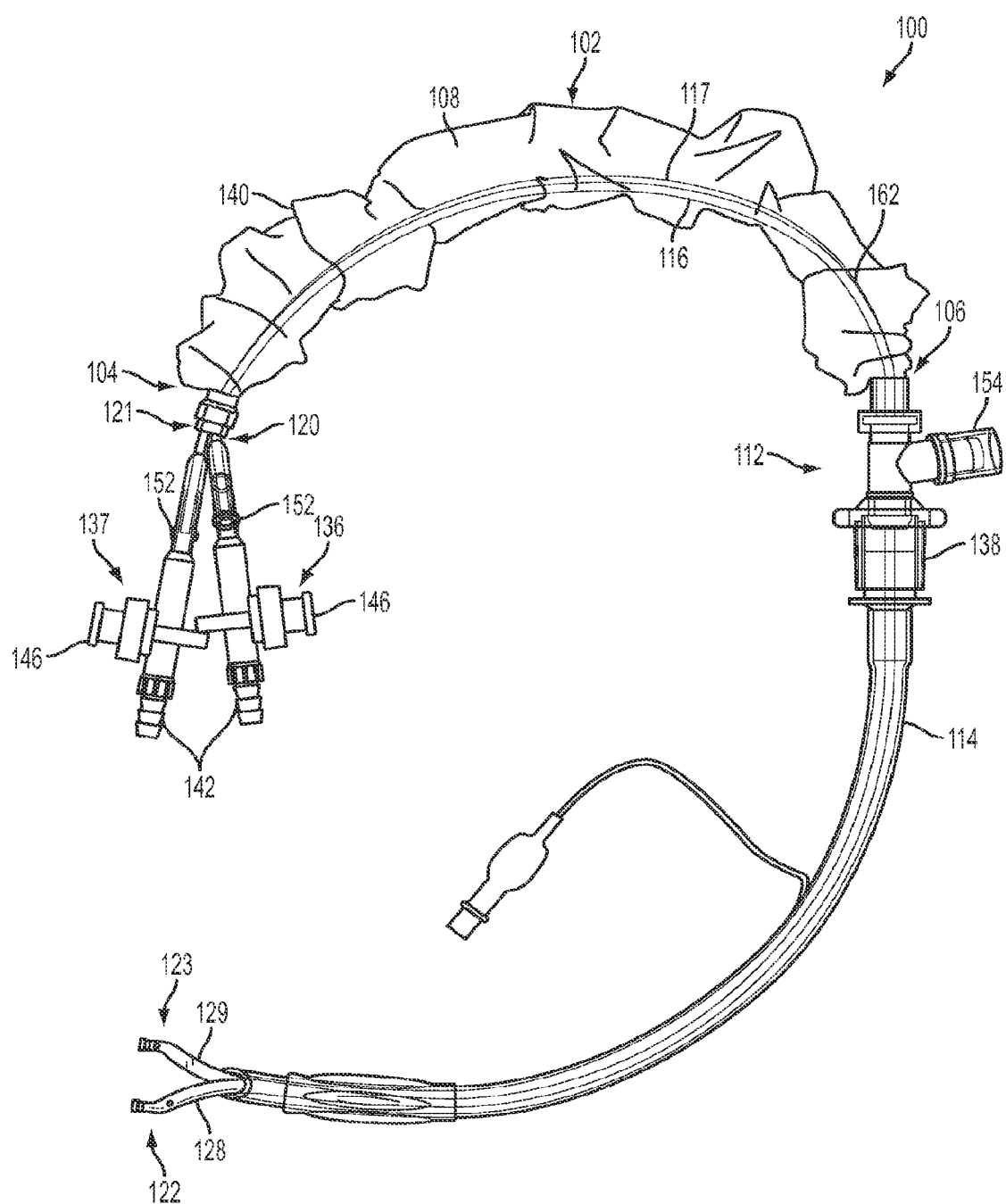
FIG. 25 shows a view of a catheter system having a lubricious sleeve in an embodiment of the present invention.

According to the above embodiments in which two or more inner catheters are provided, each inner catheter may be slideable independent of the other inner catheters. For example, the extent to which a first inner catheter extends out of the catheter system or an endotracheal tube can be adjusted independently of the extent to which a second inner catheter is extended. This may allow for independently targeting the left or right bronchus, or lumens within one of the bronchi. In an embodiment, at least a portion of two or more inner catheters may be housed within a lubricious sleeve 162, as shown in FIG. 25. The lubricious sleeve 162 can help facilitate the sliding of one or more of the inner catheters in and/or out of the catheter system during use. The lubricious sleeve 162 may be a lubricious double lumen sleeve with inner catheters being separately housed in different lumens of the double lumen sleeve. In the double lumen configuration, the lubricious sleeve 162 may allow, for example, the position of one inner catheter in one lumen of the double lumen sleeve to be adjusted without interfering with the position of another inner catheter in the other lumen of the double lumen sleeve.

Figure 26A:
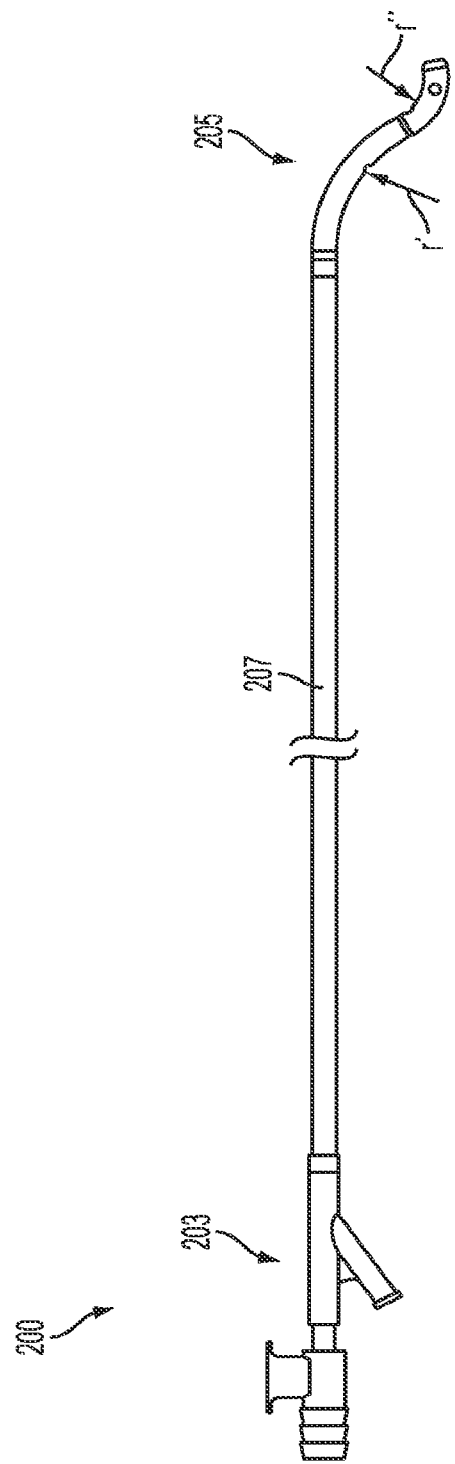
FIG. 26A shows a side view of a catheter according to an embodiment of the present invention.

FIG. 26A shows a catheter 200 according to an embodiment of the invention. The catheter 200 has a proximal end 203, a distal end 205 that may include a pre-formed curve, and an elongated body 207 extending between the proximal and distal ends 203, 205. In the embodiment shown in FIG. 26A, the distal end 205 has a compound curve comprising two curves, with one curve having a radius of curvature of r' and the other curve having a radius of curvature of r''.

Figure 26B:
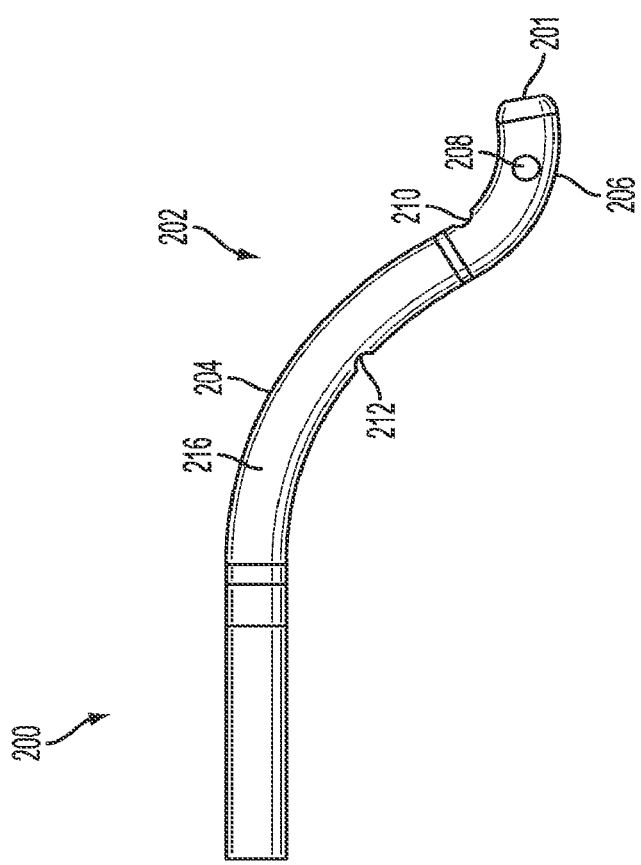
FIG. 26B shows a side view of a distal end of the catheter shown in FIG. 26A according to an embodiment of the present invention.
Figure 27:
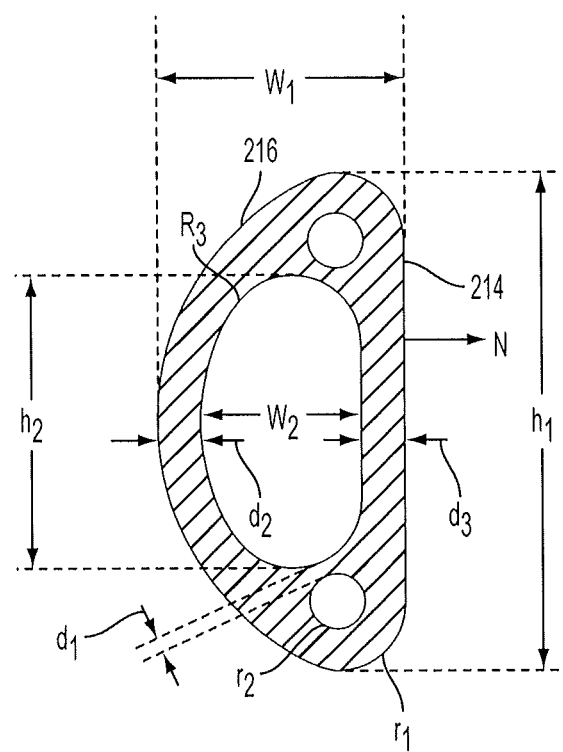
FIG. 27 is a cross-section view of the catheter in an embodiment of the present invention.

FIG. 26B shows a distal end of a catheter 200 according to an embodiment of the current invention. The catheter 200 includes a pre-formed curve 202. In a preferred embodiment, the pre-formed curve 202 includes a first curve 204 and a second curve 206, examples of which are shown in FIG. 26B, though embodiments are not limited to this configuration and may include one or more curves. The pre-formed curve 202 may have radii of curvature corresponding to those discussed above. The catheter 200 may include a first opening 208, a second opening 210, and a third opening 212. Each of the first, second, and third openings 208, 210, and 212 correspond to separate lumens (not shown in FIG. 26B, but see FIG. 27 and FIG. 30B showing a cross-sections of catheter 200 including three lumens) within the catheter 200. For example, opening 208 opens to the first lumen 226 (see FIG. 30B). However, the first lumen 226 may be provided with multiple openings, including three openings 208a, 208b, and 208c in some embodiments, as discussed further below. (See, e.g., FIGS. 34A-34F).

As discussed above, each lumen can be configured to perform multiple functions. In one embodiment, the first opening 208 may be configured to perform a suction function. Additionally, second and third openings 210 and 212 may perform suction or other functions, such as lavage, for example. The location of each opening relative to the distal tip 201 of the catheter 200 and relative to each other can have certain advantages according to embodiments of the invention. For example, if an opening performing suction and an opening performing irrigation are too close to each other, the fluid leaving the irrigation hole may be immediately taken in by the opening performing suction, which can minimize the effect of the irrigation and/or suction. If the fluid used for irrigation is suctioned before washing a sufficient portion of the anatomy, for example, the irrigation function may be negatively impacted. However, with sufficient spacing between the respective openings, this negative effect can be reduced or minimized by allowing the fluid from the irrigation opening to wash a larger area of the anatomy before being suctioned. An additional advantage of staggering the openings 208, 210, and 212 along a length of the catheter 200 is that the number of openings in any one subdivision of that portion is reduced. For example, in FIG. 26F, openings 210 and 212 are positioned at different points along the catheter 200. This may increase structural integrity of the catheter and decrease the chance that the catheter kinks during use.

Accordingly, in some embodiments, opening 208a may be a distance $d_1$ from the distal tip 201; opening 210 may be a distance $d_2$ from opening 208a; and opening 212 may be a distance $d_3$ from opening 210, where distances $d_1$, $d_2$, and $d_3$ are linear dimensions measured in a direction parallel to the x-axis (see FIG. 26E). The x-axis may be parallel to the longitudinal axis (corresponding to line $L_2$) of the elongated body of the catheter 200. It is also understood that, due to the curvature of the distal end, the values of $d_1$, $d_2$, and $d_3$ may result in varying vertical distances (i.e., parallel to the y-axis) between the openings. Further, values of $d_1$, $d_2$, and $d_3$ can be constant across catheters of different curvatures while resulting in different spacings in the y-direction, and vice versa. In one example, $d_1$ can be about 7 mm, $d_2$ can be about 5 mm, and $d_3$ can be about 15 mm. In the above discussion, $d_1$ is referred to as the distance between the distal tip 201 and opening 208a. The distance between opening 208b and the distal tip 201 may also be $d_1$ or may be a different distance.

In addition to the staggered spacing of openings 208, 210, and 212, as shown in FIG. 26E, for example, the direction in which the openings 208, 210, and 212 can also be varied. For example, with reference to FIG. 26E, opening 208 faces in a direction parallel to the z-axis, while openings 210 and 212 both face different directions from that of opening 208. Additionally, openings 210 and 212 can face directions that are substantially opposite to one another. For example, in FIG. 26E, opening 210 faces a direction $a_1$ that is at an angle $\gamma_1$ to a line parallel to the y-axis. In contrast, opening 212 faces a direction $a_2$ that is at an angle $\gamma_2$ to a line parallel to the y-axis. According to some embodiments, $\gamma_1$ and $\gamma_2$ may be substantially equal in magnitude, but they may be different in magnitude according to other embodiments. For example, $\gamma_1$ and $\gamma_2$ may be determined, at least in part, by the amount of curvature in each curved portion of the compound curve of the catheter 200, as well as by the location of each opening 210, 212 along the length of each curved portion. Additionally, by facing openings 210 and 212 in different directions, perhaps substantially opposite directions in some embodiments, irrigation or the dispensing of therapeutic agents may be directed in either direction, as needed, or in both directions to treat a larger area or volume of the anatomy.

FIG. 26E also shows that the distal tip 201 (shown in FIG. 26B) may be curved slightly upward at angle θ relative to a line ($L_1$) that is parallel to the x-axis. For reference, line $L_2$ corresponds to a longitudinal axis of the catheter, and line $L_2$ is shown parallel to the x-axis and $L_1$. This configuration of the distal tip 201, along with the compound curve of the bend, can help the catheter 200 to be pushed through a Murphy's eye of a delivery catheter in a relatively unobstructed manner. The shape of the curve of the distal end of the catheter shown in, for example, FIG. 26E is an example of a reverse curve. The reverse curve shown in FIG. 26E starts with a first curve that begins at a point on line $L_2$ and curves in a direction until a point where the reverse curve reverses direction to begin a second curve that curves in an opposite direction opposite to that of the first curve until it ends or exits an arc of the curve at a point. This point where the second curve ends or exits the arc is on a tangent line $L_3$ to the second curve that is non-parallel to $L_2$, as indicated by angle θ, as lines $L_1$ and $L_2$ are parallel. The distal tip 201 may also have an opening 208c (see FIG. 33D) to the first lumen 226 and have a beveled edge. The beveled edge may minimize trauma to tissue and/or may be formed when closing off the second and third lumens 228, 230 of the extrusion. Alternatively, the distal tip 201 may be closed so that there is no opening.

Additionally, the direction and location of openings 208, 210, and 212 can be specified relative to a particular surface of the catheter 200. In FIGS. 26B-26F, for example, opening 208 is formed on a curved surface 216 of the catheter 200. In other embodiments, opening 208 may be formed on the flat surface 214 (see FIG. 26F).

The spacing of openings 208, 210, and 212 in FIGS. 26B-26F is an example of one embodiment, but embodiments of the current invention are not limited to the spacing shown. The openings 208, 210, and 212 can, for example, have greater or smaller spacing and/or face different directions from the catheter than the directions shown. Although three openings 208, 210, and 212 are shown in FIGS. 26B-26F, more or fewer openings may be present according to various embodiments of the invention.

Placement of the openings 208, 210, and 212 relative to the pre-formed curve 202 can also have certain advantages. For example, the second and third holes 210 and 212 in FIG. 26B are each formed on the inside curves of first and second curves 204 and 206, respectively. This arrangement may protect the anatomy of a patient by reducing the likelihood that holes 204 and 206 will be placed in immediate contact with tissue of the patient during use. For example, the tissue may be traumatized by the edges of holes scraping against the tissue. However, the positioning of the second and third openings 210 and 212 on the inside of curves 204, 206 decreases the likelihood that the openings 210, 212 will scrape the tissue. Accordingly, trauma to the issue caused by scraping of the opening edges is reduced. Additionally, fluid inflow (i.e., suction) or fluid outflow directly against the tissue can be reduced, which may also reduce trauma to the tissue.

Furthermore, positioning the first opening 208 distal to the pre-formed curve 202 (i.e., reducing the distance between the first opening 208 and the distal tip 201) can reduce a moment at the first opening 208 during, for example, suction, and thus, the likelihood of the catheter collapsing is reduced. The distal tip 201 may have a beveled or folded edge to be a-traumatic. FIG. 27 shows a cross-section the catheter 200 according to an embodiment of the present invention. The general shape of the cross-section in FIG. 27 is a D-shape, having a first side 214 that is flat with a normal N and a second side 216 that is curved. However, embodiments are not limited to this specific shape. For example, some embodiments may have a first side that is flat, while a side opposite to the flat side may be curved (as in FIG. 27, or with a different curve) or flat. In one embodiment, the cross-section has a relatively flat, substantially rectangular "ruler" shape. The dimensions of various aspects of the cross-section can affect the response (i.e., the "binary response") of the catheter according to some embodiments by changing, for example, the polar moment of inertia or other properties. For example, as shown in FIG. 27, the cross-section may have a width $w_1$, height $h_1$, and curved transitions with radii $R_1$ between the curved and flat sides 216, 214. The catheter cross-section may also have a primary lumen with a width $w_2$, a height $h_2$, and curved portion with radius $R_3$. Secondary lumens may be spaced from the primary lumen at a distance of $d_1$ and may have radii of $R_2$.

Figure 28A:
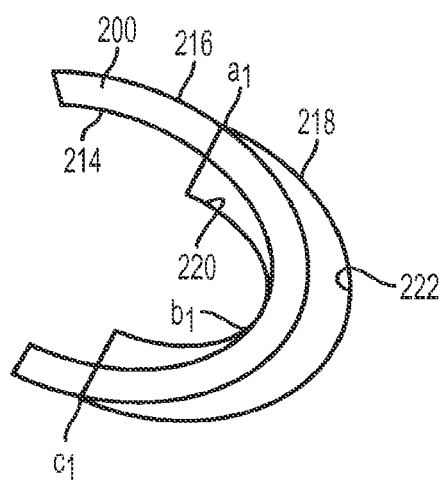
FIGS. 28A, 28B, 28C, 28D, and 28E show schematics of catheters when inserted into delivery catheters according to an embodiment of the present invention, with the portion of the catheter that is shown in FIGS. 28A-28E being indicated by the dashed line C in FIG. 9A.

Some embodiments of the invention include a catheter that may be inserted into a body lumen of the patient by passing the catheter through a delivery lumen, such as an endotracheal tube. In some of these embodiments, there may be contact between the catheter and the delivery lumen, and that contact may effect or contribute to the binary response of the distal end of the catheter. FIGS. 28A-28E show schematics of catheters 200 while inserted into an endotracheal tube 218 according to some embodiments. The curvature of the catheter 200 and endotracheal tube 218 is dictated by the anatomy of the body lumen. The catheter 200, for example, is flexible enough to curve when inserted through the endotracheal tube 218. The endotracheal tube 218 can be considered to have a first wall 220 and a second wall 222, as shown in FIG. 28A. According to embodiments of the current invention, when the catheter 200 is placed within the endotracheal tube 218, the first wall 214 of the catheter may contact the first wall 220 of the endotracheal tube, and the second wall 216 of the catheter may contact the second wall 222 of the endotracheal tube. However, in some embodiments, only one of the first and second walls 214, 216 of the catheter 200 may contact a wall of the endotracheal tube. The orientation of catheter 200 in FIG. 28A may be considered to be a first orientation of the catheter. By rotating the catheter 200 at the proximal end about the longitudinal axis of the catheter 200 while inserted in the endotracheal tube 218, the catheter 200 may achieve a second orientation in which the first wall 214 of the catheter is contacting or facing the second wall 222 of the endotracheal tube and the second wall 216 of the catheter is contacting or facing the first wall 220 of the endotracheal tube (see FIG. 28E, for example). Points of contact between the catheter 200 and the endotracheal tube 218 are indicated by a, b, and c in FIG. 28A-28E. FIGS. 28A-28E demonstrate the various combinations of points of contact possible between the catheter 200 and the endotracheal tube 218 according to various embodiments.

Figure 28B:
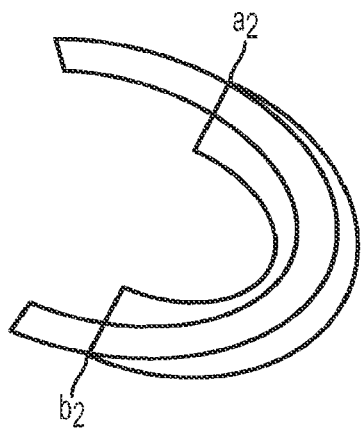
Figure 28C:
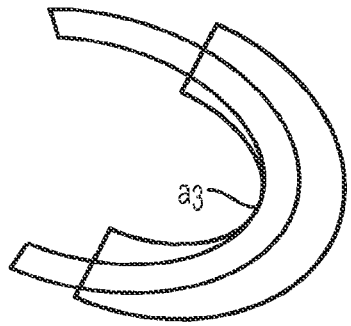
Figure 28D:
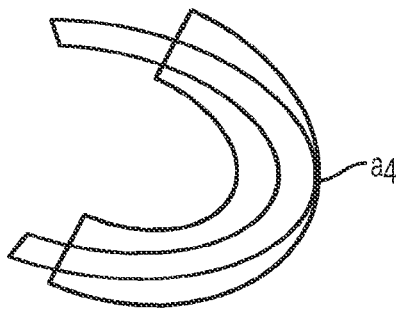
Figure 28E:
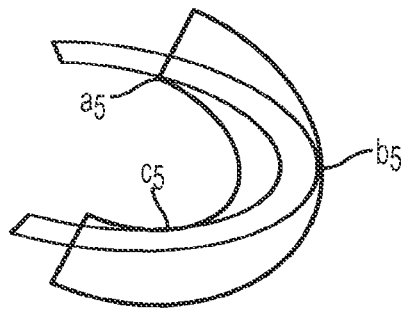

For example, in FIG. 28A, one side of the catheter 200 (e.g., the flat side 214, as shown, but in some embodiments either side of the catheter 200 may be facing either direction) is touching one point $b_1$ of the endotracheal tube 218, and the other side (e.g., the curved side 216, as shown) is touching two points $a_1$ and $c_1$ of the endotracheal tube 218. However, depending on the properties of the catheter 200 and the curvature of the endotracheal tube 218 or the anatomy of the patient, the catheter 200 may contact the endotracheal tube according to a number of arrangements. In FIG. 28B, for example, one side of catheter 200 is not touching the endotracheal tube 218, while the other side of the catheter is touching at two points of contact $a_2$ and $b_2$. In FIG. 28C, there is one point of contact $a_3$ on a first side of the catheter, but no points of contact on the second side, while in FIG. 28D there are no points of contact on the first side and one point of contact $a_4$ on the second side. Finally, as yet another example, there are two points of contact $a_5$, $c_5$ on the first side of the catheter and one point of contact $b_5$ on the second side. In some embodiments, a catheter may have a configuration from one of FIGS. 28A-28E when the catheter is in a first orientation, and the catheter may have one of the other configurations from FIGS. 28A-28E, or the same configuration, when rotated 180° to a second orientation. These configurations are examples of some embodiments, but embodiments of the invention are not limited to these configurations.

Figure 29E:
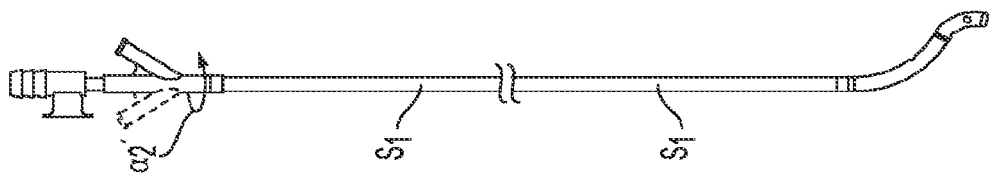
FIGS. 29A, 29B, 29C, 29D, and 29E show a binary response of a distal end of the catheter in response to a rotation of the proximal end of the catheter in an embodiment of the present invention.
Figure 29D:
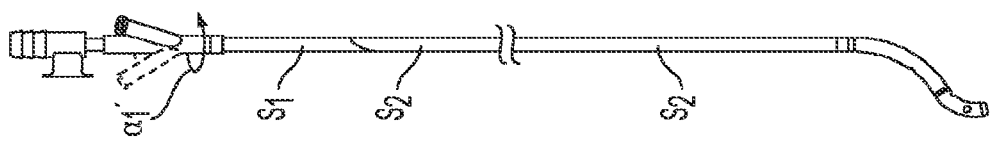
Figure 29C:
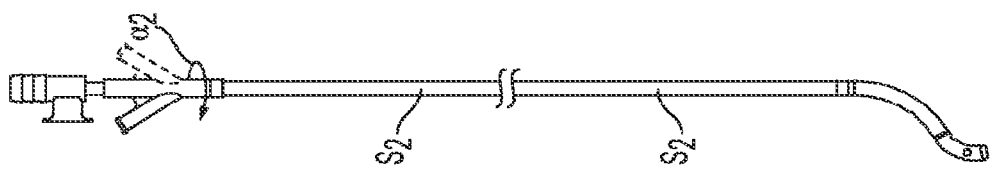
Figure 29B:
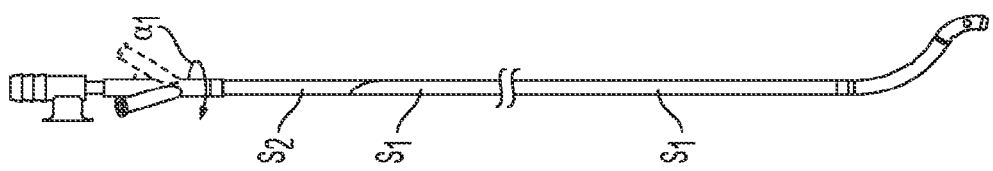
Figure 29A:
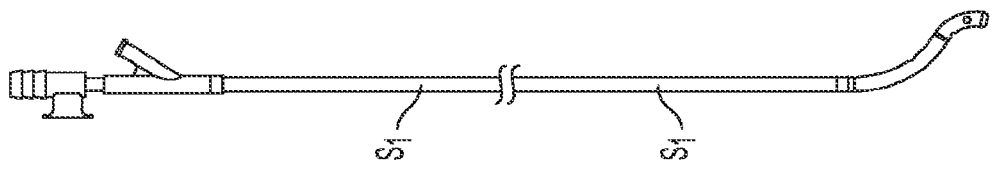

Some embodiments of the current invention, due to a variety of the above-discussed features, exhibit a unique and advantageous response during use due to the unique combinations of features described herein. An embodiment of a catheter having this response is shown in FIGS. 29A-29E. Specifically, when inserted into a body lumen of a patient, a catheter may be in a first orientation (FIG. 29A, for example). A rotation of the proximal end of the catheter may then produce a binary response at the distal end of the catheter. "Binary response," as used herein, means that the distal end of the catheter is capable of two resting positions or orientations, such that the distal end of the catheter is in one of those two resting orientations at any given time. More specifically, when inserted into a body lumen of a patient (including possibly through a delivery lumen such as an endotracheal tube), a proximal end of the catheter may be rotated by an operator of the catheter from a first orientation (FIG. 29A, for example) to a second orientation (FIG. 29C, for example). Over a range of degrees of rotation $\alpha_1$ at the proximal end of the catheter, the distal end of the catheter will remain in a first orientation, substantially without rotating (see FIG. 28B and FIG. 28D). However, upon achieving a predetermined degree of rotation $\alpha_2$ at the proximal end, the distal end of the catheter will respond by "flipping" from the first orientation to the second orientation (see FIG. 29C and FIG. 29E, for example). The second orientation of the distal end may be an approximately 180° rotation from the first orientation of the distal end. Because the distal end remains in one orientation while the proximal end is rotated through a range of degrees of rotation, some twisting of the elongated body of the catheter will occur before the flipping of the distal end. This twisting is shown in FIGS. 29B and 29D, for example. For example, FIGS. 29B and 29D each show both side $s_1$ and $s_2$ of the catheter. Because $s_1$ and $s_2$ are different or opposite sides of the catheter, the visibility of both sides $s_1$, $s_2$ in those figures indicates a twisting of the catheter. The twisting shown in FIGS. 29B and 29D is only to symbolically indicate that twisting occurs and may not be representative of the actual appearance of twisting during use of a catheter according to these embodiments. According to some embodiments, the rotation necessary at the proximal end of the catheter to achieve this response at the distal end of the catheter is at least 90°. According to other embodiments, the rotation necessary at the proximal end is at least 135°, or at least 150°, or approximately 180°. Although the "flipping" of the distal end of the catheter means that the catheter may pass through a range of degrees, the distal end nonetheless may have only two resting orientations. Therefore, the "flipping" does not contradict the "binary response" described above.

According to the above described flipping, a proximal end of a catheter that is taken from a first orientation and twisted or rotated to a degree that is not sufficient to achieve the flip will result in the proximal end returning to the first orientation when the applied torque is removed. Due to the 1:1 torqueability of the catheter, an operator of the catheter will know the orientation of the distal end based on the orientation of the proximal end. Therefore, in this example, the return of the proximal end to the first orientation will indicate to the operator that the flip has not occurred, and that the distal end orientation corresponds to the proximal end orientation. In contrast, when the torque at the proximal end produces a degree of twisting or rotation that is sufficient to produce the flip, the distal end will flip to its second orientation (e.g., approximately 180° from its first orientation). With the distal end in its second orientation, the proximal end will also move to its second orientation (corresponding to the distal ends second orientation due to 1:1 torqueability) when the torque at the proximal end is no longer applied, if not already in the second orientation.

According to embodiments of the current invention, the factors that contribute to the binary response of the distal end of the catheter may include: the catheter cross-section (including having one substantially flat side); the structural dimensions of the catheter (including wall thickness, length of catheter, lumen configuration, and other features); material properties of the catheter material (including hardness, stiffness/torsional stiffness, elastic modulus, ultimate and yield tensile strength); and composition of the catheter material.

According to some embodiments, a catheter capable of achieving the above-described binary response may also exhibit 1:1 torqueability when not inserted into a body lumen of a patient.

According to some embodiments of the current invention, a binary response catheter is provided which has a pre-formed curve, as discussed above and shown in FIGS. 26B and 31A-31C, for example. The pre-formed curve may be formed such that that catheter may curve toward one of the left and right bronchi when the distal end of the catheter is in the first orientation. When the distal end of the catheter flips to the second orientation in accordance with the binary response, the distal end may then be curved toward the other of the left and right bronchi. Thus, there is a relationship between the direction of the pre-formed curve and the orientation of the first and second orientations of the distal end of the binary response catheter. Accordingly, a catheter may be provided that enables more confident placement of the distal end of the catheter in one of the left and right bronchi, as well as easy and reliable switching of the distal end between the left and right bronchi.

Figure 30A:
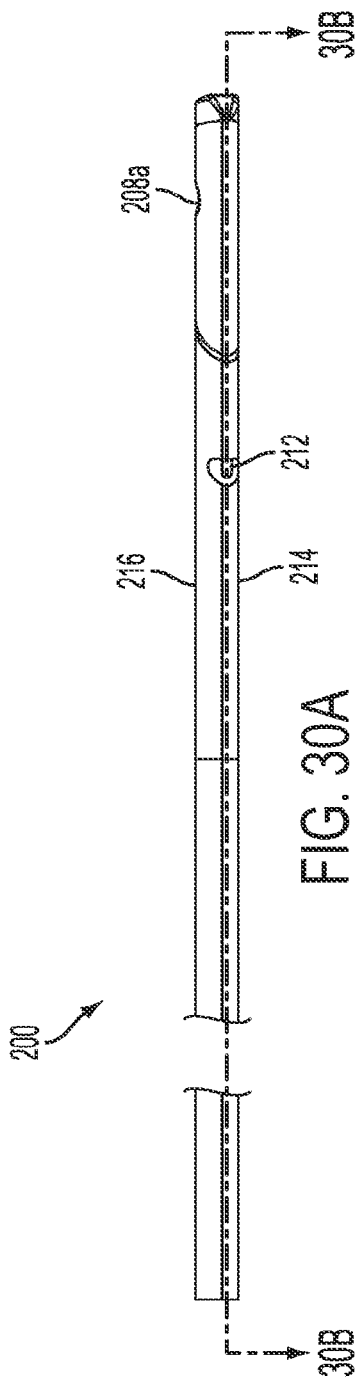
FIG. 30A shows a side view of the catheter in an embodiment of the present invention.
Figure 30B:
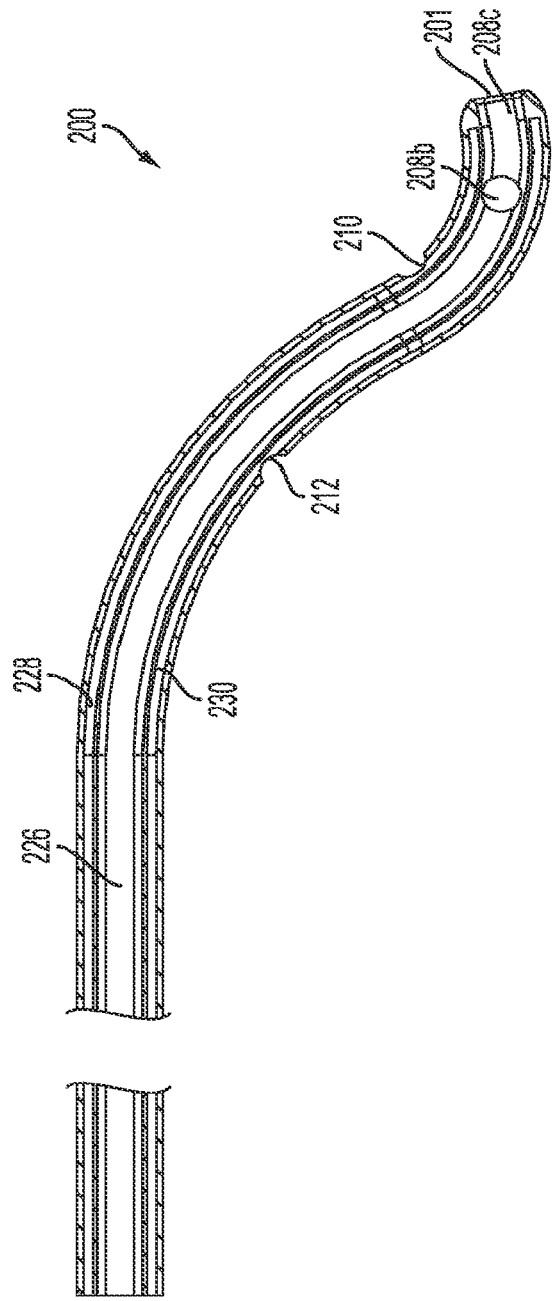
FIG. 30B shows a cross-section view of the catheter taken along line A-A in FIG. 30B in an embodiment of the present invention.
Figures 31A, 31B, 31C, 32A, 32B, 32C, 32D, 32E:
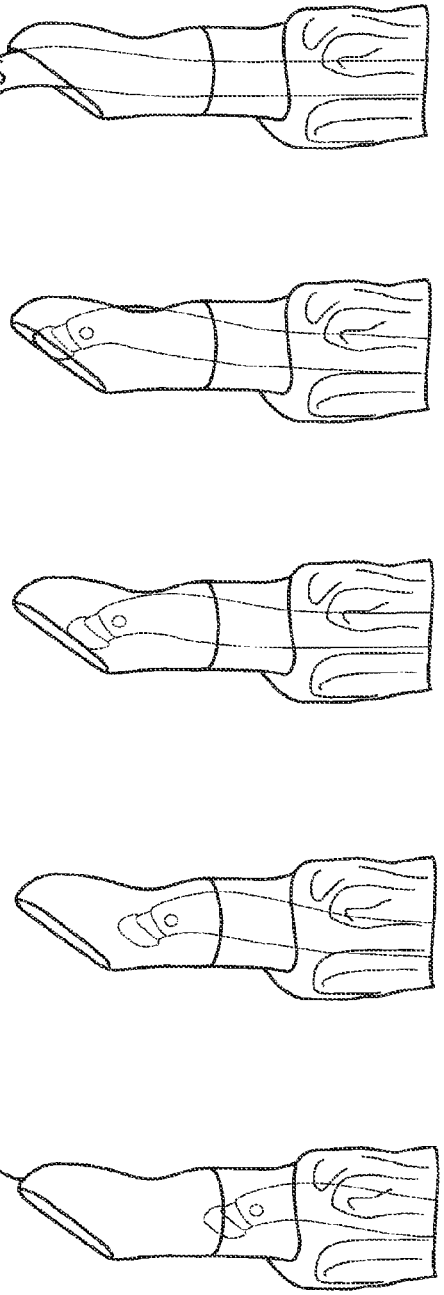
FIGS. 31A, 31B, and 31C show curvatures of a distal end of the catheter according to various embodiments of the present invention.
FIGS. 32A, 32B, 32C, 32D, and 32E show the distal end of the catheter in an embodiment of the present invention over time as it emerges from an outer catheter having a Murphy's Eye opening.

FIG. 30A shows a bottom view of the catheter 200 and FIG. 30B shows a cross-section view of the catheter 200 taken along line A-A in FIG. 30A. According to some embodiments, the catheter 200 may include a first lumen 226, a second lumen 228, and a third lumen 230. From the bottom view in FIG. 30A, the opening 208a of primary lumen 124 can be seen on the curved surface 216, and the opening 212 of the tertiary lumen 160 can be seen. From the cross-sectional view of FIG. 30B, each of the first, second and third lumens 226, 228, and 230 are clearly visible. Openings 208b and 208c of the first lumen 226 are also visible in FIG. 30B, the opening 208b being on the flat side 214 of the catheter 200. In the embodiment shown, the second and third lumens 228 and 230 extend substantially along the entire length of the catheter 200 due to ease in manufacturing of the extrusion. Openings 210 and 212 are opened on the second and third lumens 228, 230, respectively, by the wall of the catheter 200 adjacent to those lumens being skived or opened. The second and third lumens 228, 230 are closed near the tip of the catheter by a pinching or folding of the tip, for example. Thus, only the opening 208c opens on the end tip 201 of the catheter 200.

The pre-formed curve of the catheter also has the advantage of successfully navigating the distal end of the catheter through a Murphy's eye, which may be found on the distal end of a delivery catheter or endotracheal tube, for example. Thus, the catheter may have improved usability over known catheters, which may be obstructed by the Murphy's eye when, for example, an opening on a catheter or a tip of a catheter makes contact with the structure of the Murphy's eye. FIGS. 32A-32E shows an example of a catheter 200 with a pre-formed curve according to an embodiment of the present invention passing through a Murphy's eye 224. Advancement of the position of the catheter can be seen from in the sequence of positions from left to right in FIGS. 32A-32E. By positioning the openings 210 and 212 on the inner curves of the compound curve, the catheter 200 may more easily slide past the Murphy's eye. For example, due to the curvature of the catheter in embodiments of the invention, the edges of openings 210 and 212 may be prevented from rubbing against the Murphy's eye. In some embodiments, only the outer curves of the compound curve may slide against the structure of the Murphy's eye.

FIGS. 33A-33D show four perspective views of the distal end of the catheter 200 according to an embodiment of the invention. FIG. 33A is a bottom view of catheter 200 with the flat side 214 having a normal vector out of the page and an opening 208b. FIG. 33B is a side view showing the relationship of opening 212 and opening 208a to the curved side 216 and flat side 214. FIG. 33C shows a top view of the catheter with a curved side 216, opening 208a, and the distances $d_1$, $d_2$, and $d_3$ between distal tip 201 and opening 208a, between openings 208a and 210, and between openings 210 and 212, respectively. Distance $d_4$ is a distance between the distal tip 201 (with opening 208c) and the opening 212. FIG. 33D is a front view of the distal end of the catheter, and show distal tip 201 and opening 208c, as well as the normal vector N of the flat side 214. In addition to the above features, FIGS. 33A-33D also illustrate the relationship between the openings 210 and 212 relative to the pre-formed curve of the catheter in an embodiment. For example, openings 210 and 212 are each formed on an inner curve of the curved portions of the pre-formed curve. In addition, FIGS. 33A-33D illustrate the relationship between the flat side 214 and the direction of the pre-formed curve according to an embodiment. For example, with the normal vector of the flat side 214 directed out of the page in FIG. 33A, the pre-formed curve curves the catheter towards the top of the page (in the horizontal view shown). Thus, the direction of the curve is orthogonal to the normal vector of the flat side 214.

FIGS. 34A-34F show various isometric views of the catheter according to an embodiment. As shown in FIGS. 34A-34F, both the flat and curved sides 214, 216 can have openings 208a, 208b. As described above, openings 208a and 208b may open to the first lumen 226 for suction. Additionally, opening 208c, shown in FIGS. 34B-34F, can also open to the first lumen 226. In this embodiment, openings 210 and 212 are each formed on inner curves of the pre-formed curve.

Some embodiments of the present invention may include a catheter for insertion into a body lumen of a patient. The catheter may include a distal end configured for insertion into the body lumen of the patient, a proximal end, and an elongated body. The elongated body may extend between the proximal and distal ends and may have a cross-section that includes, over at least a portion of the elongated body, a first side that is flat. The elongated body may also include a second side on an opposite side of the cross-section from the first side. The catheter also may include at least one lumen extending through the elongated body from the proximal end to the distal end. The elongated body may include a pre-formed curve near the distal end. Alternatively, the elongated body may comprise multiple pre-formed curves, or a compound curve. When the distal end is inserted into the body lumen of the patient, the first side of the cross-section may contact a first inner side of a delivery lumen (e.g., an endotracheal tube) of the catheter when the catheter is in a first orientation, and the second side of the cross-section may contact the first inner side of the delivery lumen of the catheter when the catheter is in a second orientation. In some embodiments, the second orientation may be a 180° rotation of the catheter about a longitudinal axis of the elongated body relative to the first orientation. Embodiments of the present invention can include or be used with endotracheal tubes of various diameters, including, for example, diameters of 5 mm to 8 mm.

According to some embodiments, the curve direction (see the arrow in FIGS. 26C and 26D) of the pre-formed curve is 90° with respect to a normal direction N of the flat side of the cross-section. For example, in FIG. 26D, the normal vector N of the flat side 214 is in the direction of z-axis (i.e., coming out of the page) and the curve direction (shown by the arrow) is in the negative y-direction. Also, for comparison, FIG. 26C shows another view of a catheter where the curved side 216 is visible. Thus, in FIG. 26C, the normal vector N of the flat side 214 (not shown) would be in the negative z-direction (i.e., directed into the page). The curve direction (indicated by the arrow in FIG. 26C) is in the negative y-direction. This relationship between the catheter's surface orientation and the direction of the curve can achieve a desirable binary response for easily positioning the distal end of the catheter in either of the left and right bronchi.

According to some embodiments, the second side of the catheter's cross-section is curved. For example, the cross-section may D-shaped. Alternatively, the second side may be flat.

The catheter may also include a curve-direction indicator on the proximal end that indicates a curve direction of the pre-formed curve of the distal end of the catheter. Thus, an operator of the catheter may be assured of the direction in which the distal end of the catheter is disposed. The curve-direction indicator can be a connector or part of a connector on the proximal end of the catheter. The connector may include a central connection portion and a side connection portion extending from the central connection portion, where the direction in which the side connection portion extends corresponds to the curve direction of the preformed curve. For example, a respiration port that extends at an angle from the longitudinal axis of the catheter may serve as the curve-direction indicator.

The curve and the first side of the catheter are arranged such that, when the distal end is inserted into the body lumen of the patient, the curve directs the elongated body toward one of a left bronchus and a right bronchus of the patient in the first orientation, and toward the other of the left bronchus and the right bronchus of the patient in the second orientation. The catheter may have a torsional stiffness such that, when the distal end is inserted into the body lumen of the patient, the distal end remains disposed toward one of the left bronchus and the right bronchus within a range of rotation of the proximal end from 0° to a first predetermined angle. The angle of rotation of the proximal end is, for example, relative to one of the first and second orientations. The distal end of the catheter may be disposed toward the other of the left and right bronchus between the first predetermined angle and a second predetermined angle of the proximal end. In some embodiments, the first predetermined angle is at least 90°, and the second predetermined angle is at least 180°. However, the first predetermined angle may be about 180° and the second predetermined angle may be about 360°. Alternatively, the first predetermined angle may be about 90° and the second predetermined angle may be about 270° in an embodiment. In yet another embodiment, the first predetermined angle may be about 150° and the second predetermined angle may be about 210°.

According to another embodiment of the present invention, a catheter for insertion into a body lumen of a patient is provided that has a distal end configured for insertion into the body lumen of the patient, a proximal end, and an elongated body that extends between the proximal and distal ends. The elongated body may have a cross-section that includes, over at least a portion of the elongated body, a portion that is substantially flat. Additionally, the elongated body may have a torqueability ratio of 1:1 between the distal and proximal ends of the catheter. Further, the catheter may include at least one lumen extending through the elongated body from the proximal end to the distal end. The elongated body may be inserted through a delivery lumen of an outer catheter when in use. When the distal end is inserted into the body lumen of the patient, the distal end may be directed toward one of a left bronchus and a right bronchus of the patient. The distal end remains directed toward the one of the left and right bronchi during a rotation of the proximal end about a longitudinal axis of the elongated body until a predetermined angle of rotation of the proximal end is reached, at which point the distal end flips to the other of the left bronchus and the right bronchus. The predetermined angle may be at least 90°, and may be about 180°.

The catheter may include a pre-formed curve near the distal end that directs the distal end toward one of the left bronchus and the right bronchus. The pre-formed curve may be a compound curve. For example, there may be two curved portions that have different curvatures. When the distal end of the catheter is inserted into the body lumen of the patient, the portion that is substantially flat may contact a first inner side of the delivery lumen when the catheter is in a first orientation. Additionally, the portion that is substantially flat may not contact the first inner side of the delivery lumen when the catheter is in a second orientation. In some embodiments, the portion that is substantially flat may contact the second inner side of the delivery lumen when in the second orientation. The distal end of the catheter may be directed toward one of the left bronchus and the right bronchus in the first orientation and toward the other of the left and right bronchi in the second orientation. The substantially flat portion of the catheter may contact the first inner side of the delivery lumen at only one point in the first orientation, and may contact the first inner side of the delivery lumen at only two points in at least one of the first and the second orientations.

The catheter may be include of a copolymer material, including, for example, a polymer from the Kynar Flex® Copolymer Series. In one example of an embodiment, the polymer is Kynar Flex 2500-20 Medical Grade. However, other alternative materials or equivalents may also be used, including Kynar RX 752 and Pebax 53/60/70/72D, for example.

According to another embodiment of the present invention, a catheter is provided that includes a distal end configured for insertion into the body lumen of the patient, a proximal end, and an elongated body extending between the proximal and distal ends. The elongated body may have a torqueability ratio of 1:1 between the distal and proximal ends. The catheter may also include at least one lumen extending through the elongated body from the proximal end to the distal end. According to this embodiment, the catheter may have a torsional stiffness such that, when the elongated body is inserted into a delivery lumen of an outer catheter, the distal end remains in one of a first resting orientation and a second resting orientation during a rotation of the proximal end about a longitudinal axis of the catheter. The distal end of the catheter may remain in the first resting orientation through greater than 90° of rotation of the proximal end of the catheter and may change from the first resting orientation to the second resting orientation when the proximal end rotates about 180°.

According to another embodiment of the present invention, a method of orienting a catheter in a body lumen of a patient is provided. The method may include providing the catheter that may include a distal end configured for insertion into the body lumen of the patient, a proximal end, and an elongated body extending between the proximal and distal ends. The method may also include providing an outer catheter adapted to be inserted into a body lumen of a patient, as well as to receive the distal end of the catheter. The method may further include inserting the catheter into the body lumen of the patient through the outer catheter and rotationally orienting the proximal end of the catheter to a first orientation. In the first orientation, the distal end of the catheter may be directed toward one of a left bronchus and a right bronchus of the patient. Additionally, the method may include changing a direction of the distal end of the catheter by rotating the proximal end of the catheter to a second orientation. The second orientation may be a substantially 180° rotation of the proximal end relative to the first orientation. The distal end of the catheter may be directed toward the other of the left and right bronchi when the proximal end is in the second orientation.

According to another embodiment of the present invention a catheter is provided that may include a distal end configured for insertion into the body lumen of the patient, a proximal end, and an elongated body extending between the proximal and distal ends. The elongated body may have a cross-section that includes, over at least a portion of the elongated body, a portion that is substantially flat. The catheter may also include a lumen extending through the elongated body from the proximal end to the distal end. The invention is not limited to a single lumen, and embodiments may include multiple lumens, including two, three or more lumens, for example. The catheter may also include a pre-formed curve near the distal end of the elongated body. Some embodiments may have more than one pre-formed curve, or a compound curve. At least one pre-formed curve curves the catheter in a direction that is orthogonal to a normal direction N of the flat side 214 of the catheter 200 (see FIGS. 26C, 26D, and 26F). The elongated body of the catheter may have a torqueability ratio of 1:1 between the distal and proximal ends. The distal end of the catheter can remain directed toward one of the left bronchus and the right bronchus of a patient during a rotation of the proximal end about a longitudinal axis of the elongated body until a predetermined angle of rotation of the proximal end is reached. When the predetermined angle of rotation is reached, the distal end of the catheter flips to the other of the left bronchus and the right bronchus.

When multiple lumens are provided, there may be a first lumen with a first opening near the distal end of the catheter, and a second lumen with a second opening near the distal end of the catheter. The second opening can be spaced apart from the first opening such that the first opening is disposed distally to the second opening. The second opening may be disposed on the inside of the curve of the at least one pre-formed curve, for example.

Although the foregoing description includes some embodiments with two catheters and some embodiments with a single catheter, features of any one of the above-described embodiments may apply to embodiments having either one or two catheters.

The implementations include both open and closed systems. A closed system may include systems where the secretions and/or mucous may be contained in the system. A closed system is shown and described with reference to FIGS. 19-24, for example. An open system is not closed, and the operator may be exposed to the secretions and/or mucous. An open system is shown and described with reference to FIG. 15D, for example. Although in an open system a secretion bag is typically not used, it is contemplated that a secretion bag may be used with the open system.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A respiratory catheter for insertion into an airway of a patient, the respiratory catheter comprising:
   a distal end configured for insertion into the airway of the patient;
   a proximal end;
   an elongated body extending between the proximal and distal ends and having a cross-section that includes, over a majority of the elongated body, a first exterior side that is flat and a second exterior side on an opposite side of the cross-section from the first exterior side forming a D-shape in cross-section;
   at least one pre-formed reverse curve near the distal end of the respiratory catheter, the at least one pre-formed reverse curve comprising a first curve that curves in a first curve direction and a second curve that curves in a second curve direction that opposite to the first curve direction, the second curve being distal to the first curve; and
   at least one lumen extending through the elongated body from the proximal end to the distal end, the at least one lumen being hollow and configured for at least one of delivery of matter to and removal of matter from the airway,
   wherein the D-shape of the cross-section is configured to allow for the distal end of the catheter to be directed in either of two directions corresponding to a left airway and a right airway of the patient,
   wherein the at least one lumen comprises:
      a first lumen with a first opening disposed on an inside curve surface of the first curve, and
      a second lumen with a second opening disposed on an inside curve surface of the second curve, and
   wherein the inside curve surface of the first curve faces a different direction than the inside curve surface of the second curve.

2. The respiratory catheter according to claim 1, wherein the elongated body is adapted to be arranged in a delivery lumen of an outer catheter that has a distal side vent hole, and the at least one pre-formed reverse curve is configured such that the distal end of the catheter bypasses the distal side vent hole.

3. A method of using the respiratory catheter of claim 2, the method comprising:
   advancing the elongated body through the delivery lumen of the outer catheter such that the distal end of the catheter bypasses the distal side vent hole of the outer catheter;
   positioning the distal end of the catheter in an airway of one of a left bronchus and a right bronchus of the patient; and
   performing at least one of aspiration and irrigation of the airway,
   wherein the catheter is disposed relative to the outer catheter such that an outside curve surface of the second curve faces the distal side vent hole of the outer catheter when bypassing the distal side vent hole.

4. The respiratory catheter according to claim 1, wherein the elongated body is configured with structural and material properties such that the distal end remains directed toward one of a left and right bronchi during a rotation of the proximal end about a longitudinal axis of the elongated body until a predetermined angle of rotation of the proximal end is reached, at which point the distal end flips to the other of the left bronchus and the right bronchus, and
   wherein the predetermined angle is greater than or equal to 90° and less than or equal to 180°.

5. A method of using the respiratory catheter of claim 4, the method comprising:
   controlling an angle of rotation of the proximal end of the catheter to direct the distal end toward one of the left and right bronchi;
   advancing the distal end of the catheter until it is disposed at least partially in the one of the left and right bronchi; and
   performing at least one of aspiration and irrigation of the one of the left and right bronchi.

6. The method according to claim 5, further comprising:
   partially retracting the distal end of the catheter so that it is no longer disposed in the one of the left and right bronchi;
   directing the distal end of the catheter towards the other of the first and second bronchi by rotating the proximal end of the catheter about the longitudinal axis of the elongated body until the predetermined angle of rotation is reached; and
   performing at least one of aspiration and irrigation of the other of the first and second bronchi.

7. The respiratory catheter according to claim 1, wherein the elongated body has a torqueability ratio of 1:1 between the distal and proximal ends,
   wherein the 1:1 torqueability is based at least in part on a predetermined rigidity of the elongated body, the predetermined rigidity being based on predetermined physical dimensions of the catheter and predetermined material properties of the catheter,
   wherein the predetermined physical dimensions include the D-shape of the cross-section, a wall thickness of the elongated body, a lumen size of the at least one lumen, an arrangement of the at least one lumen within the cross-section, and a length of the catheter, and
   wherein the predetermined material properties include at least one of hardness, elastic modulus, torsional stiffness, ultimate tensile strength, and yield tensile strength.

8. The respiratory catheter according to claim 7, wherein the predetermined rigidity of the elongated body is achieved at least in part by at least one of:
   a Shore D hardness of the elongated body being about 55 to 60,
   an ultimate tensile strength of the elongated body being about 4000 to 6000 psi,
   a yield tensile strength of the elongated body being about 1700 to 2800 psi,
   a material of the elongated body being made of a polymer comprising at least one of polyvinylidene fluoride, polyvinylidene difluoride and polyether block amide, and
   a length of the D-shape is about 10 mm, and a width of the D-shape is between about 5 mm and about 7 mm.

9. The respiratory catheter according to claim 1, wherein, when the distal end is adapted for insertion into an airway of the patient, the elongated body is configured to be disposed in one of a first orientation or a second orientation, respectively corresponding to the distal end being directed toward one of a left and right bronchi of the patient,
   wherein the catheter has a torsional stiffness such that, when the distal end is adapted for insertion into the airway of the patient, the distal end remains disposed toward one of the left bronchus and the right bronchus within an angle of rotation of the proximal end from 0° to a first predetermined angle, the angle of rotation of the proximal end being relative to one of the first and second orientations, and
   wherein the distal end is disposed toward the other of the left and right bronchus when the angle of rotation of the proximal end is between the first predetermined angle and a second predetermined angle.

10. The catheter according to claim 1, wherein an outside curve surface of the at least one pre-formed reverse curve is a smooth surface that is uninterrupted by any opening to the at least one lumen of the catheter.

11. The respiratory catheter according to claim 1, wherein the at least one lumen is hollow and configured for at least one of aspiration and irrigation.

12. A respiratory catheter system comprising, as a first catheter, the respiratory catheter according to claim 1, and further comprising a second catheter, the second catheter comprising:
    a distal end configured for insertion into the airway of the patient;
    a proximal end;
    an elongated body extending between the proximal and distal ends and having a cross-section that includes, over a majority of the elongated body, a first exterior side that is flat and a second exterior side on an opposite side of the cross-section from the first exterior side forming a D-shape in cross-section;
    at least one lumen extending through the elongated body from the proximal end to the distal end; and
    at least one pre-formed reverse curve near the distal end of the second catheter, the at least one pre-formed reverse curve comprising a first curve that curves in a first curve direction and a second curve that curves in a second curve direction that is opposite to the first curve direction, the second curve being distal to the first curve.

13. The respiratory catheter system according to claim 12, wherein the first and second catheters are rotationally fixed relative to each other such that the first exterior side that is flat of one of the first and second catheters faces the first exterior side that is flat of the other of the first and second catheters, and
    wherein each of the first and second catheters is independently slideable relative to the other of the first and second catheters.

14. The respiratory catheter system according to claim 12, wherein the at least one pre-formed reverse curve of each of the first and second catheters curves within a plane that is orthogonal to a normal direction of the first exterior side that is flat of each of the first and second catheters, and
    wherein the pre-formed reverse curves of the first and second catheters curve the first and second catheters in opposite directions when both of the first and second catheters are adapted for insertion into the airway.

15. The respiratory catheter according to claim 1, wherein, in a relaxed state, the first and second curves of the at least one pre-formed reverse curve are substantially coplanar with the first exterior side that is flat.

16. The respiratory catheter according to claim 1, wherein, in a relaxed state, the elongated body has a longitudinal axis extending in a first direction over a majority of the elongated body, and a central axis of a distal tip at the distal end extends in a second direction that is non-parallel to the first direction of the longitudinal axis.

17. The respiratory catheter according to claim 1, wherein, in a relaxed state of the catheter, the first and second curves lie in-plane with the elongated body, and
    wherein the distal end has a longitudinal axis at a distal tip of the distal end that is non-parallel to a longitudinal axis of the elongated body.

18. The respiratory catheter according to claim 17, wherein curvatures of the first and second curves lie in a plane that is orthogonal to a normal vector of the first exterior side of the elongated body that is flat.

19. The respiratory catheter according to claim 17, wherein a tangent line of a distal end of curvature of the second curve is non-parallel to a longitudinal axis of the elongated body.

20. The respiratory catheter according to claim 17, wherein, when the catheter is inserted into the patient through an endotracheal tube, the first and second curves are configured to prevent the distal end of the catheter from being caught on a Murphy eye of the endotracheal tube via the longitudinal axis at the distal tip of the distal end diverging from the longitudinal axis of the elongated body.

21. The respiratory catheter according to claim 1, wherein a distal end of curvature of the first curve is coincident with a proximal end of curvature of the second curve.

22. A catheter system comprising a catheter for insertion into an airway of a patient, the catheter comprising:
    a distal end configured for insertion into the airway of the patient;
    a proximal end;
    an elongated body extending between the proximal and distal ends, the elongated body having at least one reverse curve located near the distal end and having a cross-section that includes, over a majority of the elongated body, a first exterior side that is flat and a second exterior side on an opposite side of the cross-section from the first exterior side; and
    at least one lumen extending through the elongated body from the proximal end to the distal end,
    wherein, when the distal end is adapted for insertion into the airway of the patient, the catheter is only capable, due to structural and material properties of the catheter, of having a resting disposition in two orientations within the airway: a first orientation and a second orientation, the second orientation being substantially an 180° rotation of the catheter about a longitudinal axis of the elongated body relative to the first orientation,
    wherein the at least one reverse curve and the first exterior side are arranged such that, when the distal end is adapted for insertion into the airway of the patient, the distal end is directed toward one of a left bronchus and a right bronchus of the patient in the first orientation, and toward the other of the left bronchus and the right bronchus of the patient in the second orientation,
    wherein the at least one lumen comprises:
        a first lumen with a first opening disposed on an inside curve surface of a first curve of the at least one reverse curve, and
        a second lumen with a second opening disposed on an inside surface of a second curve of the at least one reverse curve, and
    wherein the inside curve surface of the first curve faces a different direction than the inside curve surface of the second curve.

23. The catheter system according to claim 22, wherein a majority of the elongated body has a D-shaped cross-section.

24. The catheter system according to claim 22, wherein the second exterior side is one of flat and curved.

25. The catheter system according to claim 22, wherein the at least one pre-formed reverse curve lies in a plane that is 90° with respect to a normal direction of the first exterior side of the cross-section.

26. A catheter for insertion into an airway of a patient, the catheter comprising:
- a distal end configured for insertion into the airway of the patient;
- a proximal end adapted for manual manipulation by a human operator when the distal end is inserted into the airway of the patient;
- an elongated body extending between the proximal and distal ends and having a cross-section that includes, over a majority of the elongated body, a first exterior side that is flat and a second exterior side that is curved on an opposite side of the cross-section from the first exterior side, the first and second exterior sides together forming a D-shape in cross-section;
- at least one pre-formed reverse curve near the distal end of the catheter, the at least one pre-formed reverse curve comprising a first curve that curves in a first curve direction and a second curve that curves in a second curve direction that is opposite to the first curve direction;
- at least one lumen extending through the elongated body from the proximal end to the distal end, the at least one lumen being hollow and configured for at least one of delivery of matter to and removal of matter from the airway; and
- a plurality of openings into the at least one lumen, the plurality of openings including an opening formed on an inside curve surface of each of the first and second curves,
- wherein, in a relaxed state of the catheter, the first and second curves lie in-plane with the elongated body, and
- wherein the first and second curves line in a plane that is orthogonal to a normal vector of the first exterior side of the elongated body that is flat.

27. A respiratory catheter for insertion into an airway of a patient, the respiratory catheter comprising:
- a distal end configured for insertion into the airway of the patient in either one of two directions corresponding to a left bronchus and a right bronchus;
- a proximal end adapted for manual manipulation by a human operator when the distal end is inserted into the airway;
- an elongated body extending between the proximal and distal ends and having a cross-section that includes, over a majority of the elongated body, a first exterior side that is flat and a second exterior side that is curved on an opposite side of the cross-section from the first exterior side, the first and second exterior sides together forming a D-shape in cross-section; and
- at least one lumen extending through the elongated body from the proximal end to the distal end, the at least one lumen being hollow and configured for at least one of delivery of matter to and removal of matter from the airway;
- at least one pre-formed reverse curve near the distal end of the respiratory catheter, the at least one pre-formed reverse curve comprising a first curve that curves in a first curve direction and a second curve that curves in a second curve direction that is opposite to the first curve direction, the second curve being distal to the first curve; and
- wherein the at least one lumen comprises:
  - a first lumen with a first opening disposed on an inside curve surface of the first curve, and
  - a second lumen with a second opening disposed on an inside curve surface of the second curve, and
- wherein the inside curve surface of the first curve faces a different direction than the inside curve surface of the second curve;
- wherein the respiratory catheter is configured to direct the distal end in the either one of two directions corresponding to the left bronchus of the patient in a first disposition and the right bronchus of the patient in a second disposition by abutting the first exterior side that is flat with an interior surface of an endotracheal tube, and
- wherein the abutment of the first exterior side that is flat with the interior surface of the endotracheal tube prevents the distal end from deviating from a desired direction of the two directions.

28. The respiratory catheter according to claim 27, wherein the proximal end of the catheter comprises a directional indicator that indicates a direction in which the distal end of the catheter is directed, and
- wherein the catheter is configured to direct the distal end to the other of the two directions corresponding to the left bronchus and the right bronchus of the patient when the human operator rotates the proximal end of the catheter.

29. The respiratory catheter according to claim 27, wherein the at least one pre-formed reverse curve and a longitudinal axis of the elongated body are substantially coplanar in a plane when the elongated body is in a relaxed state, the plane being orthogonal to a normal vector of the first side that is flat.

* * * * *